(12) United States Patent
Snider et al.

(10) Patent No.: US 10,303,844 B2
(45) Date of Patent: May 28, 2019

(54) MULTIMARKER RISK STRATIFICATION

(71) Applicant: Critical Care Diagnostics, Inc., San Diego, CA (US)

(72) Inventors: James V. Snider, San Diego, CA (US); Robert W. Gerwien, Newington, CT (US); Sven Jacobson, New York, NY (US)

(73) Assignee: Critical Care Diagnostics, Inc., San Diego, CA (US)

( * ) Notice: Subject to any disclaimer, the term of this patent is extended or adjusted under 35 U.S.C. 154(b) by 198 days.

(21) Appl. No.: 15/385,095

(22) Filed: Dec. 20, 2016

(65) Prior Publication Data
US 2017/0169179 A1 Jun. 15, 2017

Related U.S. Application Data

(63) Continuation of application No. 13/972,596, filed on Aug. 21, 2013, now abandoned.

(60) Provisional application No. 61/691,706, filed on Aug. 21, 2012.

(51) Int. Cl.
G16H 50/30 (2018.01)
G06F 19/00 (2018.01)

(52) U.S. Cl.
CPC .............. *G06F 19/00* (2013.01); *G16H 50/30* (2018.01)

(58) Field of Classification Search
CPC ............ G01N 33/6893; G01N 2800/50; G06F 19/00; G06F 19/3431; G16H 50/30
See application file for complete search history.

(56) References Cited

U.S. PATENT DOCUMENTS

| | | |
|---|---|---|
| 5,786,163 A | 7/1998 | Hall |
| 6,040,147 A | 3/2000 | Ridker et al. |
| 6,210,976 B1 | 4/2001 | Sabbadini et al. |
| 6,288,218 B1 | 9/2001 | Levinson |
| 6,309,888 B1 | 10/2001 | Holvoet et al. |
| 6,323,334 B1 | 11/2001 | Kingsbury et al. |
| 6,905,827 B2 | 6/2005 | Wohlgemuth et al. |
| 7,087,396 B2 | 8/2006 | Tominaga et al. |
| 7,358,062 B2 | 4/2008 | Suovaniemi et al. |
| 7,432,060 B2 | 10/2008 | Lee |
| 7,655,415 B2 | 2/2010 | Lee |
| 7,670,769 B2 | 3/2010 | Lee |

(Continued)

FOREIGN PATENT DOCUMENTS

| | | |
|---|---|---|
| EP | 1731910 | 12/2006 |
| JP | 2005-538700 | 12/2005 |

(Continued)

OTHER PUBLICATIONS

Mayo Clinic, Interpretive Handbook Test 61723: ST2, Serum, Aug. 8, 2012, Mayo Medical Laboratories, http://www.mayomedical-laboratories.com/interpretive-guide/?alpha=S&unit_code=61723, pp. 1-3 (Year: 2012).*

(Continued)

*Primary Examiner* — Joy Chng
(74) *Attorney, Agent, or Firm* — Fish & Richardson P.C.

(57) ABSTRACT

Measurement of circulating ST2 and natriuretic peptide (e.g., NT-proBNP) concentrations is useful for the prognostic evaluation of subjects, in particular for the prediction of adverse clinical outcomes, e.g., mortality, transplantation, and heart failure.

19 Claims, 57 Drawing Sheets

Top 10 Models
Study Outcomes (Size =1-5)

| Model No | K | Age_Yr | ST2gte50 | NYHAgte3 | Troponin | | lneGFR | lnHGB | lnCreat | SBP | CAD | HTN | Model Fit | | | Discrimition | | | |
|---|---|---|---|---|---|---|---|---|---|---|---|---|---|---|---|---|---|---|---|
| | | | | | TROPONINgte16 | lnTroponin | | | | | | | loglik | AIC | BIC | AUC | bsAUC | LCI | UCI |
| 16776 | 5 | 1.67 | 1.39 | 1.34 | 1.65 | | 0.84 | | | | | | -1881.2 | 3772.3 | 3796.3 | 0.818 | 0.817 | 0.782 | 0.853 |
| 16581 | 5 | 1.60 | 1.37 | 1.35 | 1.65 | | 0.89 | | | | | | -1884.6 | 3779.2 | 3803.2 | 0.817 | 0.817 | 0.775 | 0.859 |
| 16692 | 5 | 1.71 | 1.36 | 1.30 | | 1.54 | 0.85 | | | | | | -1882.5 | 3775.1 | 3799.0 | 0.818 | 0.816 | 0.773 | 0.858 |
| 17095 | 5 | 1.69 | 1.38 | 1.35 | 1.70 | | | | 0.98 | | | | -1886.1 | 3782.2 | 3806.1 | 0.815 | 0.815 | 0.777 | 0.853 |
| 13616 | 5 | 1.68 | 1.38 | 1.36 | 1.70 | | | | | 1.01 | | | -1886.1 | 3782.3 | 3806.2 | 0.816 | 0.815 | 0.776 | 0.853 |
| 16317 | 5 | 1.68 | 1.37 | 1.36 | 1.64 | | | 1.13 | | | | | -1884.2 | 3778.3 | 3802.3 | 0.817 | 0.815 | 0.777 | 0.852 |
| 3526 | 4 | 1.72 | 1.36 | 1.33 | | 1.59 | | | | | | | -1887.2 | 3782.5 | 3801.6 | 0.815 | 0.814 | 0.774 | 0.854 |
| 3610 | 4 | 1.68 | 1.38 | 1.36 | 1.70 | | | | | | | | -1886.2 | 3780.3 | 3799.5 | 0.815 | 0.814 | 0.777 | 0.851 |
| 16497 | 5 | 1.66 | 1.35 | 1.33 | | 1.55 | 0.92 | | | | | | -1886.5 | 3783.0 | 3807.0 | 0.816 | 0.814 | 0.774 | 0.854 |
| 15971 | 5 | 1.70 | 1.38 | 1.36 | 1.71 | | | | | | | 0.94 | -1885.6 | 3781.3 | 3805.3 | 0.817 | 0.813 | 0.773 | 0.853 |

Markers Not Selected: LVEF    SBP<120    Sex
Ln (NT-proBNP)    BMI    ST2>=35    Diabetes
DBP    NT-proBNP>=1700    ST2 3 Group
Ln (ST2)    GFR<50    BMI >=25

(56) References Cited

U.S. PATENT DOCUMENTS

| | | | |
|---|---|---|---|
| 7,985,558 B2 | 7/2011 | Lee | |
| 7,989,210 B2 | 8/2011 | Lee | |
| 7,998,683 B2 | 8/2011 | Snider et al. | |
| 8,090,562 B2 | 1/2012 | Snider et al. | |
| 8,420,785 B2 | 4/2013 | Snider et al. | |
| 8,530,173 B2 | 9/2013 | Lee | |
| 8,597,958 B2 | 12/2013 | Lee | |
| 8,617,825 B2 | 12/2013 | Snider et al. | |
| 8,728,742 B2 | 1/2014 | Snider | |
| 8,734,769 B2 | 1/2014 | Lee | |
| 8,748,110 B2 | 6/2014 | Snider et al. | |
| 8,748,116 B2 | 6/2014 | Lee | |
| 8,871,452 B2 | 10/2014 | Lee | |
| 2003/0124624 A1 | 7/2003 | Tominaga et al. | |
| 2003/0228570 A1 | 12/2003 | Yat Wah Tom et al. | |
| 2004/0048286 A1 | 3/2004 | Lee et al. | |
| 2004/0121343 A1 | 6/2004 | Buechler et al. | |
| 2004/0133079 A1 | 7/2004 | Mazar et al. | |
| 2005/0196817 A1 | 9/2005 | Kingsmore | |
| 2005/0203046 A1 | 9/2005 | Schmitz et al. | |
| 2005/0250156 A1 | 11/2005 | Shebuski et al. | |
| 2005/0272054 A1 | 12/2005 | Cargill et al. | |
| 2006/0216755 A1 | 9/2006 | Lee | |
| 2007/0042978 A1 | 2/2007 | Girard et al. | |
| 2007/0248981 A1 | 10/2007 | Snider et al. | |
| 2008/0003199 A1 | 1/2008 | Lee | |
| 2009/0111708 A1 | 4/2009 | Seddon et al. | |
| 2009/0192078 A1 | 7/2009 | Lee | |
| 2009/0264779 A1* | 10/2009 | Snider | C12Q 1/6883 600/508 |
| 2009/0305265 A1 | 12/2009 | Snider et al. | |
| 2010/0009356 A1 | 1/2010 | Snider et al. | |
| 2010/0055683 A1 | 3/2010 | Snider et al. | |
| 2010/0267062 A1* | 10/2010 | Frey | G01N 33/6887 435/7.92 |
| 2011/0053170 A1 | 3/2011 | Snider et al. | |
| 2011/0137131 A1* | 6/2011 | Adourian | G01N 33/6893 600/300 |
| 2011/0250703 A1 | 10/2011 | Lee | |
| 2011/0256635 A1 | 10/2011 | Snider | |
| 2011/0262941 A1 | 10/2011 | Snider | |
| 2011/0280887 A1 | 11/2011 | Lee | |
| 2012/0040381 A1 | 2/2012 | Snider et al. | |
| 2012/0065897 A1 | 3/2012 | Snider et al. | |
| 2012/0276551 A1 | 11/2012 | Snider | |
| 2013/0177931 A1 | 7/2013 | Snider et al. | |
| 2013/0244236 A1 | 9/2013 | Snider et al. | |
| 2013/0251664 A1 | 9/2013 | Lee | |
| 2013/0273562 A1 | 10/2013 | Lee | |
| 2013/0317030 A1 | 11/2013 | Lee | |
| 2013/0345805 A1 | 12/2013 | Snider et al. | |
| 2014/0045200 A1 | 2/2014 | Snider et al. | |
| 2014/0051773 A1 | 2/2014 | Snider | |
| 2014/0058743 A1 | 2/2014 | Snider et al. | |
| 2014/0234875 A1 | 8/2014 | Snider | |
| 2014/0286944 A1 | 9/2014 | Snider et al. | |
| 2014/0302536 A1 | 10/2014 | Lee | |
| 2015/0081224 A1 | 3/2015 | Snider et al. | |
| 2015/0153360 A1 | 6/2015 | Lee | |

FOREIGN PATENT DOCUMENTS

| | | |
|---|---|---|
| JP | 2007-515632 | 6/2007 |
| JP | 2007-248395 | 9/2007 |
| WO | WO 1998/07754 | 2/1998 |
| WO | WO 1998/38311 | 9/1998 |
| WO | WO 2000/35473 | 6/2000 |
| WO | WO 2000/35951 | 6/2000 |
| WO | WO 2001/70817 | 9/2001 |
| WO | WO 2001/73498 | 10/2001 |
| WO | WO 2002/38794 | 5/2002 |
| WO | WO 2003/094856 | 11/2003 |
| WO | WO 2004/056868 | 7/2004 |
| WO | WO 2005/55810 | 6/2005 |
| WO | WO 2005/055810 | 6/2005 |
| WO | WO 2006/77265 | 7/2006 |
| WO | WO 2007/127749 | 11/2007 |
| WO | WO 2012/059477 | 5/2012 |

OTHER PUBLICATIONS

FDA, Substantial Equivalence Determination Decision Summary, Dec. 26, 2011, Food and Drug Administration, http://www.accessdata.fda.gov/cdrh_docs/reviews/K111452.pdf, pp. 1-17 (Year: 2011).*
U.S. Appl. No. 14/290,465, filed May 29, 2014, Lee.
U.S. Appl. No. 29/503,093, filed Sep. 23, 2014, Snider et al.
U.S. Appl. No. 29/503,097, filed Sep. 23, 2014, Snider et al.
U.S. Appl. No. 29/503,095, filed Sep. 23, 2014, Snider et al.
U.S. Appl. No. 14/523,694, filed Oct. 24, 2014, Lee.
U.S. Appl. No. 14/566,938, filed Dec. 11, 2014, Snider et al.
U.S. Appl. No. 14/566,955, filed Dec. 11, 2014, Snider et al.
U.S. Appl. No. 14/592,961, filed Jan. 9, 2015, Snider et al.
Auer et al, "C-reactive protein and coronary artery disease," Jpn Heart J., 43(6):607-619 (2002).
Aukrust et al., "Cytokine network in congestive heart failure secondary to ischemic or idiopathic dilated cardiomyopathy," Am J Cardiol., 83(3):376-382 (1999).
Baumgarten et al., "Cytokines as emerging targets in the treatment of heart failure," Trends Cardiovasc Med., 10(5):216-223 (2000).
Bayés-Genís Antoni, "[The circulating NTproBNP level, a new biomarker for the diagnosis of heart failure in patients with acute shortness of breath]," Revista Española de Cardiología, 58(10):1142-1144 (2005).
Belch et al., "Oxygen free radicals and congestive heart failure," Br Heart J., 65(5):245-248 (1991).
Blum et al., "Pathophysiological role of cytokines in congestive heart failure," Annu. Rev. Med., 52:15-27 (2001) (abstract).
Boisot et al., "Serial Sampling of ST2 Predicts 90-Day Mortality Following Destabilized Heart Failure," Journal of Cardiac Failure, 14:732-738 (2008).
Brint et al., "ST2 is an inhibitor of interleukin 1 receptor and Toll-like receptor 4 signaling and maintains endotoxin tolerance," Nat. Immunol., 5(4):373-379 (2004).
Bruneau, "Selective changes in natriuretic peptide and early response gene expression in isolated rat atria following stimulation by stretch or endothelin-1," Cardiovasc. Res., 28(10):1519-1525 (1994).
Brunner et al., "Increased levels of soluble ST2 protein and IgG1 production in patients with sepsis and trauma," Intensive Care Med., 30(7):1468-1473 (2004).
Carter et al., "Regulation of ST2L expression of T helper (Th) type 2 cells," Eur. J. Immunol., 31(10):2979-2985 (2001). (Abstract Only).
Chan et al., "Human IL018 Receptor and ST2L are Stable and Selective Markers for the Respective Type I and Type 2 Circulating Lymphocytes," J. Immunol. 167(3) 1238-1244 (2001) (abstract).
Clerico and Emdin, Clin. Chem., 50:33-50 (2004).
Comm. CA 2,484,897; Dec. 20, 2010; 5 pp.
Comm. CA 2,484,897; Feb. 24, 2012; 3 pp.
Comm. CA 2,484,897; Feb. 4, 2014.
Comm. CA 2,484,897; Mar. 21, 2013; 2 pp.
Communication dated Nov. 30, 2009 for EP 03728848.7; 11 pp.
Communication dated Dec. 10, 2012 for EP 10184644.2; 5 pp.
Communication dated Feb. 2, 2012 for EP 10184644.2; 6 pp.
Communication dated Apr. 28, 2014 for EP 10184644.2.
Communication dated May 2, 2011 for EP 10184644.2.
Communication dated Jun. 7, 2010 for EP 03728848.7; 7 pp.
Communication pursuant to Article 94(3) EPC, EP Application No. 09731842.2, dated Nov. 13, 2012, 3 pp.
Dale et al., Interleukin-1 Receptor Cluster: Gene Organization of IL1R2, IL1R1, IL1RL2 (IL-1Rrp2), IL1RL1 (T1/ST2), and IL18R1 (IL-1Rrp) on Human Chromosome 2q,) Genomics, 57:177-179 (1999).
European Search Report issued in EP 13 17 9055; dated Sep. 13, 2013, 4 pp.
European Search Report; European Patent Application No. 07761219.0-1223; dated May 13, 2009.

(56) References Cited

OTHER PUBLICATIONS

European Search Report; European Patent Application No. 10171764.3-1223; dated Oct. 6, 2010.
Examiner's First Report on Patent; AU Appl. No. 2007244927; dated Nov. 22, 2010; 5pp.
Feldman et al., "C-reactive protein is an independent predictor of mortality in women with HIV-1 infection," J. Acquir. Immune Defic. Syndr., 32(2):210-214 (2003). (abstract).
First Office Action dated Apr. 27, 2013 in CN 201110387886.6.
Forssmann et al., "The heart is the center of a new endocrine, paracrine, and neuroendocrine system," Arch. Histol. Cytol., 52 Suppl:293-315 (1989). (Abstract).
Fourth Office Action; CN Appln. No. 03816298.9; dated Aug. 12, 2011; 3 pp.
Frangogiannis et al., "Resident cardiac mast cells degranulate and release preformed TNF-alpha, initiating the cytokine cascade in experimental canine myocardial ischemia/reperfusion," Circulation., 98(7):699-710 (1998).
Galvani et al., "Prognostic influence of elevated values of cardiac troponin I in patients with unstable angina," Circulation, 95(8):2053-2059 (1997). (Abstract).
Gegenhuber et al., "B-type natriuretic peptide and amino terminal proBNP predict one-year mortality in short of breath patients independently of the baseline diagnosis of acute destabilized heart failure," Clinica Chimica Acta, 370(1-2):174-179 (2006).
Goetze et al., "B-type natriuretic peptide and its precursor in cardiac venous blood from failing hearts," European Journal of Heart Failure, 7(1):69-74 (2005).
Goldstein, Am J Cardiol, Dec. 1981; 48(6):1147-54. (Abstract Only).
Gwechenberger et al., Cardiac myocytes produce interleukin-6 in culture and in viable border zone of reperfused infarctions. Circulation. Feb. 2, 1999;99(4):546-51.
Heeschen et al., Predictive value of C-reactive protein and troponin T in patients with unstable angina. a comparative analysis. Capture Investigators. Chimeric c7E3 AntiPlatelet Therapy in Unstable angina Refractory to standard treatment trial. J Am Coll Cardiol. May 2000;35(6):1535-42. Abstract Only.
International Preliminary Report on Patentability for International Application No. PCT/US2013/056020 dated Feb. 24, 2015, 7 pages.
International Preliminary Report on Patentability for PCT/US2007/067333, dated Oct. 28, 2008.
International Preliminary Report on Patentability for PCT/Us2009/040941; dated Oct. 19, 2010.
International Search Report and Written Opinion of the International Searching Authority for PCT/US2013/056020 dated Dec. 12, 2013, 11 pages.
International Search Report for PCT/1J52009/040941, completed Dec. 2, 2009, dated Dec. 3, 2009.
IPER as issued in PCT/US01/46816 dated Apr. 19, 2004.
ISR as issued in PCT/US01/46816 dated May 9, 2003.
ISR as issued in PCT/US2003/14882 dated Feb. 9, 2005.
ISR as issued in PCT/US2007/067333 dated Jan. 23, 2008.
Januzzi et al., "Measurement of the Interleukin Family Member ST2 in Patients with Acute Dyspnea: Results from the PRIDE (Pro-Brain Natriuretic Peptide Investigation of Dyspnea in the Emergency Department) Study," J. Am. Coll. Cardiol., 50:607-613 (2007).
Januzzi et al., "NT-proBNP testing for diagnosis and short-term prognosis in acute destabilized heart failure: an international pooled analysis of 1256 patients: the International Collaborative of NT-proBNP Study," Eur. Heart J., 27(3):330-337 (2006).
Januzzi et al., "The N-terminal Pro-BNP investigation of dyspnea in the emergency department (PRIDE) study," Am. J. Cardiol., 95(8):948-954 (2005).
Januzzi et al., "The value of soluble ST2 measurement for the diagnostic and prognostic evaluation of patients with acute dyspnea," Circulation, 114(18):721 (2006) (abstract).
Januzzi et al., "Utility of amino-terminal pro-brain natriuretic Peptide testing for prediction of 1-year mortality in patients with dyspnea treated in the emergency department," Arch. Intern. Med., 166(3):315-320 (2006).
Kakkar et al., "The IL-33/ST2 pathway: Therapeutic target and novel biomarker," Nature Reviews Drug Discovery, 7(10):827-840 (2008).
Kida et al., Pathophysiological role of natriuretic peptides. Rinsho Byori. Aug. 1989;37(8):875-82. Abstract Only.
Kieser et al., "Identification of the primary growth response gene, ST2/T1, as a gene whose expression is differentially regulated by different protein kinase C isozymes," FEBS Lett., 372(2-3):189-193 (1995).
Kip et al.; "The problem with composite end points in cardiovascular studies," J. Am. Coll. Cardiol. 51:701-707 (2008).
Knudsen et al., "Predictors of elevated B-type natriuretic peptide concentrations in dyspneic patients without heart failure: an analysis from the breathing not properly multinational study," Ann. Emerg. Med., 45(6):573-580 (2005).
Krauser et al., "Effect of body mass index on natriuretic peptide levels in patients with acute congestive heart failure: a ProBNP Investigation of Dyspnea in the Emergency Department (PRIDE) substudy," Am. Heart J., 149(4):744-750 (2005).
Kumar et al., Expression of ST2, an interleukin-1 receptor homologue, is induced by proinflammatory stimuli. Biochem Biophys Res Commun. Jun. 27, 1997;235(3):474-8.
Kuroiwa et al., "Construction of ELISA system to quantify human ST2 protein in sera of patients. Hybridoma," 19(2):151-159 (2000).
Kuroiwa K, et al., Identification of Human ST2 Protein in the Sera of Patients with Autoimmune Diseases. Biochemical and Biophysical Research Communications 2001; 284:1104-8.
Lee et al., "Novel markers for heart failure diagnosis and prognosis," Curr Opin Cardiol, 20(3):201-210 (2005)(cited by 0005CA Office action dated Aug. 18, 2010).
Leyva et al., European Heart J., 19:1814-1822 (1998).
Linares et al.; "C-reactive protein (CRP) levels in systemic lupus erythematosus (SLE)," 5:66-69 (1986)(Abstract).
Lohning et al., "T1/ST2 is preferentially expressed on murine Th2 cells, independent of interleukin 4, interleukin 5, and interleukin 10, and important for Th2 effector function," Proc. Natl. Acad. Sci. U.S.A., 95(12):6930-6935 (1998).
MacGowan et al., Circulating interleukin-6 in severe heart failure. Am J Cardiol. Apr. 15, 1997;79(8):1128-31.
MacKenna et al., Role of mechanical factors in modulating cardiac fibroblast function and extracellular matrix synthesis. Cardiovasc Res. May 2000;46(2):257-63.
Maisel et al., "Bedside B-Type Natriuretic Peptide in the Emergency Diagnosis of Heart Failure With Reduced or Preserved Ejection Fraction," J. Am. Coll. Cardiol., 41:2010-7i (2003).
Maisel et al., "Primary results of the Rapid Emergency Department Heart Failure Outpatient Trial (REDHOT). A multicenter study of B-type natriuretic peptide levels, emergency department decision making, and outcomes in patients presenting with shortness of breath," J. Am. Coll. Cardiol., 44(6):1328-1333 (2004).
Maisel et al., "Rapid measurement of B-type natriuretic peptide in the emergency diagnosis of heart failure," N. Engl. J. Med., 347(3):161-167 (2002).
Mann et al., Stress activated cytokines and the heart. Cytokine Growth Factor Rev. Dec. 1996;7(4):341-54.
McCord et al., "Relationship between obesity and B-type natriuretic peptide levels," Arch. Intern. Med., 164(20):2247-2252 (2004).
Millenium Pharmaceuticals, Inc. Millenium Pharmaceuticals Identifies a Key mediator of Allergic Immune Response. Press Release Oct. 4, 1999, 2 pages.
Mitcham et al., T1/ST2 signaling establishes it as a member of an expanding interleukin-1 receptor family. J Biol Chem. Mar. 8, 1996;271(10):5777-83.
Moe et al., "Neurohormonal activation in severe heart failure: relations to patient death and the effect of treatment with flosequinan," Am. Heart. J., 139:587-95 (2000).
Morrison et al., ""Utility of a Rapid B-Natriuretic Peptide Assay in Differentiating Congestive Heart Failure from Lung Disease in

(56) References Cited

OTHER PUBLICATIONS

Patients Presenting With Dyspnea,"" Journal of American College of Cardiology, 2002, 39: 202-209.
Mueller et al. Use of B-Type Natriuretic Peptide for the Management of Women With Dyspnea, Am J Cardiol 2004;94:1510-1514.
Mueller et al., "Use of B-type natriuretic peptide in the evaluation and management of acute dyspnea," New England Journal of Medicine, 350(7):647-654 (2004).
Mukoyama et al., Augmented secretion of brain natriuretic peptide in acute myocardial infarction. Biochem Biophys Res Commun. Oct. 15, 1991;180(1):431-6. Abstract Only.
Murphy et al., Signaling and transcription in T helper development. Annu Rev Immunol. 2000;18:451-94.
Ng et al., Diagnosis of heart failure using urinary natriuretic peptides. Clin Sci (Lond). Feb. 2004;106(2):129-33.
Notice of Reasons for Rejection dated Sep. 20, 2011 for JP 2009-173539.
Notice of Reasons for Rejection; Japanese Patent Application No. 2011-505224; dated Sep. 4, 2013 (with English translation).
Notice of Reasons for Rejection; JP 2009-507931; dated Aug. 20, 2012; 2 pp.
Notice of Reasons for Rejection; JP Appl. No. 2009-507931; dated Oct. 26, 2011; 3 pp.
Nozaki et al., Soluble Tumor Necrosis Factor Receptors are Elevated in Relation to Severity of Congestive Heart Failure, Jpn Circ J 1997; 61:657-64.
O'Neill et al., The IL-1 receptor/toll-like receptor superfamily: crucial receptors for inflammation and host defense. Immunol Today. May 2000;21(5):206-9.
Ohki R et al. Identification of mechanically induced genes in human monocytic cells by DNA microarrays. J. Hypertens., Apr. 2002; 20(4):685-691 Abstract Only.
Ohtsuka et al., Effect of beta-blockers on circulating levels of inflammatory and anti-inflammatory cytokines in patients with dilated cardiomyopathy. J Am Coll Cardiol. Feb. 2001;37(2):412-7.
Ordonez-Llamos et al., "A formula for combining ST2 and NT-pro-BNP enhances prognostic accuracy in patients with heart failure," Clin. Chem. 54:A99 (2008).
Orús et al., Prognostic Value of Serum Cytokines in Patients with Congestive Heart Failure, J Heart Lung Transplant 2000; 19:419-25.
Oshikawa et al., "Acute eosinophilic pneumonia with increased soluble ST2 in serum and bronchoalveolar lavage fluid," Respir. Med., 95(6):532-533 (2001).
Oshikawa et al., "Elevated Soluble ST2 Protein Levels in Sera of Patients with Asthma with an Acute Exacerbation," Am. J. Respir. Crit. Care Med. 164:277-281 (2001).
Oshikawa et al., "Expression and function of the ST2 gene in a murine model of allergic airway inflammation," Clin. Exp. Allergy, 32(10):1520-1526 (2002).
Oshikawa et al., "Expression of ST2 in helper T lymphocytes of malignant pleural effusions," Am. J. Respir. Crit. Care Med., 165(7):1005-1009 (2002).
Oshikawa et al., "ST2 protein induced by inflammatory stimuli can modulate acute lung inflammation," Biochem. Biophys. Res. Commun., 299(1):18-24 (2002).
Pascual Figal Domingo et al., "Usefulness of NTproBNP in the emergency management of patients with severe syspnea and an uncertain heart failure diagnosis," Revista Española de Cardiología 58(10):1155-1161 (2005).
Patent Examination Report No. 1, Australian Patent Application No. 2013204539, dated Jan. 17, 2014.
Perrier et al., "D-dimer testing for suspected pulmonary embolism in outpatients," Am. J. Respir. Crit. Care Med., 156(2):492-496 (1997).
Potter et al., Mutations in the murine fitness 1 gene result in defective hematopoiesis. Blood. Sep. 1, 1997;90(5):1850-7.
Richards et al., "Plasma N-terminal pro-brain natriuretic peptide and adrenomedullin: new neurohormonal predictors of left ventricular function and prognosis after myocardial infarction," Circulation, 97:1921-1929 (1998) (cited in 003CA OA Oct. 31, 2010).

Ridker et al., "Inflammation, Aspirin, and the Risk of Cardiovascular Disease in Apparently Healthy Men," New England J. Med., 336:973-979 (1997).
Ridker et al., "C-Reactive Protein and Other Markers of Inflammation in the Prediction of Cardiovascular Disease in Women," England J. Medicine, May 2000, 324: 836-843.
Rohde et al., "Circulating Cell Adhesion Molecules Are Correlated With Ultrasound-Based Assessment of Carotid Atherosclerosis," Arterial Sclerotic Vasc. Biol., 18:1765-1770 (1998).
Rohde et al., "Plasma Concentrations of Interleukin-6 and Abdominal Aortic Diameter Among Subjects Without Aortic Dilatation," Arterial Sclerotic Vasc. Biol., 19:1695-1699 (1999).
Roig et al., Serum interleukin-6 in congestive heart failure secondary to idiopathic dilated cardiomyopathy. Am J Cardiol. Sep. 1, 1998;82(5):688-90, A8.
Sabatine et al., "Multimarker approach to risk stratification in non-ST elevation acute coronary syndromes: simultaneous assessment of troponin I, C-reactive protein, and B-type natriuretic peptide," Circulation, 105(15):1760-1763 (2002).
Saccani et al., Divergent effects of LPS on expression of IL-1 receptor family members in mononuclear phagocytes in vitro and in vivo. Cytokine. Oct. 1998;10(10):773-80.
Schaffer et al., Device for the application of a dynamic biaxially uniform and isotropic strain to a flexible cell culture membrane. J Orthop Res. Sep. 1994;12(5):709-19.
Schmitz et al., "IL-33, an interleukin-1-like cytokine that signals via the IL-1 receptor-related protein ST2 and induces T helper type 2-associated cytokines," Immunity, 23(5):479-490 (2005).
Second Office Action; CN 201110387886.6; dated Dec. 19, 2013 (with English translation).
Selvais et al., J Card Fail, Sep. 2000; 6(3):201-7. (Abstract Only).
Shimpo et al., "Serum levels of the interleukin-1 receptor family member ST2 predict mortality and clinical outcome in acute myocardial infarction" Circulation, 109(18):2186-2190 (2004).
Silver et al., Cong. Heart Fail., 10(5 suppl. 3) :1-30 (2004).
Singapore Office Action in Singapore Application No. 11201501271T, 12 pages, dated Aug. 6, 2016.
Strunk et al., "Impact of the history of congestive heart failure on the utility of B-type natriuretic peptide in the emergency diagnosis of heart failure: results from the Breathing Not Properly Multinational Study," Am. J. Med., 119(1):69 e1-11 (2006).
Supplementary European Search Report and Search Opinion for European Application No. EP 09731842, search and opinion dated Apr. 1, 2011, search completed Feb. 28, 2011.
Sussman et al., Dance band on the Titanic: biomechanical signaling in cardiac hypertrophy. Circ Res. Nov. 15, 2002;91(10):888-98.
Sutton et al., Left ventricular remodeling after myocardial infarction: pathophysiology and therapy. Circulation. Jun. 27, 2000;101(25):2981-8.
Svensson et al., "Prognostic value of biochemical markers, 12-lead ECG and patient characteristics amongst patients c a l l i ng for an ambulance due to a suspected acute coronary syndrome," Journal of Internal Medicine, 255(4):469-477 (2004).
Tajima et al., "The increase in serum soluble ST2 protein upon acute exacerbation of idiopathic pulmonary fibrosis," Chest, 124(4):1206-1214 (2003). (cited in 0003CA Aug. 31, 2010).
Tang Z, et al. Gene Expression profiling during the transition to failure in TNF-α over-expressing mice demonstrates the development of autoimmune myocarditis. Journal of Molecular and Cellular Cardiology 2004; 36:515-30.
Tominaga et al., [ST2 gene: a gene that is induced by growth stimulation and encoding a product highly similar to the interleukin 1 receptors] Seikagaku. May 1995;67(5):356-64. Review. Japanese with translation.
Tominaga et al., "Nucleotide sequence of a complementary DNA for human ST2," Biochim. Biophys. Acta., 1171:215-218 (1992). (Abstract Only).
Tominaga et al., The existence of a growth-specific DNA binding factor for the promoter region of mouse ST2 gene. FEBS Lett. Nov. 14, 1994;354(3):311-4.

(56) References Cited

OTHER PUBLICATIONS

Tominaga, FEBS Lett., "A putative protein of a growth specific cDNA from BALB/c-3T3 cells is highly similar to the extracellular portion of mouse interleukin 1 receptor," FEBS Lett., 258:301-304 (1989).

Townsend et al., T1/ST2-deficient mice demonstrate the importance of T1/ST2 in developing primary T helper cell type 2 responses. J Exp Med. Mar. 20, 2000;191(6):1069-76.

Tsuchiya et al., "Th1, Th2 and activated T-cell marker and clinical prognosis in peripheral T-cell lymphoma unspecified comparison AILD, ALCL, lymphoblastic lymphoma and ATLL," Blood, 103:236-241 (2004).

Tsutamoto et al., Interleukin-6 spillover in the peripheral circulation increases with the severity of heart failure, and the high plasma level of interleukin-6 is an important prognostic predictor in patients with congestive heart failure. J Am Coll Cardiol. Feb. 1998;31(2):391-8.

Tung et al., "Utility of B-type natriuretic peptide for the evaluation of intensive care unit shock," Crit. Care Med., 32(8):1643-1647 (2004).

Van Kimmenade et al., Utility of amino-terminal pro-brain natriuretic peptide, galectin-3, and apelin for the evaluation of patients with acute heart failure. J Am Coll Cardiol. Sep. 19, 2006;48(6):1217-24.

Vidal et al., Prognostic Value of Cytokines and Neurohormones in Severe Heart Failure, Rev Esp Cardiol 2002; 55(5):481-6.

Wang et al., "Expression of Interleukin-1β, Interleukin-1 Receptor, and Interleukin-1 Receptor Antagonist mRNA in Rat Carotid Artery after Balloon Angioplasty," Biochem. Biophyl. Res. Comm., 271:138-143 (2000).

Weinberg et al., "Expression and regulation of ST2, an interleukin-1 receptor family member, in cardiomyocytes and myocardial infarction," Circulation, 106(23):2961-2966 (2002).

Weinberg et al., "Identification of serum soluble ST2 receptor as a novel heart failure biomarker," Circulation, 107(5):721-726 (2003).

Yamaoka et al., Anti-inflammatory cytokine profile in human heart failure: behavior of interleukin-10 in association with tumor necrosis factor-alpha. Jpn Circ J. Dec. 1999;63(12):951-6.

Zebrack et al., Usefulness of high-sensitivity C-reactive protein in predicting long-term risk of death or acute myocardial infarction in patients with unstable or stable angina pectoris or acute myocardial infarction. Am J Cardiol. Jan. 15, 2002;89(2):145-9.

Extended European Search Report in Application No. 18166387.3, dated Jun. 15, 2018, 5 pages.

Office Action in Chinese Application No. 201380054795.8, dated Oct. 22, 2018, 11 pages (English translation).

Office Action in Japanese Application No. 2017-162932, dated Jun. 27, 2018, 8 pages (with English Translation).

Office Action in Japanese Application No. 2017-178945, dated Jul. 5, 2018, 8 pages (with English Translation).

Office Action in Russian Application No. 2015110054, dated Jun. 7, 2018, 16 pages (with English translation).

\* cited by examiner

Fig. 1
Summary Stats
1 Year Mortality

| Variable | Outcome=0 Median [IQR] | Missing | Outcome=1 Median [IQR] | Missing | KW Test P Value | sHR(Raw) Est [95% CI] | log-rank p | sHR(ln) Est [95% CI] | log-rank p | AuROC | Most Gaussian |
|---|---|---|---|---|---|---|---|---|---|---|---|
| NTproBNP_pg_ml | 1210[458.5-2866] | 0 | 2775.5[1682-5774] | 0 | <0.001 | 1.24 [1.12-1.38] | <0.001 | 2.04 [1.63-2.55] | <0.001 | 0.702 | ln |
| cTnT1 | 21.09[9.74-37.44] | 13 | 41.16[29.81-67.44] | 2 | <0.001 | 1.21 [1.11-1.33] | <0.001 | 2.09 [1.7-2.56] | <0.001 | 0.742 | ln |
| Creatinine | 1.46[1.17-1.97] | 3 | 1.68[1.31-2.29] | 0 | 0.002 | 1.1 [0.96-1.25] | 0.18 | 1.26 [1.06-1.51] | 0.009 | 0.602 | ln |
| eGFR | 42.13[29.36-58.99] | 13 | 29.02[21.96-45.73] | 2 | <0.001 | 0.52 [0.39-0.69] | <0.001 | 0.66 [0.55-0.78] | <0.001 | 0.663 | ln |
| SBP | 125[110-140] | 9 | 120[103.75-140] | 2 | 0.051 | 0.81 [0.65-1.02] | 0.075 | 0.8 [0.64-0.99] | 0.044 | 0.565 | ln |
| DBP | 70[63-80] | 9 | 65.5[60-75] | 2 | 0.004 | 0.7 [0.55-0.89] | 0.004 | 0.7 [0.56-0.88] | 0.002 | 0.596 | ln |
| HGB_g_dl | 13[11.8-14.3] | 0 | 11.95[10.72-13.28] | 0 | <0.001 | 0.63 [0.52-0.76] | <0.001 | 0.74 [0.65-0.83] | <0.001 | 0.656 | Raw |
| Age_Yr | 69.6[59.6-76.4] | 0 | 77.2[68.7-83.3] | 0 | <0.001 | 2.23 [1.68-2.96] | <0.001 | 2.4 [1.71-3.37] | <0.001 | 0.695 | Raw |
| ST2_ng_ml | 37.1[30.4-48.9] | 0 | 53.3[38.45-89.1] | 0 | <0.001 | 1.39 [1.27-1.52] | <0.001 | 1.82 [1.56-2.13] | <0.001 | 0.705 | ln |
| LVEF | 34[26-43] | 0 | 35[25.25-43] | 0 | 0.494 | 1.08 [0.88-1.33] | 0.456 | 1.1 [0.89-1.36] | 0.386 | 0.522 | ln |
| BMI | 27[24.5-30.7] | 13 | 25.15[22.8-27.92] | 2 | <0.001 | 0.61 [0.47-0.8] | <0.001 | 0.64 [0.51-0.8] | <0.001 | 0.625 | ln |
| NYHA | 1=64,2=545,3=188,4=8 | 0 | 1=1,2=39,3=44,4=2 | 0 | <0.001 | | <0.001 | | | | |
| Ethnicity | 1=800;2=5 | 0 | 1=86 | 0 | 1 | 0 [0-Inf] | 0.475 | | | | |
| Sex | 0=230;1=575 | 0 | 0=23;1=63 | 0 | 0.802 | 1.1 [0.68-1.77] | 0.707 | | | | |
| CAD | 0=327;1=478 | 0 | 0=39;1=47 | 0 | 0.421 | 0.82 [0.54-1.26] | 0.362 | | | | |
| Diabetes | 0=523;1=282 | 0 | 0=47;1=39 | 0 | 0.076 | 1.5 [0.98-2.29] | 0.061 | | | | |
| HTN | 0=316;1=489 | 0 | 0=31;1=55 | 0 | 0.642 | 1.12 [0.72-1.74] | 0.616 | | | | |

Fig. 2
Summary Stats
Study Mortality

| Variable | Outcome=0 Median [IQR] | Missing | Outcome=1 Median [IQR] | Missing | KW Test P Value | sHR(Raw) Est [95% CI] | log-rank p | sHR(ln) Est [95% CI] | log-rank p | AuROC | Most Gaussian |
|---|---|---|---|---|---|---|---|---|---|---|---|
| NTproBNP_pg_ml | 969.65[364.12-2313.5] | 0 | 2233[922.4-5174] | 0 | <0.001 | 1.27 [1.19-1.35] | <0.001 | 2 [1.77-2.25] | <0.001 | 0.684 | ln |
| cTnT1 | 15.65[7.92-30.78] | 7 | 34.18[20.81-53.64] | 8 | <0.001 | 1.21 [1.15-1.28] | <0.001 | 2.01 [1.8-2.24] | <0.001 | 0.725 | ln |
| Creatinine | 1.37[1.12-1.86] | 3 | 1.67[1.33-2.37] | 0 | <0.001 | 1.13 [1.06-1.21] | <0.001 | 1.36 [1.24-1.49] | <0.001 | 0.643 | ln |
| eGFR | 47.73[32.75-65.07] | 4 | 32.45[22.55-44.32] | 11 | <0.001 | 0.47 [0.4-0.54] | <0.001 | 0.63 [0.57-0.69] | <0.001 | 0.711 | ln |
| SBP | 123[110-140] | 5 | 125[110-145] | 6 | 0.409 | 0.99 [0.89-1.11] | 0.879 | 0.99 [0.88-1.1] | 0.817 | 0.517 | ln |
| DBP | 70[65-80] | 5 | 70[60-78] | 6 | <0.001 | 0.82 [0.73-0.92] | 0.001 | 0.81 [0.72-0.91] | <0.001 | 0.571 | ln |
| HGB_g_dl | 13.2[12-14.5] | 0 | 12.1[11.1-13.6] | 0 | <0.001 | 0.68 [0.62-0.75] | <0.001 | 0.78 [0.73-0.83] | <0.001 | 0.654 | Raw |
| Age_Yr | 66.05[56.58-74.32] | 0 | 75.5[69.6-80.85] | 0 | <0.001 | 2.26 [1.95-2.61] | <0.001 | 2.5 [2.1-2.97] | <0.001 | 0.737 | Raw |
| ST2_ng_ml | 35.45[29.37-45.4] | 0 | 44.7[34-61.1] | 0 | <0.001 | 1.29 [1.22-1.37] | <0.001 | 1.62 [1.48-1.77] | <0.001 | 0.662 | ln |
| LVEF | 34[26-42.25] | 0 | 34[25-44] | 0 | 0.865 | 0.98 [0.88-1.09] | 0.705 | 0.95 [0.85-1.06] | 0.344 | 0.503 | ln |
| BMI | 27.1[24.7-30.7] | 5 | 26.4[23.6-29.8] | 10 | 0.005 | 0.79 [0.7-0.9] | <0.001 | 0.78 [0.7-0.88] | <0.001 | 0.558 | ln |
| NYHA | 1=60;2=418;3=91;4=3 | 0 | 1=5;2=166;3=141;4=7 | 0 | <0.001 | | <0.001 | | | | |
| Ethnicity | 1=567;2=5 | 0 | 1=319 | 0 | 0.166 | 0 [0-Inf] | 0.163 | | | | |
| Sex | 0=154;1=418 | 0 | 0=99;1=220 | 0 | 0.215 | 0.92 [0.73-1.17] | 0.494 | | | | |
| CAD | 0=242;1=330 | 0 | 0=124;1=195 | 0 | 0.321 | 1.07 [0.86-1.34] | 0.537 | | | | |
| Diabetes | 0=387;1=185 | 0 | 0=183;1=136 | 0 | 0.003 | 1.45 [1.16-1.8] | 0.001 | | | | |
| HTN | 0=237;1=335 | 0 | 0=110;1=209 | 0 | 0.045 | 1.3 [1.04-1.64] | 0.024 | | | | |

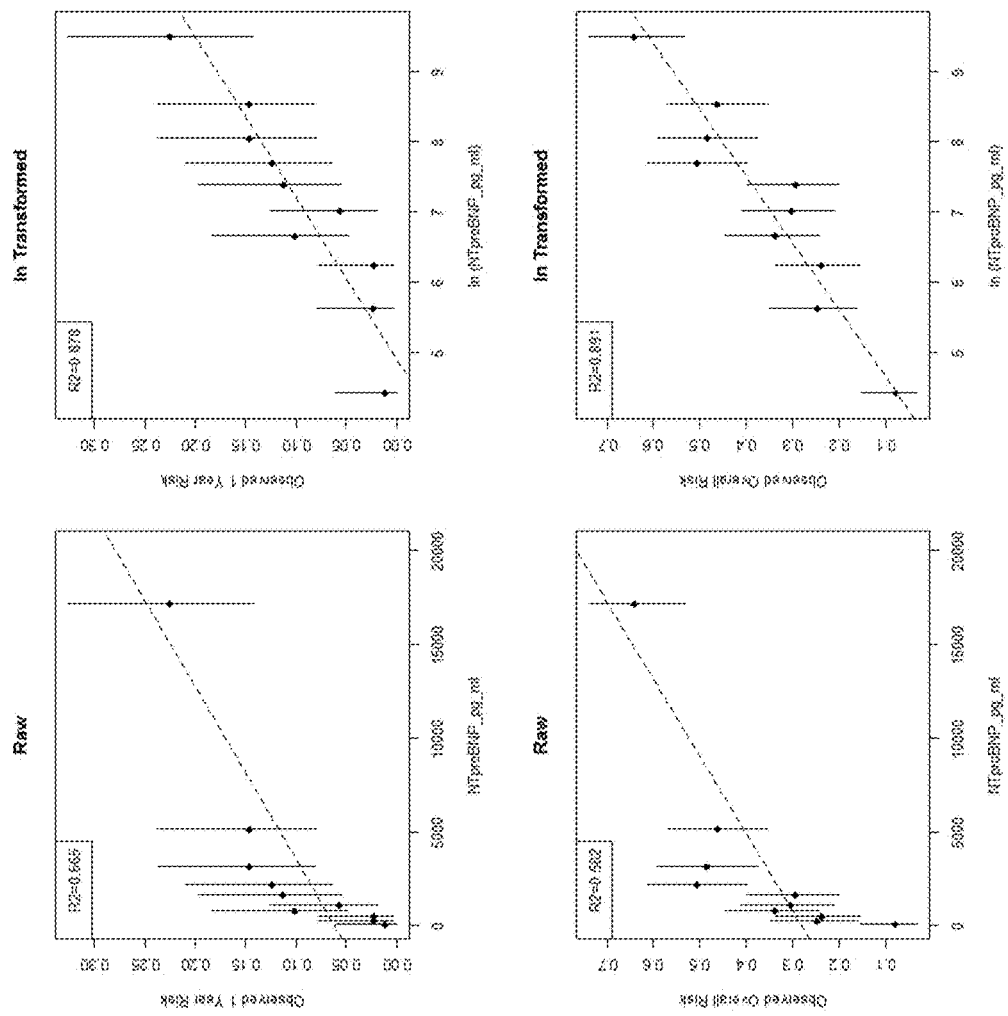

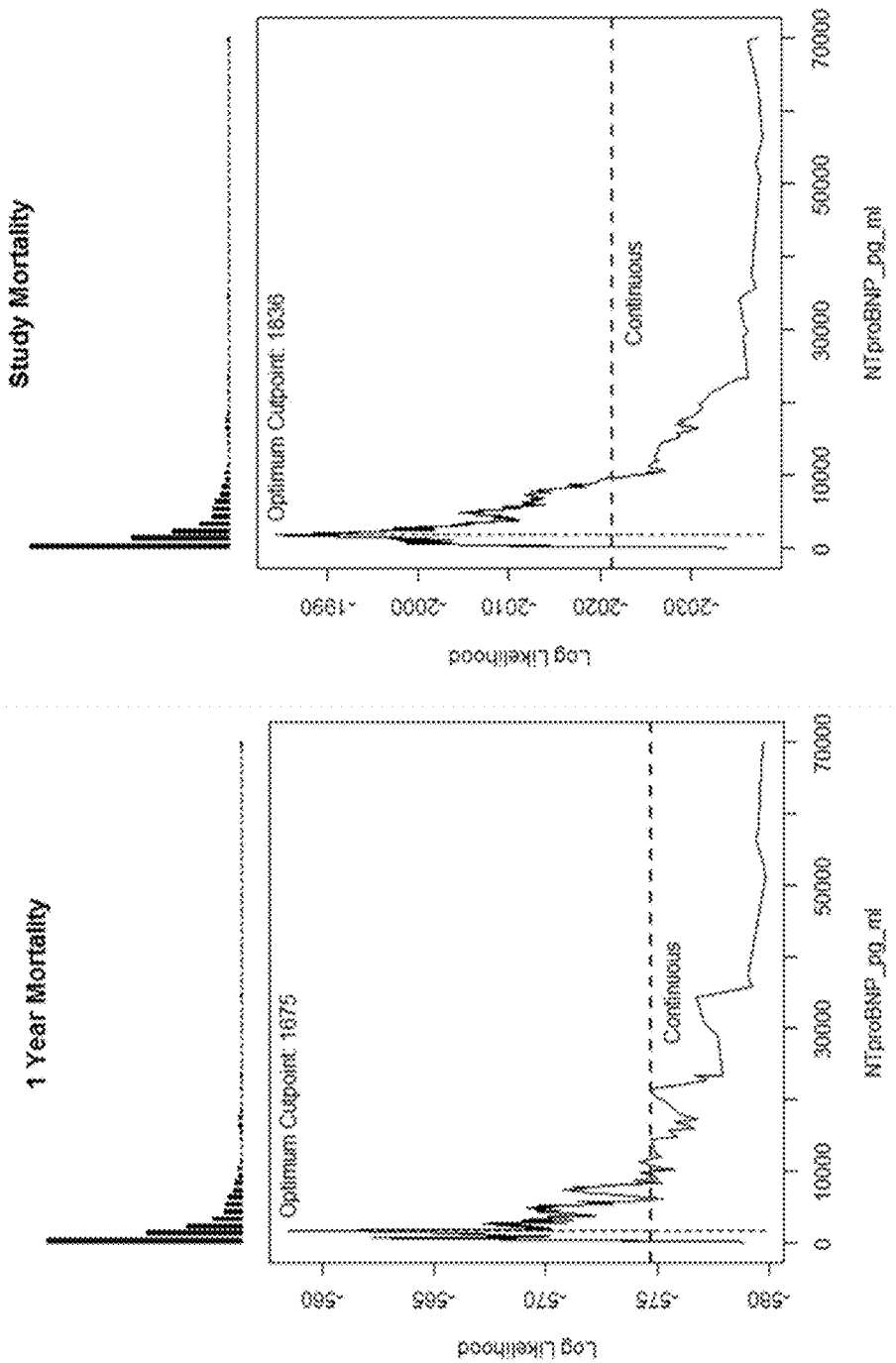
Fig. 4 Cut-Point Evaluation NT-proBNP

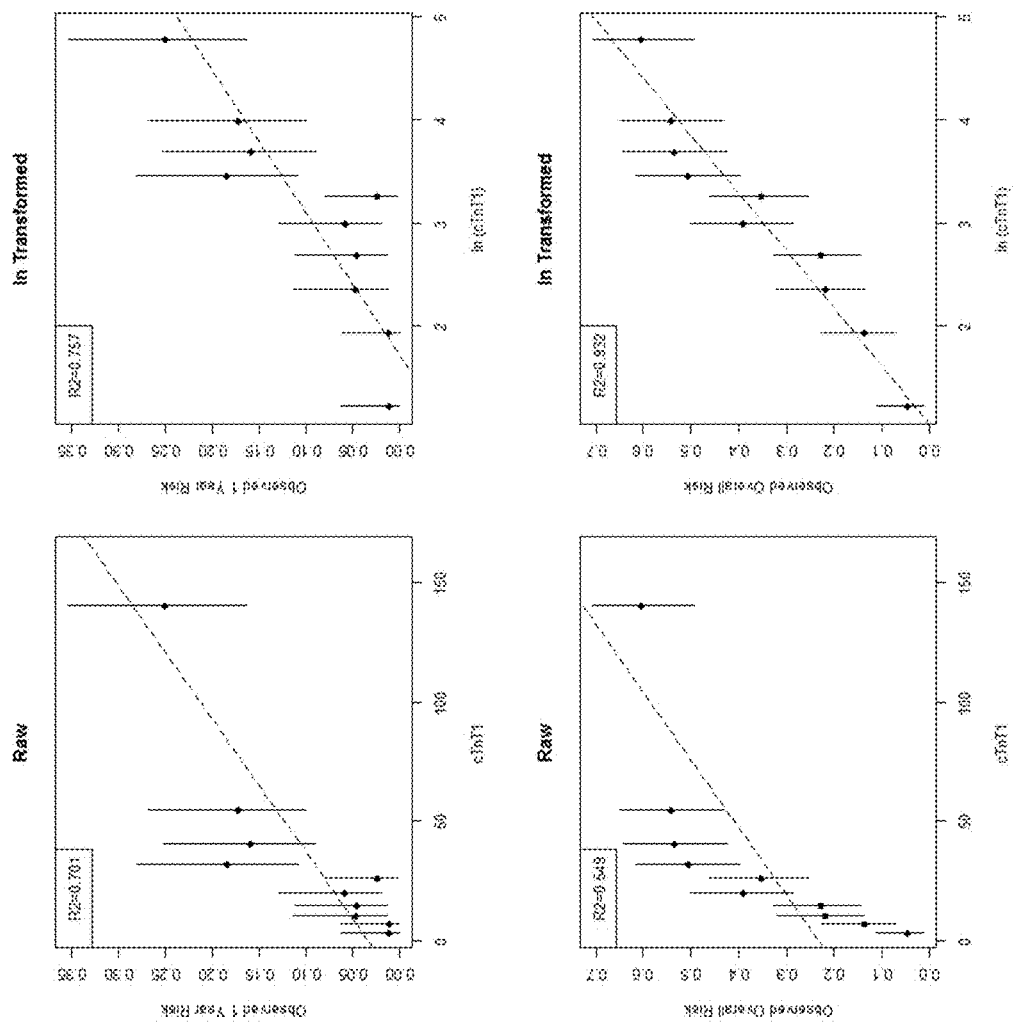
Fig. 5 Linearity Check: Troponin

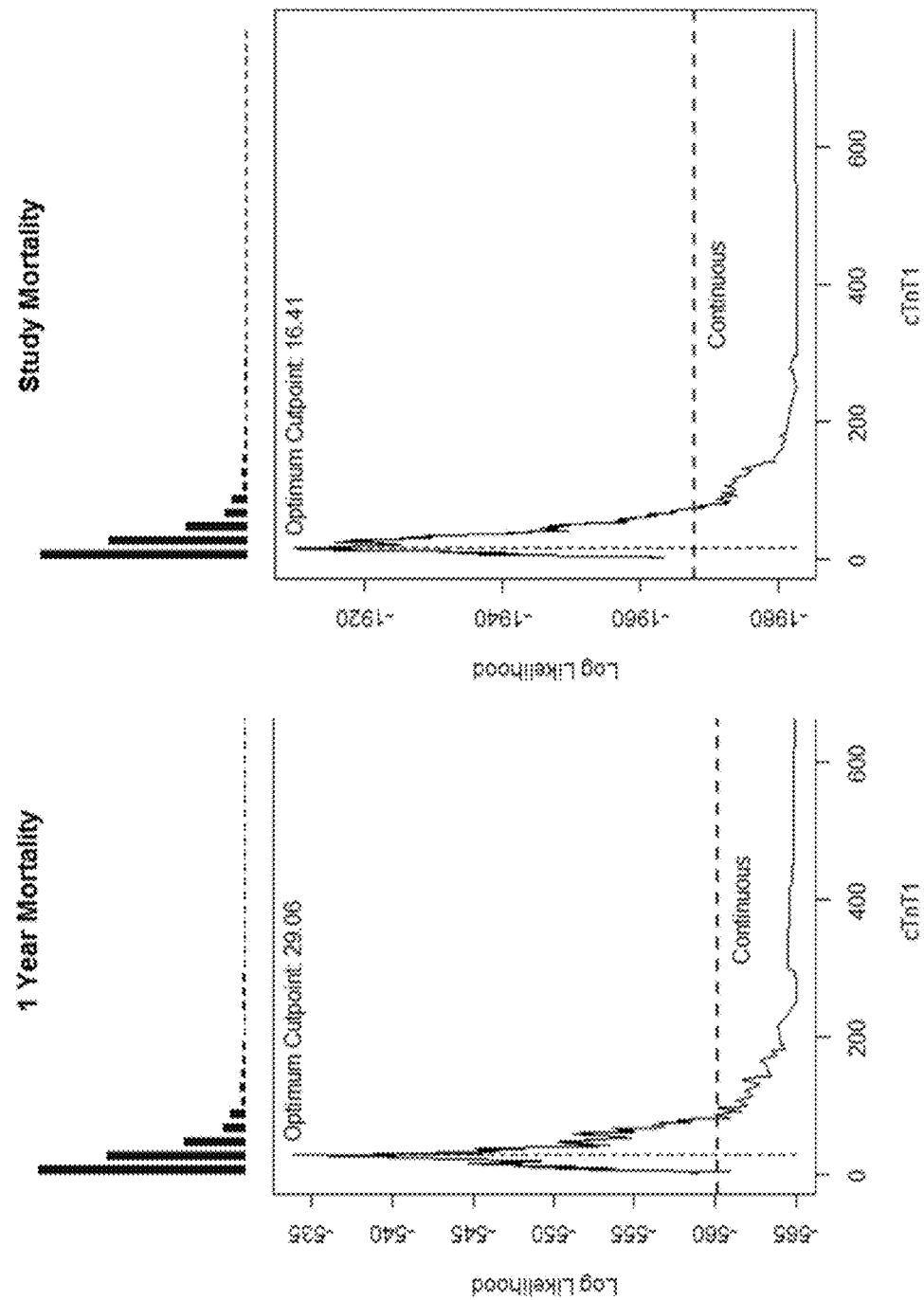
Fig. 6 Cut-Point Evaluation Troponin

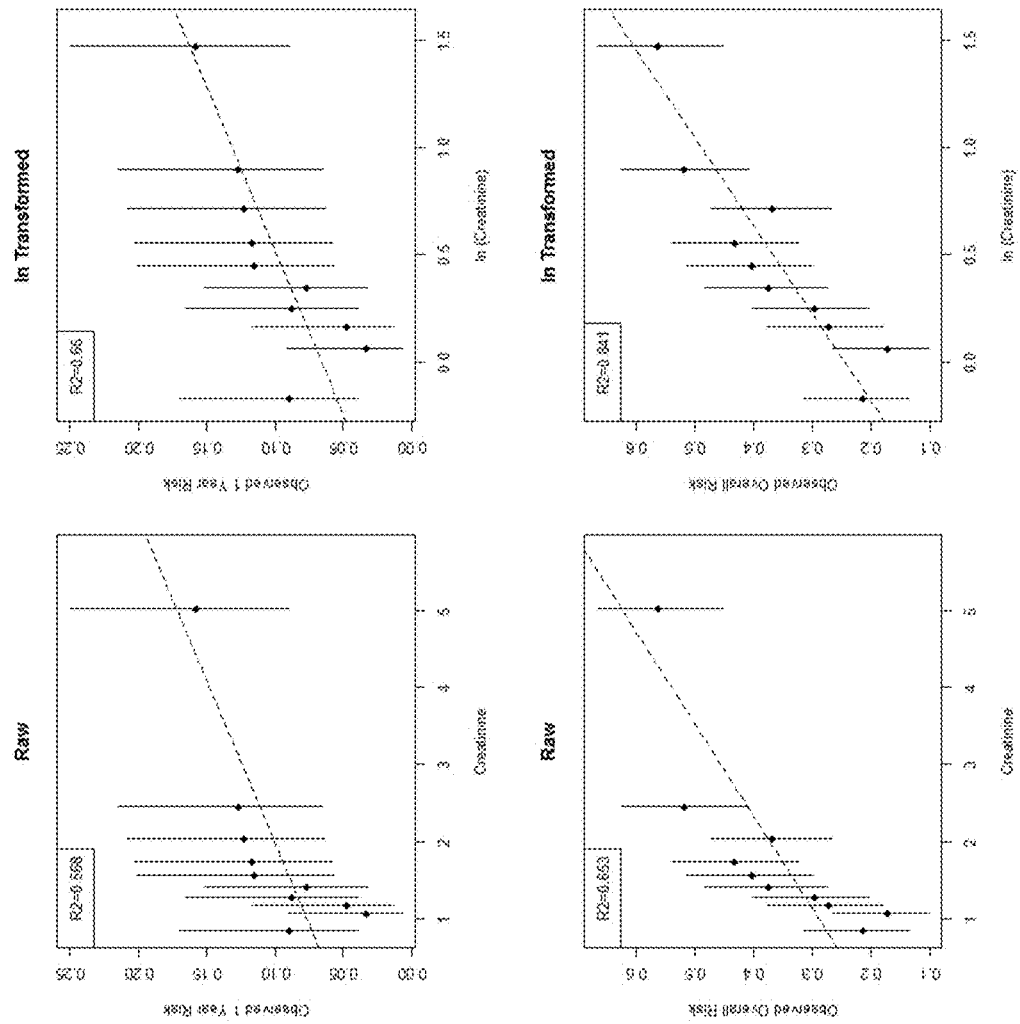
Fig. 7 Linearity Check: Creatinine

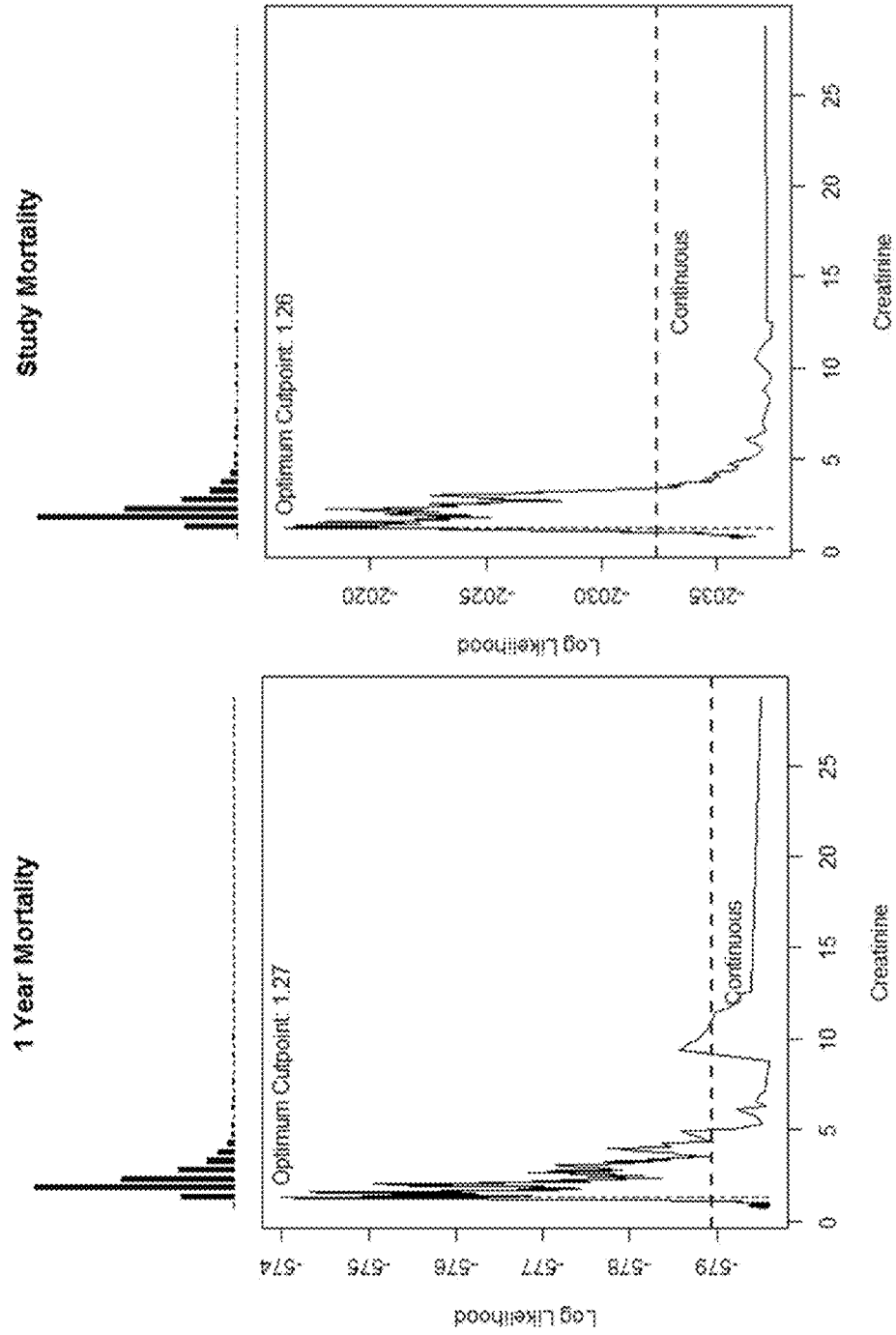
Fig. 8 Cut-Point Evaluation Creatinine

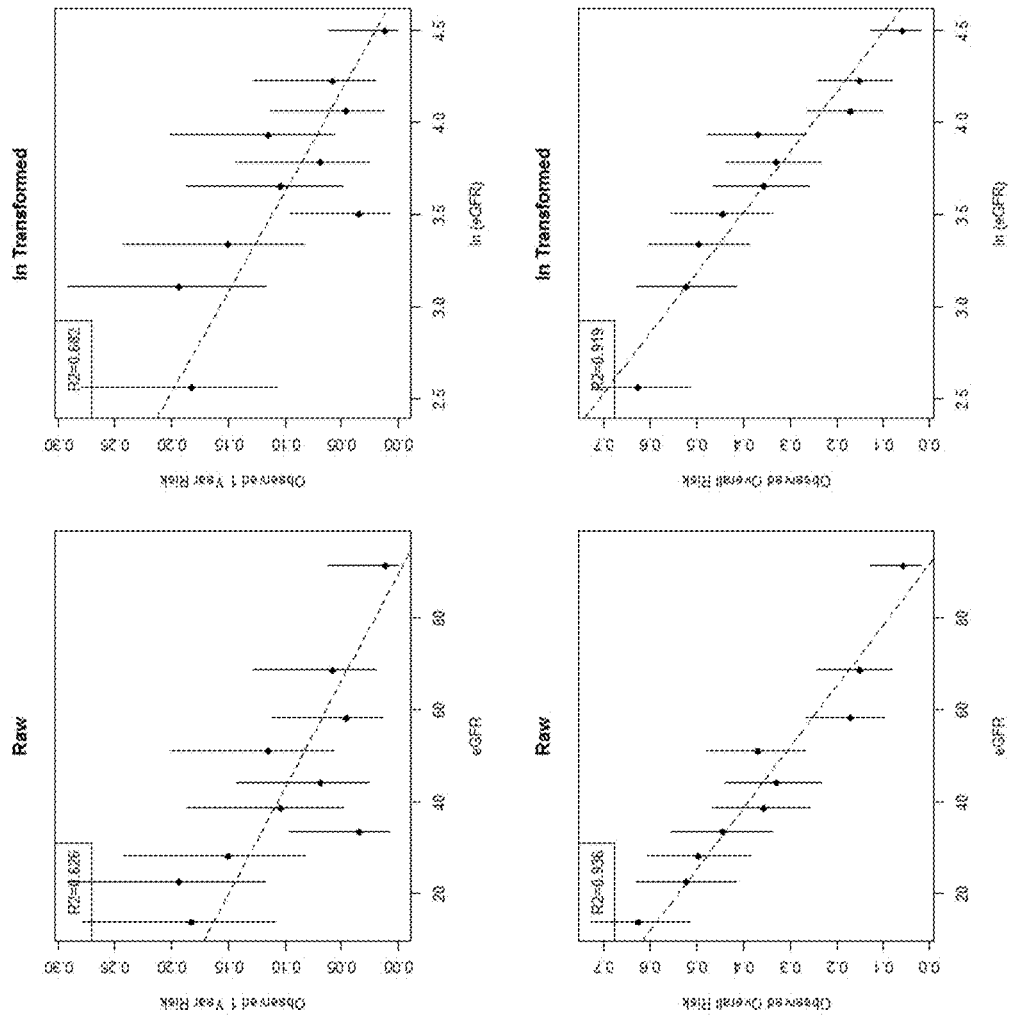
Fig. 9 Linearity Check: eGFR

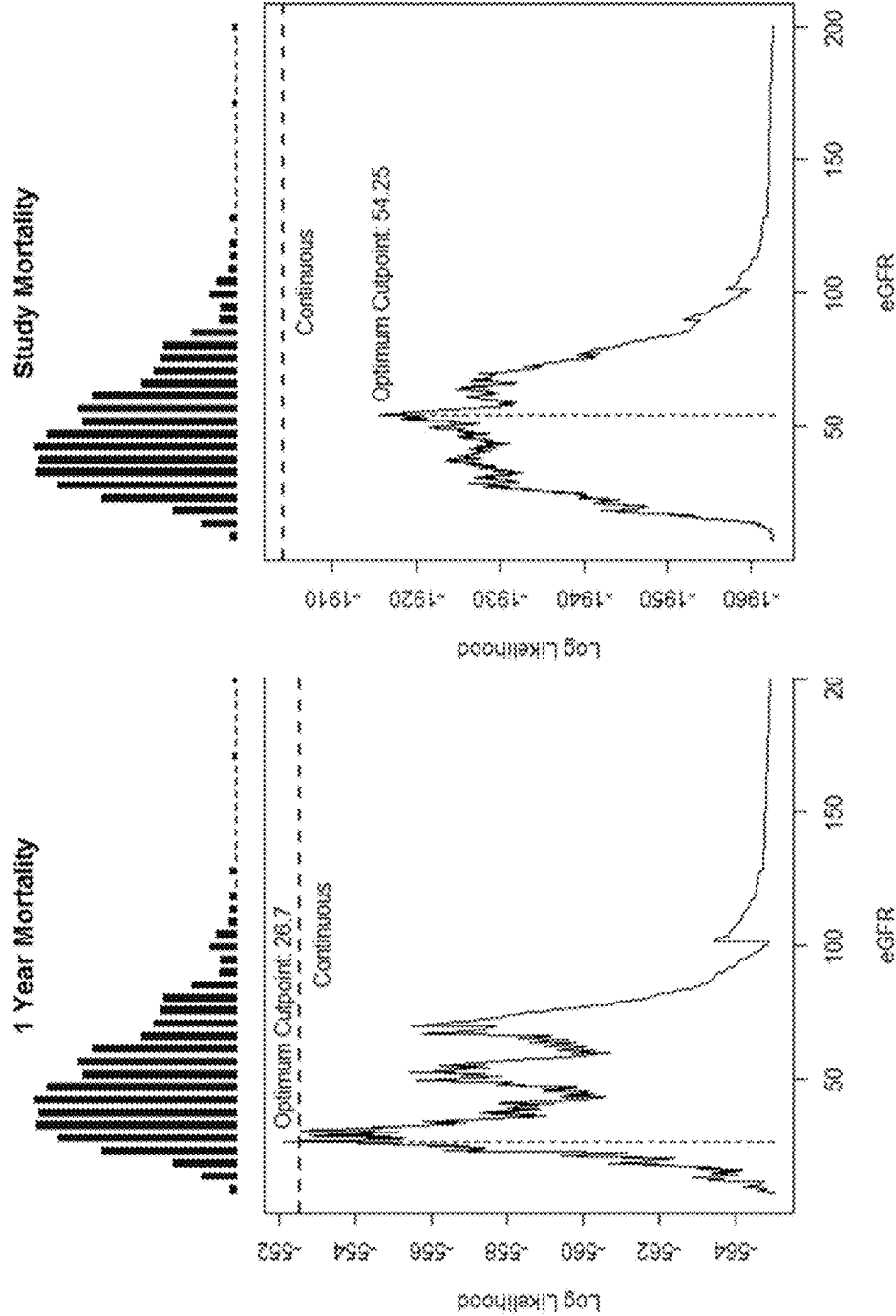
Fig. 10 Cut-Point Evaluation eGFR

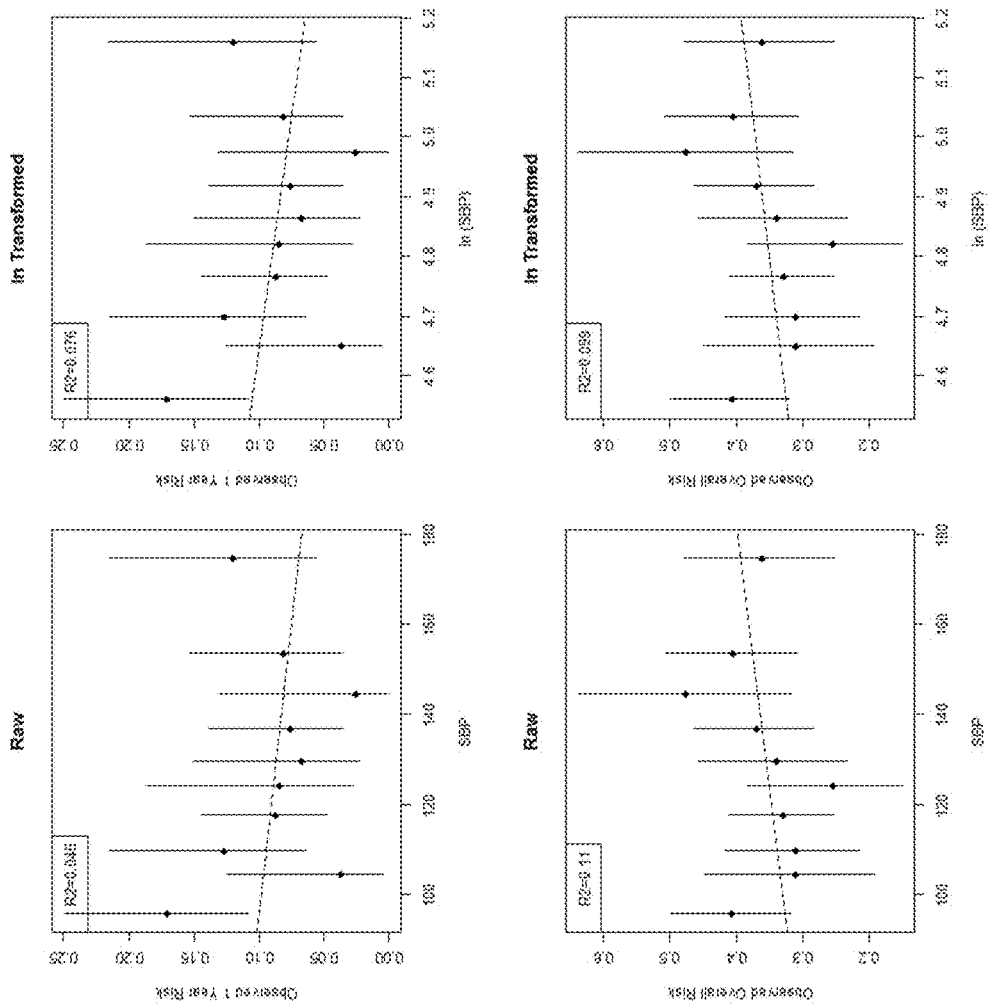
Fig. 11 Linearity Check: SBP

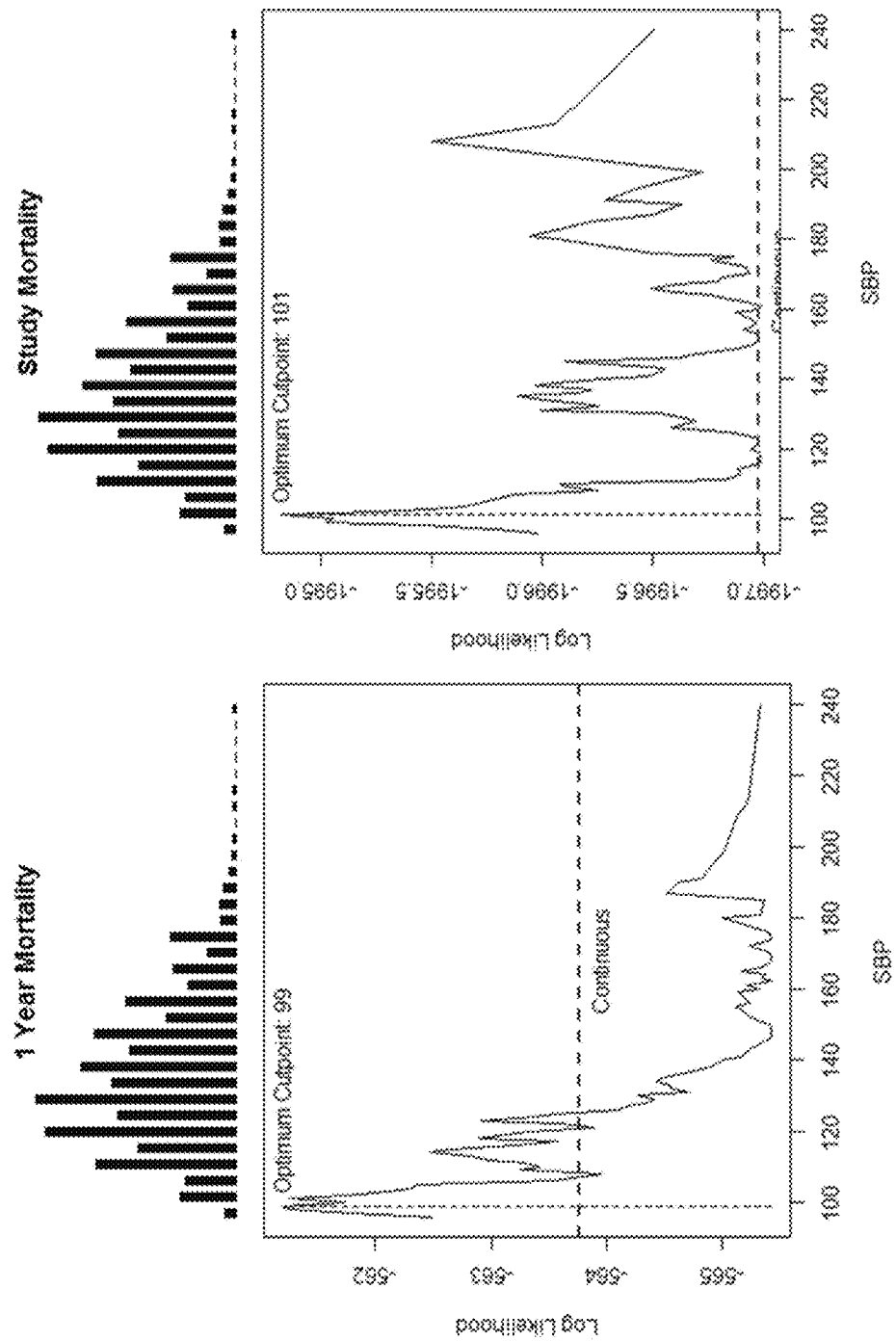
Fig. 12 Cut-Point Evaluation SBP

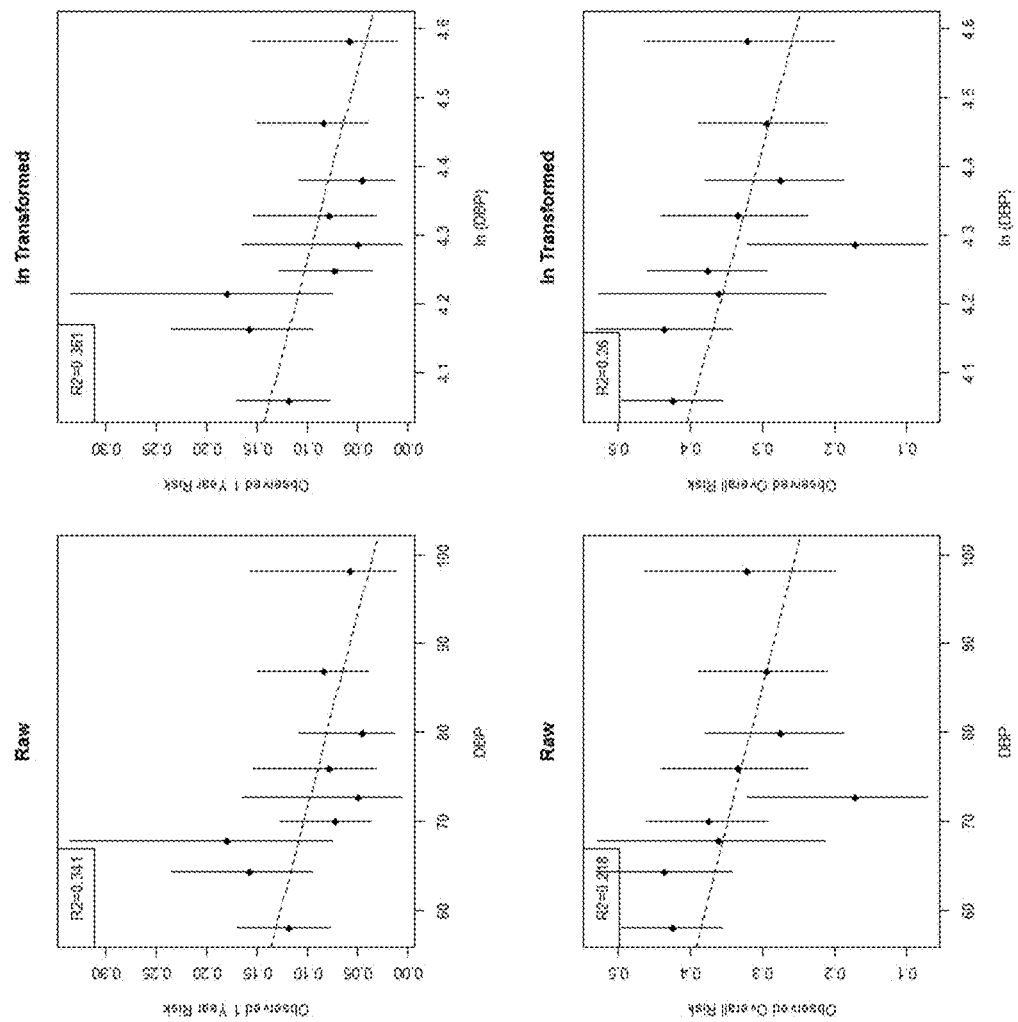
Fig. 13 Linearity Check: DBP

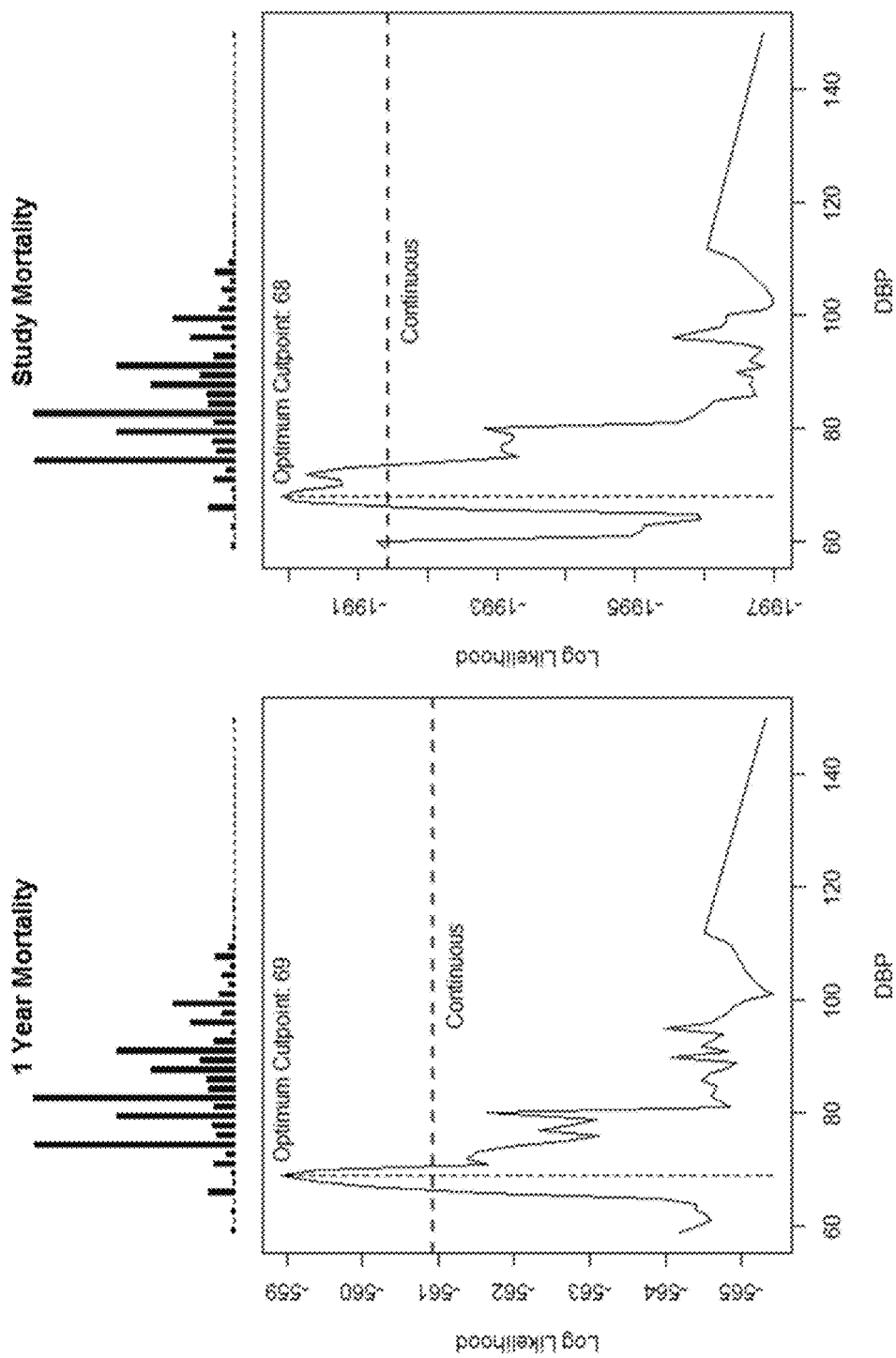

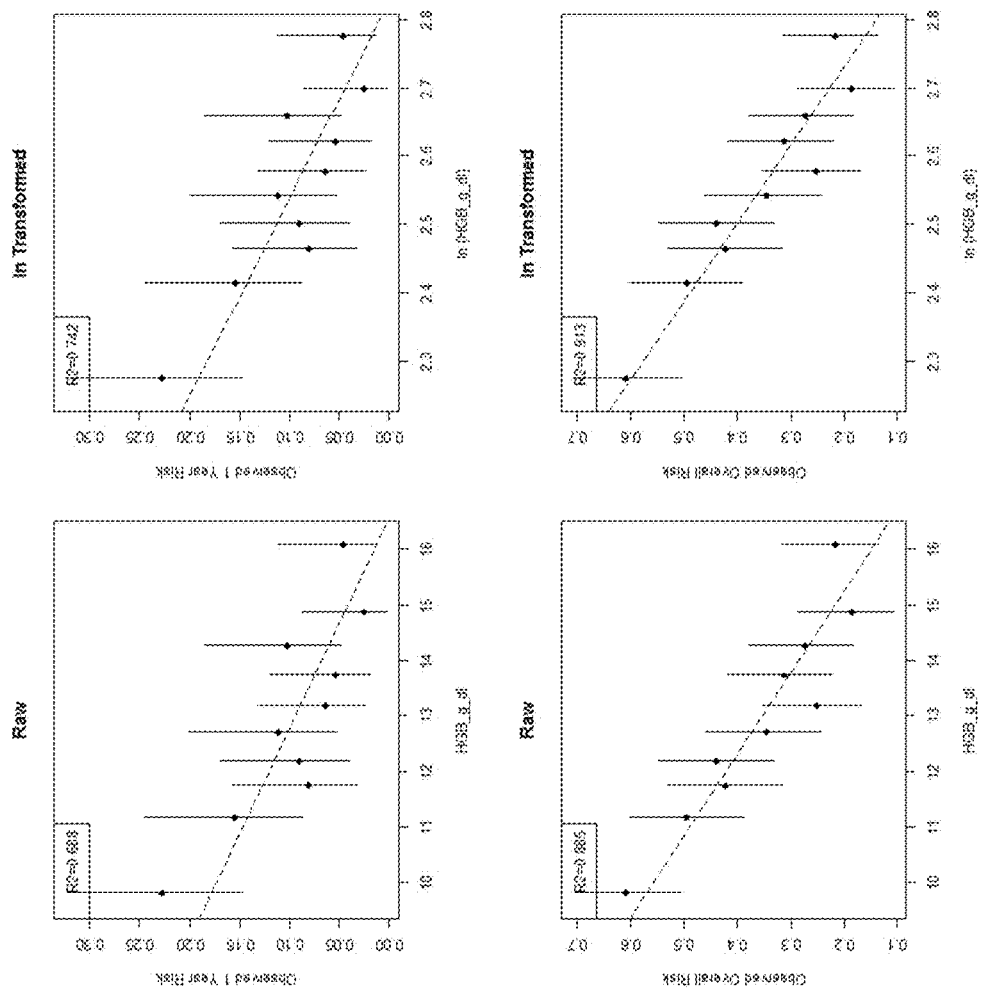
Fig. 15 Linearity Check: Hgb

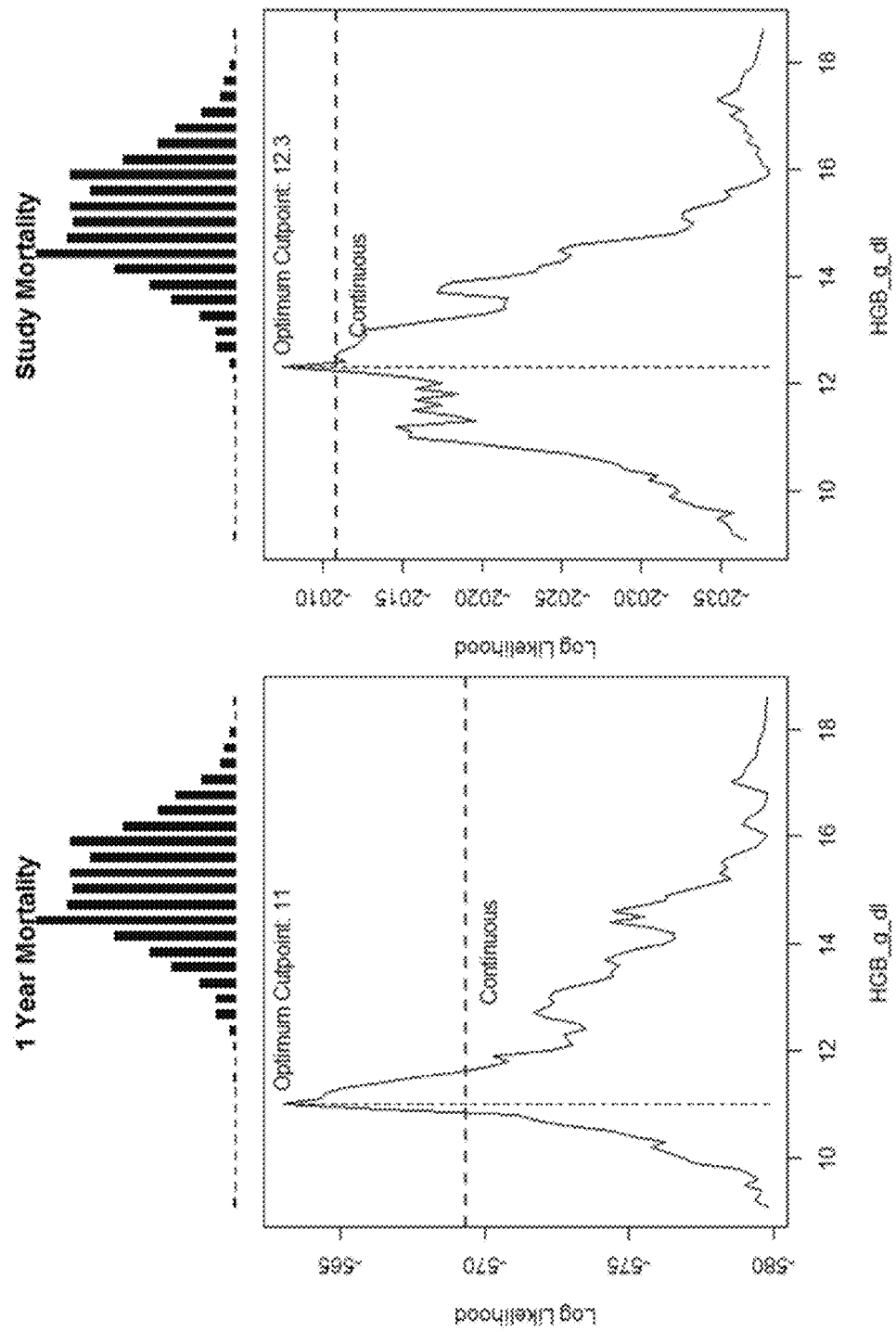

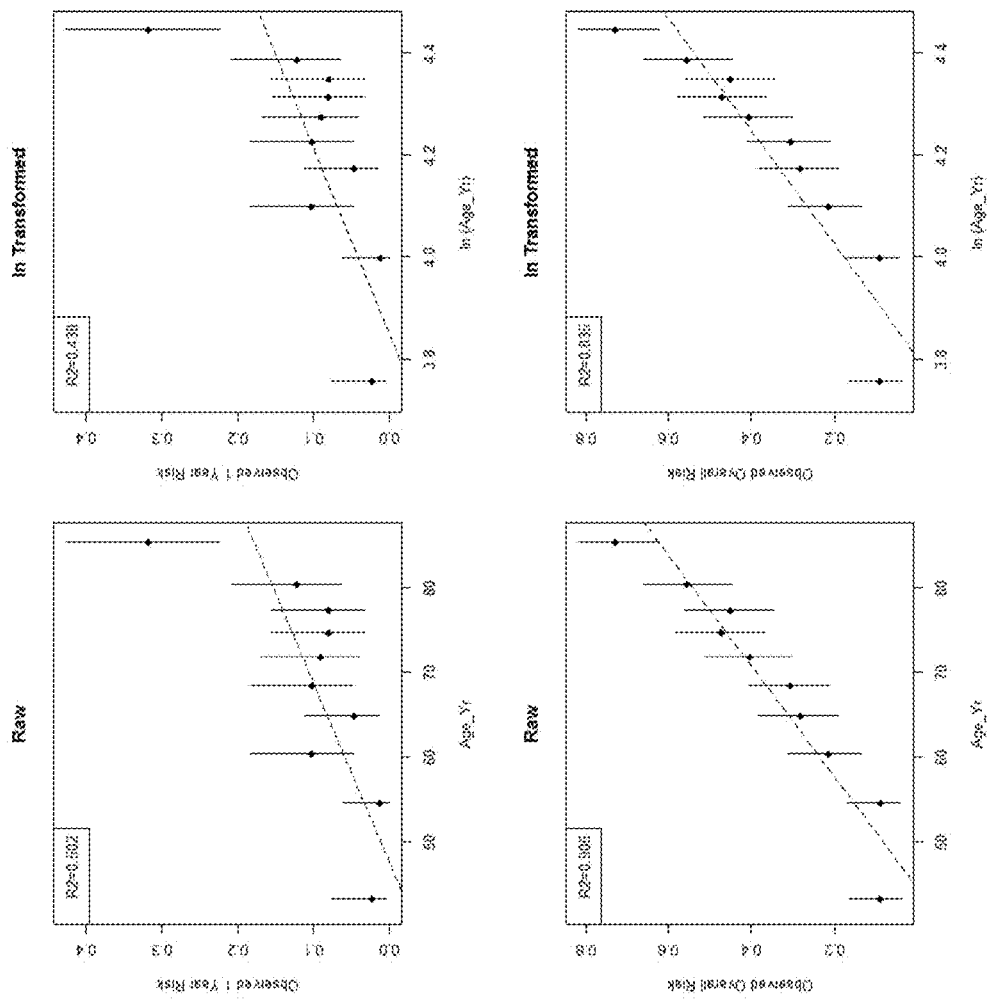
Fig. 17 Linearity Check: Age

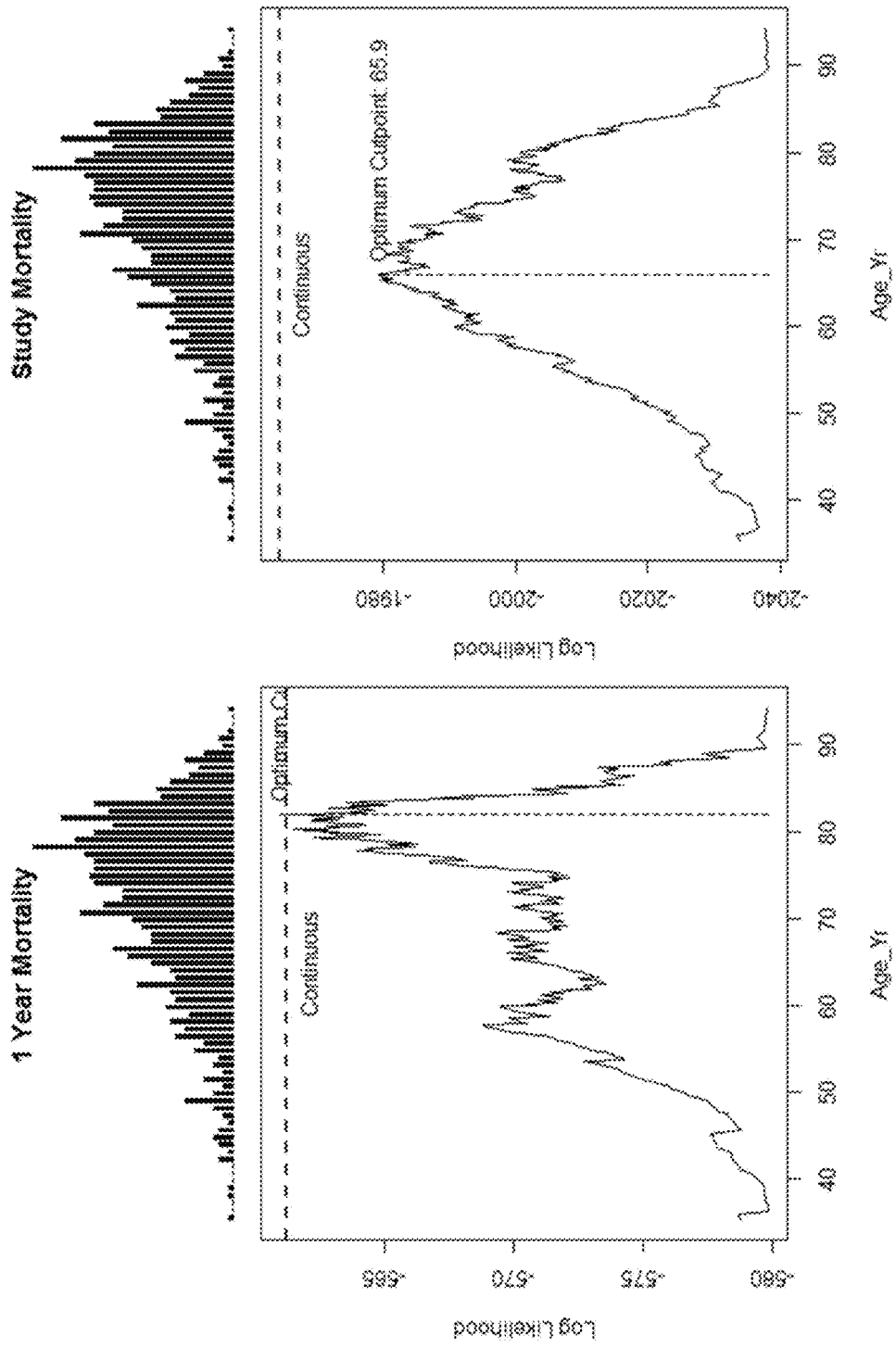
Fig. 18 Cut-Point Evaluation Age

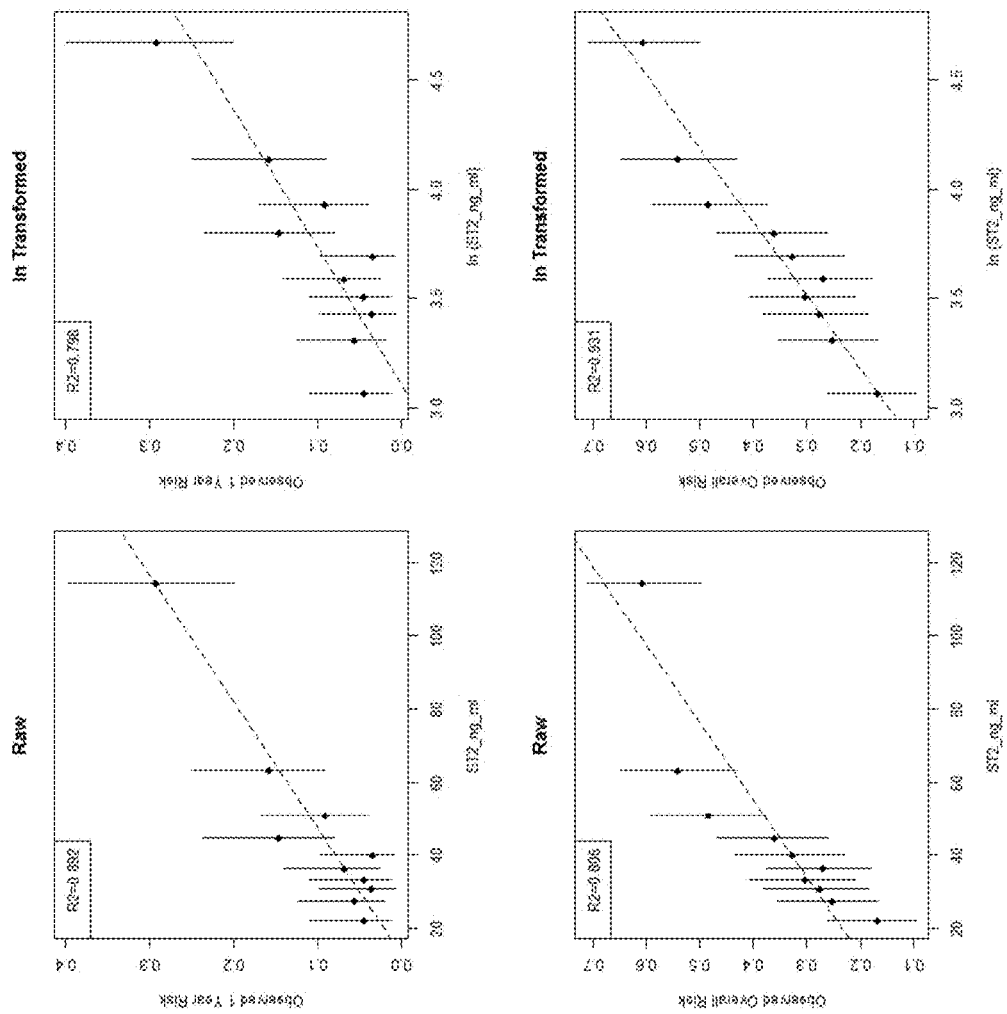
Fig. 19 Linearity Check: ST2

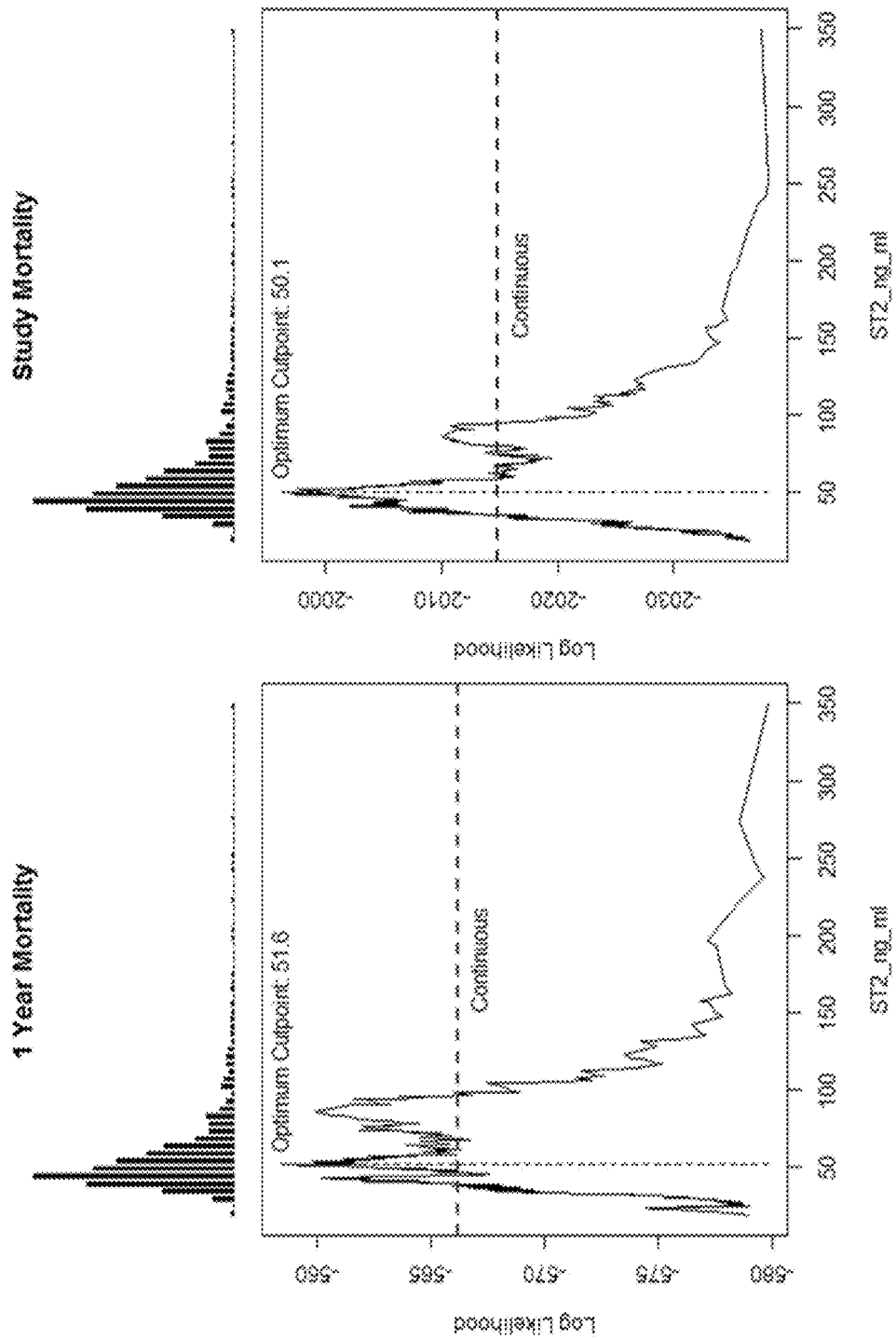
Fig. 20 Cut-Point Evaluation ST2

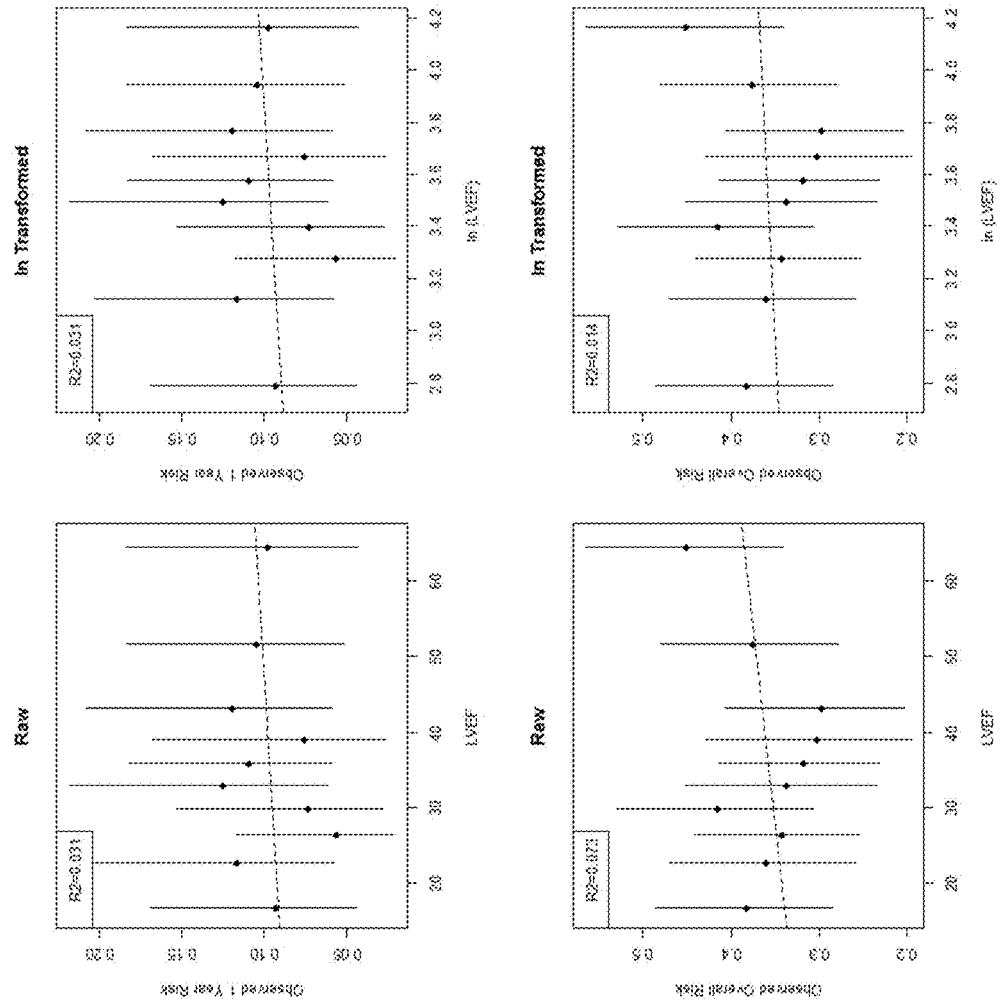
Fig. 21 Linearity Check: LVEF

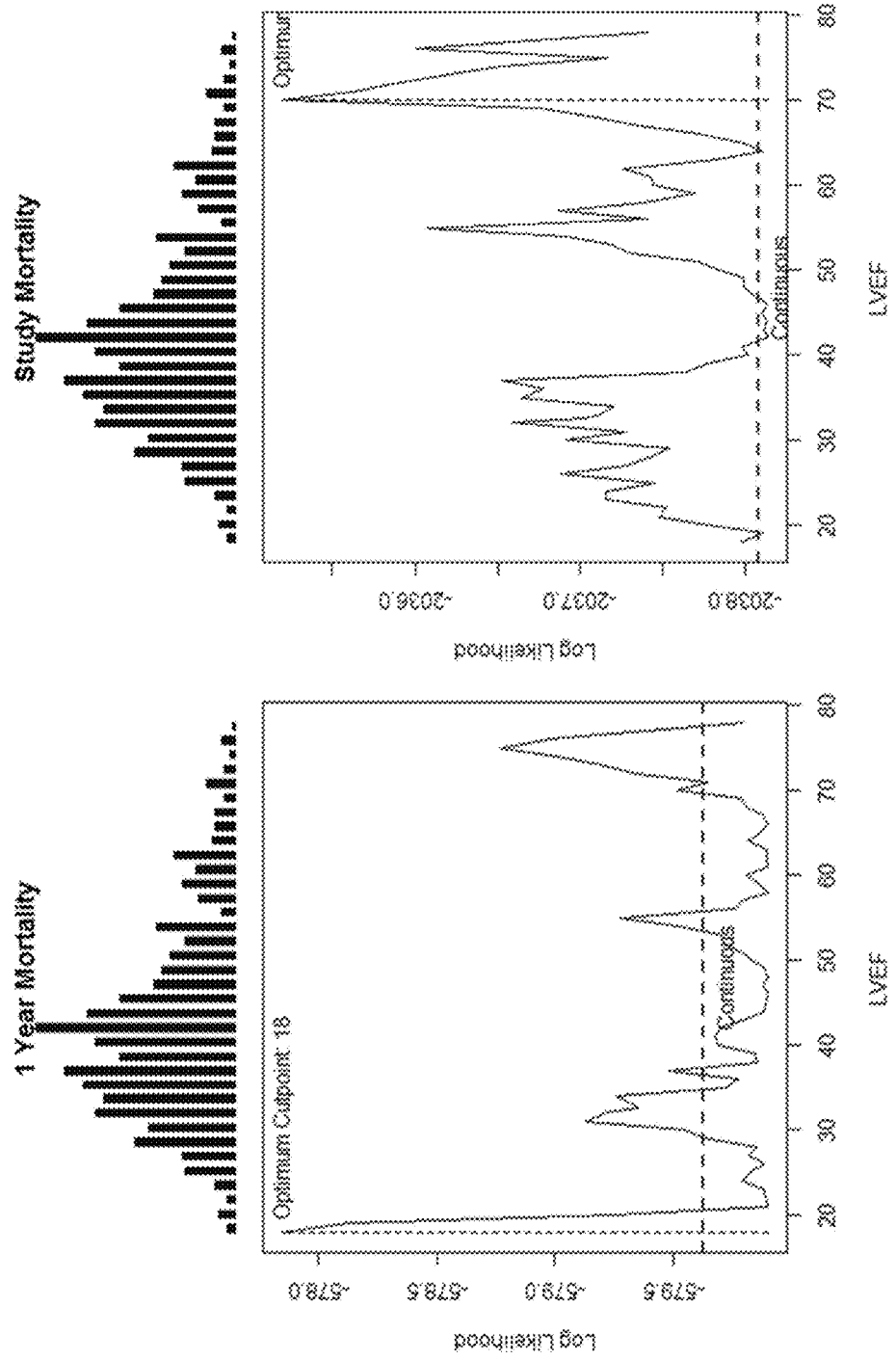
Fig. 22 Cut-Point Evaluation LVEF

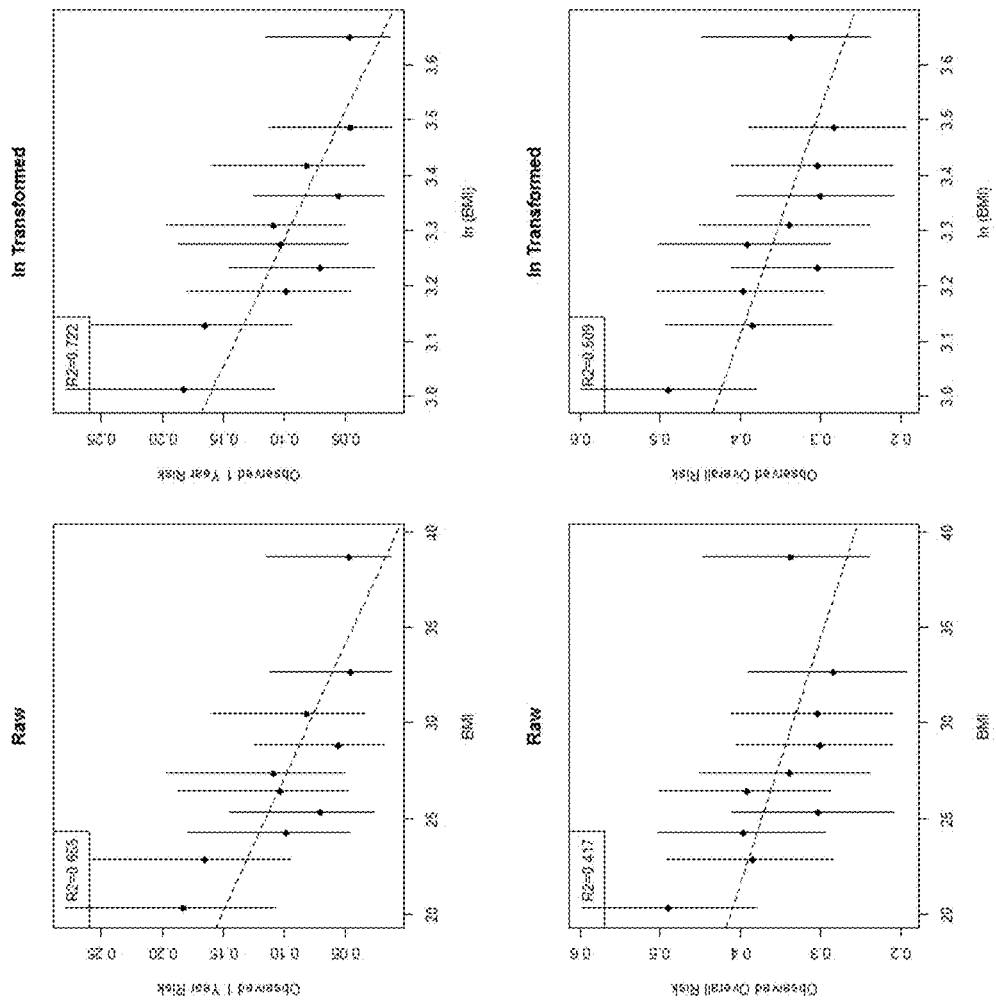
Fig. 23 Linearity Check: BMI

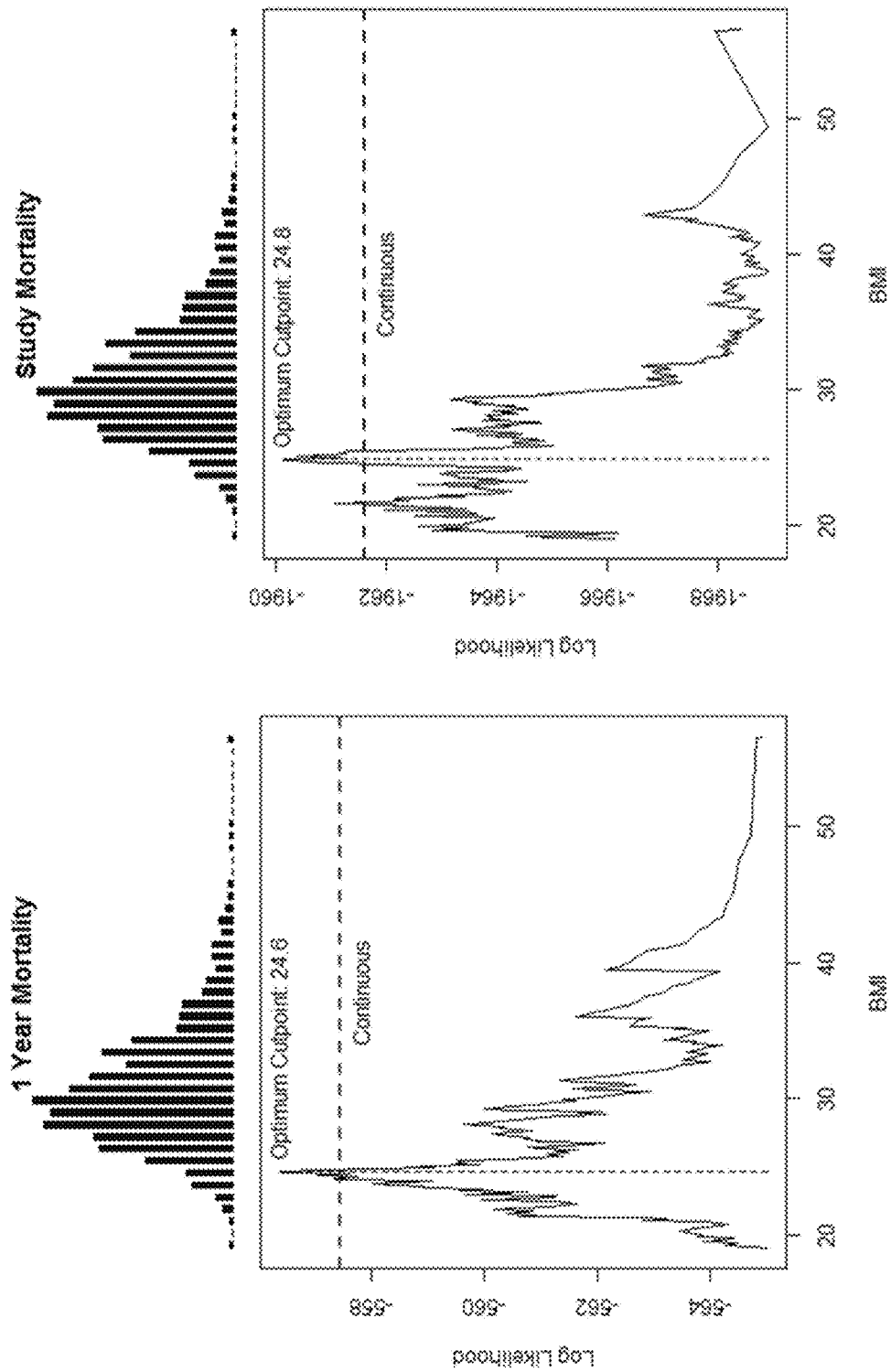
Fig. 24 Cut-Point Evaluation BMI

Fig. 25 Summary of Results

| Variables | 1-Yr Cut | Study-Cut | Selected Cut | Transformed | Comments |
|---|---|---|---|---|---|
| NTproBNP_pg_ml | 1675 | 1836 | 1700 | Yes | Consistent with cutpoint identified |
| cTnT1 | 29.06 | 16.41 | 16 | Yes | Not enough observations ion the low group |
| Creatinine | 1.27 | 1.26 | None | Yes | Moderate decrease in GFR |
| eGFR | 26.7 | 54.25 | 50 | Yes | Selected for historical comparison |
| SBP | 99 | 101 | 120 | No | Not enough observations ion the low group |
| DBP | 69 | 68 | None | No | Not enough observations ion the low group |
| HGB_g_dl | 11 | 12.3 | None | Yes | Not nearly as good as continuous |
| Age_Yr | 82 | 65.9 | None | No | |
| ST2_ng_ml | 51.6 | 50.1 | 35 / 50 | Yes | Try two different Cuts |
| LVEF | 18 | 70 | None | No | Not enough observations ion the low group |
| BMI | 24.6 | 24.8 | 25 | No | Overweight cutoff |

Fig. 26 Summary of Variables

- Continuous
  - Ln NT-proBNP
  - LN Troponin
  - LN Creatinine
  - LN eGFR
  - SBP
  - DBP
  - LN Hgb
  - Age
  - LN ST2
  - LVEF
  - BMI

- Discrete
  - NT-proBNP>=1700
  - Troponin>=16
  - eGFR<50
  - SBP<120
  - ST2>=35
  - ST2>=50
  - ST2 3 Groups
  - BMI>=25
  - NYHA>=3
  - Sex
  - CAD
  - Diabetes
  - Hypertension

Fig. 27 Top 10 Models
1 Year Outcomes (Size =1-5)

| | | Standardized Hazard Ratios | | | | | | | | | | Model Fit | | | Discrimination | | |
|---|---|---|---|---|---|---|---|---|---|---|---|---|---|---|---|---|---|
| | Age_yr | ST2 | | | Troponin | | NYHAge3 | SBPlt120 | CAD | BMI | | lnNTpro | lnCreat | lnHGB | Diabetes | | |
| Model No | | lnST2 | ST2gte50 | ST2.3g | lnTroponin | TROPONINgte16 | | | | BMI | BMIgte25 | | | | | | |
| 13488 | 1.66 | 1.48 | | | 1.53 | | 1.29 | 0.85 | | | | | | | | | |
| 16905 | 1.74 | 1.45 | | | 1.45 | | 1.29 | 1.18 | | | | | | | | | |
| 11944 | 1.76 | 1.50 | | | 1.51 | | | | | 0.81 | | | | | | | |
| 16189 | 1.69 | 1.47 | | | 1.50 | | 1.30 | | | | | 0.99 | | | | | |
| 16825 | 1.61 | | 1.42 | | 1.46 | | 1.36 | | | | | 1.16 | | | | | |
| 13506 | 1.64 | 1.54 | | | | 1.64 | 1.32 | | 0.87 | | | | | | | | |
| 3524 | 1.65 | | | 1.57 | 1.57 | | 1.34 | | | | | | | | | | |
| 16987 | 1.68 | | 1.43 | | 1.53 | | 1.35 | 1.19 | | | | | | | | | |
| 11372 | 1.62 | 1.45 | | | 1.43 | | 1.32 | | | | 0.78 | | | | | | |
| 16650 | 1.84 | 1.48 | | | 1.46 | | | | | | | | | | 0.78 | 1.18 | |

| Model No | logLik | AIC | BIC | AUC | bsAUC | LCI | UCI |
|---|---|---|---|---|---|---|---|
| 13488 | -532.0 | 1074.1 | 1098.0 | 0.802 | 0.795 | 0.734 | 0.855 |
| 16905 | -532.0 | 1074.1 | 1098.0 | 0.804 | 0.794 | 0.738 | 0.850 |
| 11944 | -534.0 | 1077.9 | 1101.9 | 0.801 | 0.792 | 0.731 | 0.854 |
| 16189 | -533.2 | 1076.4 | 1100.3 | 0.800 | 0.792 | 0.728 | 0.856 |
| 16825 | -533.8 | 1077.7 | 1101.6 | 0.795 | 0.792 | 0.725 | 0.859 |
| 13506 | -533.3 | 1076.6 | 1100.6 | 0.799 | 0.792 | 0.713 | 0.871 |
| 3524 | -534.0 | 1076.0 | 1095.2 | 0.796 | 0.790 | 0.734 | 0.846 |
| 16987 | -533.1 | 1076.2 | 1100.1 | 0.798 | 0.789 | 0.732 | 0.847 |
| 11372 | -531.3 | 1072.6 | 1096.5 | 0.804 | 0.789 | 0.715 | 0.863 |
| 16650 | -532.1 | 1074.2 | 1098.2 | 0.797 | 0.789 | 0.723 | 0.855 |

Markers Not Selected:
Ln (eGFR)
SBP
DBP
LVEF
NT-proBNP>=1700
GFR<50
ST2 >= 35
Sex
Hypertension

Fig. 28 Top 10 3 Parameter Models
1 Year Outcome

| Model No | K | Standardized Hazard Ratios | | | | | | | | Model Fit | | | Discrimination | | |
|---|---|---|---|---|---|---|---|---|---|---|---|---|---|---|---|
| | | ST2 lnST2 | ST2gte50 | Age_yr | Troponin lnTroponin | TROPONINgte16 | NYHAgte3 | NTBNPgte1700 | BMI | BMIgte25 | logLik | AIC | BIC | AUC | bsAUC | LCI | UCI |
| 476 | 3 | 1.62 | | 1.81 | | | | | | | -538.6 | 1083.2 | 1097.6 | 0.781 | 0.780 | 0.716 | 0.844 |
| 477 | 3 | 1.62 | | 1.84 | | | 1.38 | | | | -538.6 | 1083.1 | 1097.5 | 0.789 | 0.779 | 0.725 | 0.832 |
| 481 | 3 | 1.60 | | 1.78 | | 1.70 | | | | | -538.1 | 1082.3 | 1096.6 | 0.786 | 0.778 | 0.706 | 0.849 |
| 474 | 3 | 1.53 | | 1.80 | 1.57 | | | | | | -536.6 | 1079.2 | 1093.6 | 0.789 | 0.777 | 0.710 | 0.844 |
| 320 | 3 | 1.69 | | 1.91 | | | | | | | -541.1 | 1088.3 | 1102.6 | 0.782 | 0.776 | 0.714 | 0.838 |
| 1933 | 3 | 1.52 | | | 1.51 | | 1.39 | | | | -542.6 | 1091.2 | 1105.6 | 0.773 | 0.775 | 0.709 | 0.841 |
| 1934 | 3 | 1.48 | | | 1.59 | | | 1.39 | | | -542.8 | 1086.8 | 1101.2 | 0.783 | 0.774 | 0.705 | 0.844 |
| 299 | 3 | 1.68 | | 1.88 | | | | | | | -540.9 | 1087.9 | 1102.3 | 0.778 | 0.773 | 0.700 | 0.847 |
| 1978 | 3 | | 1.49 | | 1.67 | | 1.45 | | | | -540.8 | 1087.5 | 1101.9 | 0.779 | 0.773 | 0.708 | 0.838 |
| 490 | 3 | | 1.46 | 1.76 | 1.69 | | | | 0.74 | 0.80 | -539.2 | 1084.4 | 1098.8 | 0.782 | 0.771 | 0.693 | 0.850 |

Markers Not Selected:
Ln (NT-proBNP)
Ln Creatinine
Ln (eGFR)

SBP
DBP
Ln (Hgb)
LVEF

GFR<50
SBP<120
ST2 >= 35
ST2 3 Groups

Fig. 29 Selected Models Based on AIC
1 Year Outcome

Fitted AUC: 0.821
bsAUC: 0.751 [0.677-0.824]

Backward Selection

|  | HR | 95% CI | P |
|---|---|---|---|
| ln (Troponin) | 1.34 | 1.01-1.78 | 0.0423 |
| ln (Creatinine) | 0.08 | 0.02-0.26 | <0.0001 |
| ln (eGFR) | 0.09 | 0.03-0.28 | <0.0001 |
| ln (Hgb) | 0.28 | 0.07-1.03 | 0.056 |
| ln (ST2) | 2.05 | 1.37-3.08 | 0.0005 |
| LVEF | 1.02 | 1-1.04 | 0.028 |
| NTproBNP>=1700 | 1.53 | 0.87-2.66 | 0.1377 |
| SBP<120 | 1.55 | 0.98-2.44 | 0.06 |
| NYHA>=3 | 1.67 | 1.06-2.64 | 0.028 |
| Sex | 3.76 | 1.95-7.26 | <0.0001 |
| Diabetes | 1.44 | 0.92-2.25 | 0.11 |

Fitted AUC: 0.818
bsAUC: 0.751 [0.677-0.825]

Forward Selection

|  | HR | 95% CI | P |
|---|---|---|---|
| ln (Troponin) | 1.43 | 1.11-1.84 | 0.0053 |
| ln (ST2) | 2.26 | 1.51-3.38 | <0.0001 |
| Age | 1.05 | 1.02-1.07 | 0.0002 |
| NYHA>=3 | 1.69 | 1.07-2.65 | 0.0239 |
| ln (HGB) | 0.27 | 0.07-1.02 | 0.0535 |
| BMI>=25 | 0.63 | 0.41-0.98 | 0.0408 |
| SBP<120 | 1.46 | 0.93-2.28 | 0.0977 |
| Diabetes | 1.6 | 1.01-2.53 | 0.047 |
| CAD | 0.68 | 0.44-1.06 | 0.0855 |
| Hypertension | 0.67 | 0.41-1.07 | 0.0942 |

Fitted AUC: 0.818
bsAUC: 0.751 [0.677-0.824]

Stepwise Selection

|  | HR | 95% CI | P |
|---|---|---|---|
| ln (Troponin) | 1.43 | 1.11-1.84 | 0.0053 |
| ln (ST2) | 2.26 | 1.51-3.38 | <0.0001 |
| Age | 1.05 | 1.02-1.07 | 0.0002 |
| NYHA>=3 | 1.69 | 1.07-2.65 | 0.0239 |
| ln (HGB) | 0.27 | 0.07-1.02 | 0.0535 |
| BMI>=25 | 0.63 | 0.41-0.98 | 0.0408 |
| SBP<120 | 1.46 | 0.93-2.28 | 0.0977 |
| Diabetes | 1.6 | 1.01-2.53 | 0.047 |
| CAD | 0.68 | 0.44-1.06 | 0.0855 |
| Hypertension | 0.67 | 0.41-1.07 | 0.0942 |

Fig. 30 Selected Models Based on BIC 1 Year Outcome

Fitted AUC: 0.818
bsAUC: 0.796 [0.756-0.836]

Backward Selection

| | HR | 95% CI | P |
|---|---|---|---|
| ln (Troponin) | 1.45 | 1.12-1.88 | 0.0043 |
| ln (Creatinine) | 0.09 | 0.03-0.29 | <0.0001 |
| ln (eGFR) | 0.09 | 0.03-0.27 | <0.0001 |
| ln (ST2) | 2.23 | 1.48-3.35 | 0.0001 |
| NYHA>=3 | 1.86 | 1.18-2.92 | 0.0074 |
| Sex | 3 | 1.62-5.57 | 0.0005 |

Fitted AUC: 0.817
bsAUC: 0.797 [0.757-0.837]

Stepwise Selection

| | HR | 95% CI | P |
|---|---|---|---|
| ln (Troponin) | 1.49 | 1.18-1.89 | 0.0008 |
| ln (ST2) | 2.34 | 1.59-3.47 | <0.0001 |
| Age | 1.04 | 1.02-1.07 | 0.0004 |
| NYHA>=3 | 1.82 | 1.16-2.85 | 0.0091 |

Fitted AUC: 0.817
bsAUC: 0.798 [0.758-0.837]

Forward Selection

| | HR | 95% CI | P |
|---|---|---|---|
| ln (Troponin) | 1.49 | 1.18-1.89 | 0.0008 |
| ln (ST2) | 2.34 | 1.59-3.47 | <0.0001 |
| Age | 1.04 | 1.02-1.07 | 0.0004 |
| NYHA>=3 | 1.82 | 1.16-2.85 | 0.0091 |

Fig. 31 Top 10 Models Study Outcomes (Size =1-5)

| Model No | K | Age_yr | ST2gte50 | NYHAgte3 | TROPONINgte16 | lnTroponin | lneGFR | lnHGB | lnCreat | SBP | CAD | HTN | loglik | AIC | BIC | AUC | bsAUC | LCI | UCI |
|---|---|---|---|---|---|---|---|---|---|---|---|---|---|---|---|---|---|---|---|
| 16776 | 5 | 1.67 | 1.39 | 1.34 | 1.65 | | | 0.84 | | | | | -1881.2 | 3772.3 | 3796.3 | 0.818 | 0.817 | 0.782 | 0.853 |
| 16581 | 5 | 1.60 | 1.37 | 1.35 | 1.65 | | 0.89 | | | | | | -1884.6 | 3779.2 | 3803.2 | 0.817 | 0.817 | 0.775 | 0.859 |
| 16692 | 5 | 1.71 | 1.36 | 1.30 | | 1.54 | | 0.85 | | | | | -1882.5 | 3775.1 | 3799.0 | 0.818 | 0.816 | 0.773 | 0.858 |
| 17095 | 5 | 1.69 | 1.38 | 1.35 | 1.70 | | | | | 0.98 | | | -1886.1 | 3782.2 | 3806.1 | 0.815 | 0.815 | 0.777 | 0.853 |
| 13616 | 5 | 1.68 | 1.38 | 1.36 | 1.70 | | | | 1.13 | | | | -1886.1 | 3782.3 | 3806.2 | 0.816 | 0.815 | 0.776 | 0.853 |
| 16317 | 5 | 1.68 | 1.37 | 1.36 | 1.64 | | | | | | 1.01 | | -1884.2 | 3778.3 | 3802.3 | 0.817 | 0.815 | 0.777 | 0.852 |
| 3526 | 4 | 1.72 | 1.36 | 1.33 | | 1.59 | | | | | | | -1887.2 | 3782.5 | 3801.6 | 0.815 | 0.814 | 0.774 | 0.854 |
| 3610 | 4 | 1.68 | 1.38 | 1.36 | 1.70 | | | | | | | | -1886.2 | 3780.3 | 3799.5 | 0.815 | 0.814 | 0.777 | 0.851 |
| 16497 | 5 | 1.66 | 1.35 | 1.33 | | 1.55 | 0.92 | | | | | | -1886.5 | 3783.0 | 3807.0 | 0.816 | 0.814 | 0.774 | 0.854 |
| 15971 | 5 | 1.70 | 1.38 | 1.36 | 1.71 | | | | | | | 0.94 | -1885.6 | 3781.3 | 3805.3 | 0.817 | 0.813 | 0.773 | 0.853 |

Markers Not Selected: LVEF    SBP<120    Sex
Ln (NT-proBNP)    BMI    ST2>=35    Diabetes
DBP    NT-proBNP>=1700    ST2 3 Group
Ln (ST2)    GFR<50    BMI >=25

Fig. 32 Top 10 3 Parameter Models Study Outcomes

| Model No | K | Age_Yr | ST2gte50 | ST2.3g | lnST2 | TROPONINgte16 | lnTroponin | NYHAgte3 | logLik | AIC | BIC | AUC | bsAUC | LCI | UCI |
|---|---|---|---|---|---|---|---|---|---|---|---|---|---|---|---|
| 514 | 3 | 1.73 | | | | 1.81 | | 1.36 | -1904.8 | 3815.6 | 3830.0 | 0.799 | 0.797 | 0.763 | 0.831 |
| 513 | 3 | 1.89 | 1.48 | | | | | 1.42 | -1913.0 | 3832.0 | 3846.4 | 0.799 | 0.795 | 0.757 | 0.832 |
| 511 | 3 | 1.90 | | 1.53 | | | | 1.39 | -1914.0 | 3833.9 | 3848.3 | 0.794 | 0.794 | 0.756 | 0.832 |
| 477 | 3 | 1.90 | | | 1.44 | | | 1.38 | -1915.8 | 3837.7 | 3852.0 | 0.798 | 0.794 | 0.754 | 0.833 |
| 488 | 3 | 1.85 | | 1.39 | | 1.77 | | | -1900.2 | 3806.3 | 3820.7 | 0.793 | 0.793 | 0.754 | 0.831 |
| 531 | 3 | 1.82 | 1.38 | | | | 1.69 | | -1903.2 | 3812.4 | 3826.7 | 0.795 | 0.792 | 0.755 | 0.829 |
| 490 | 3 | 1.84 | 1.35 | | | | 1.70 | | -1901.2 | 3808.4 | 3822.8 | 0.796 | 0.791 | 0.751 | 0.831 |
| 484 | 3 | 1.79 | | | | | 1.72 | 1.31 | -1903.2 | 3812.4 | 3826.7 | 0.797 | 0.791 | 0.754 | 0.828 |
| 529 | 3 | 1.83 | | 1.43 | | 1.75 | | | -1903.1 | 3812.2 | 3826.6 | 0.793 | 0.790 | 0.757 | 0.824 |
| 481 | 3 | 1.83 | | | 1.36 | 1.74 | | | -1904.7 | 3815.4 | 3829.8 | 0.794 | 0.790 | 0.744 | 0.836 |

Markers Not Selected:
Ln (NT-proBNP)
Ln Creatinine
Ln (eGFR)

SBP
DBP
Ln (Hgb)
LVEF

BMI
NT-proBNP >=1700
GFR<50
SBP<120

ST2 >= 35
BMI>=25
SEX
CAD

Diabetes
Hypertension

Fig. 33 Models Based on AIC Study Outcome

Fitted AUC: 0.808
bsAUC: 0.741 [0.665-0.816]

Backward Selection

|  | HR | 95% CI | P |
|---|---|---|---|
| ln (NT-proBNP) | 1.13 | 1.01-1.27 | 0.0407 |
| ln (Troponin) | 1.19 | 0.99-1.44 | 0.0695 |
| ln (Creatinine) | 1.69 | 0.91-3.15 | 0.0953 |
| ln (eGFR) | 1.58 | 0.85-2.94 | 0.1483 |
| ln (Hgb) | 0.34 | 0.17-0.68 | 0.002 |
| Age | 1.05 | 1.03-1.07 | <0.0001 |
| Troponin >=16 | 1.88 | 1.26-2.8 | 0.0021 |
| ST2 >=50 | 1.89 | 1.49-2.4 | <0.0001 |
| NYHA >= 3 | 1.84 | 1.46-2.32 | <0.0001 |

Fitted AUC: 0.800
bsAUC: 0.743 [0.666-0.837]

Stepwise Selection

|  | HR | 95% CI | P |
|---|---|---|---|
| ln (Troponin) | 1.2 | 1-1.45 | 0.0534 |
| Age | 1.04 | 1.03-1.05 | <0.0001 |
| ST2 >=50 | 1.87 | 1.47-2.38 | <0.0001 |
| NYHA >= 3 | 1.84 | 1.45-2.32 | <0.0001 |
| Troponin >=16 | 1.88 | 1.25-2.8 | 0.0022 |
| ln (Hgb) | 0.34 | 0.18-0.68 | 0.0019 |
| ln (NT-proBNP) | 1.12 | 1.01-1.26 | 0.0401 |
| Sex | 1.2 | 0.94-1.54 | 0.1522 |

Fitted AUC: 0.800
bsAUC: 0.744 [0.667-0.821]

Forward Selection

|  | HR | 95% CI | P |
|---|---|---|---|
| ln (Troponin) | 1.2 | 1-1.45 | 0.0534 |
| Age | 1.04 | 1.03-1.05 | <0.0001 |
| ST2 >=50 | 1.87 | 1.47-2.38 | <0.0001 |
| NYHA >= 3 | 1.84 | 1.45-2.32 | <0.0001 |
| Troponin >=16 | 1.88 | 1.25-2.8 | 0.0022 |
| ln (Hgb) | 0.34 | 0.18-0.68 | 0.0019 |
| ln (NT-proBNP) | 1.12 | 1.01-1.26 | 0.0401 |
| Sex | 1.2 | 0.94-1.54 | 0.1522 |

Fig. 34 Selected Models Based on BIC
1 Year Outcome

Fitted AUC:0.818
bsAUC: 0.798 [0.757-0.839]

Backward Selection

|  | HR | 95% CI | p |
|---|---|---|---|
| ln (Troponin) | 1.3 | 1.1-1.54 | 0.0022 |
| ln (Hgb) | 0.35 | 0.18-0.69 | 0.0021 |
| Age | 1.04 | 1.03-1.05 | <0.0001 |
| Troponin >=16 | 1.95 | 1.31-2.9 | 0.001 |
| ST2 >=50 | 2 | 1.58-2.52 | <0.0001 |
| NYHA >=3 | 1.83 | 1.45-2.3 | <0.0001 |

Fitted AUC:0.818
bsAUC: 0.800 [0.760-0.841]

Stepwise Selection

|  | HR | 95% CI | p |
|---|---|---|---|
| ln (Troponin) | 1.3 | 1.1-1.54 | 0.0022 |
| Age | 1.04 | 1.03-1.05 | <0.0001 |
| ST2 >=50 | 2 | 1.58-2.52 | <0.0001 |
| NYHA >=3 | 1.83 | 1.45-2.3 | <0.0001 |
| Troponin >=16 | 1.95 | 1.31-2.9 | 0.001 |
| ln (Hgb) | 0.35 | 0.18-0.69 | 0.0021 |

Fitted AUC:0.818
bsAUC: 0.801 [0.760-0.841]

Forward Selection

|  | HR | 95% CI | p |
|---|---|---|---|
| ln (Troponin) | 1.3 | 1.1-1.54 | 0.0022 |
| Age | 1.04 | 1.03-1.05 | <0.0001 |
| ST2 >=50 | 2 | 1.58-2.52 | <0.0001 |
| NYHA >=3 | 1.83 | 1.45-2.3 | <0.0001 |
| Troponin >=16 | 1.95 | 1.31-2.9 | 0.001 |
| ln (Hgb) | 0.35 | 0.18-0.69 | 0.0021 |

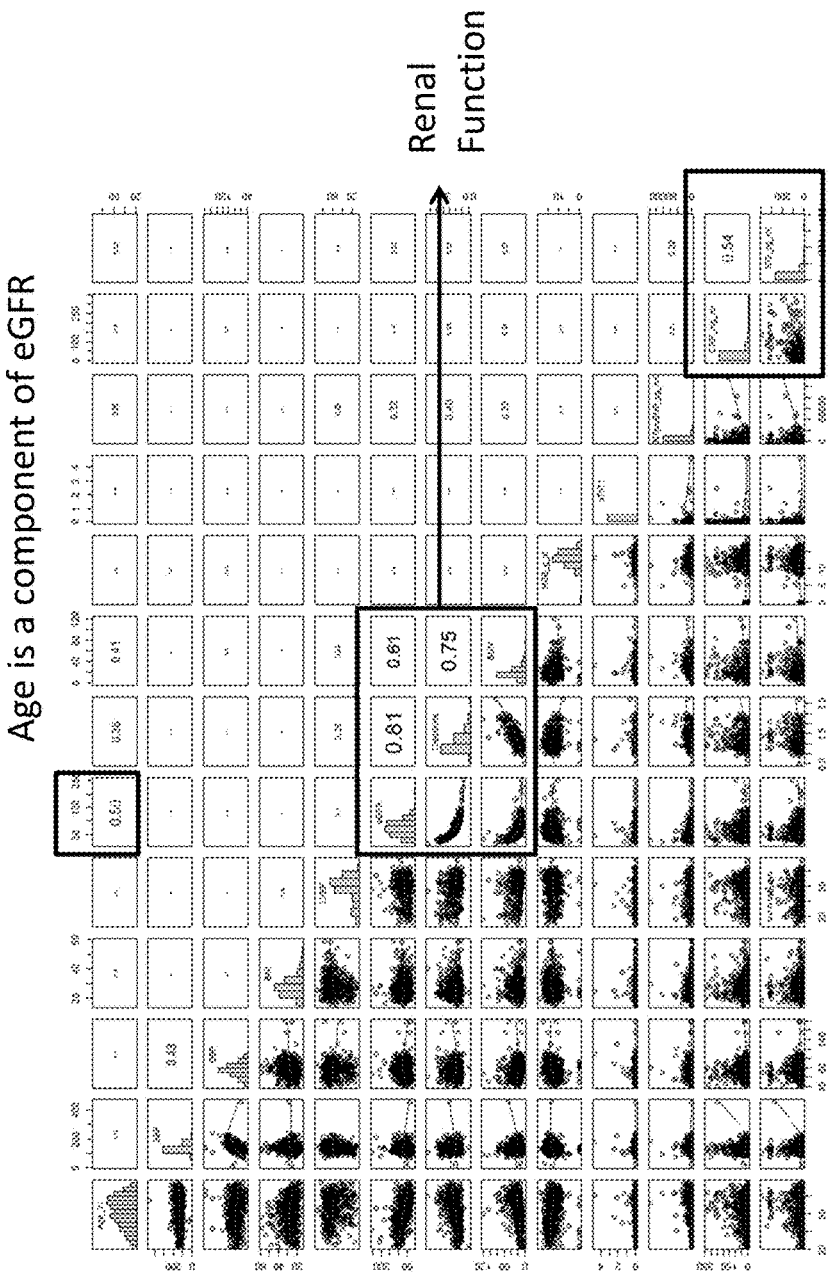
Fig. 35 Colinearity

Fig. 36 Univariate Performance

| Variable | Outcome=0 Median [IQR] | Outcome=1 Median [IQR] | Test P Value | sOR(Raw) Est [95% CI] | LRT p | sOR(ln) Est [95% CI] | LRT p | AuROC |
|---|---|---|---|---|---|---|---|---|
| Age_Yr | 73.5[61.5-81] | 80[74-85] | 0.001 | 1.75 [1.25-2.55] | <0.001 | 1.84 [1.27-2.8] | <0.001 | 0.641 |
| Sex | 0=70;1=78 | 0=32;1=29 | 0.544 | 0.81 [0.45-1.48] | 0.497 | | | |
| Ethnicity | 1=131,5=11,6=5;7=1 | 1=56;5=2;6=3 | 0.646 | | 0.502 | | | |
| Is_Black | 0=137;1=11 | 0=59;1=2 | 0.354 | 0.42 [0.06-1.63] | 0.231 | | | |
| SBP | 140[124-156.25] | 130[110-151] | 0.022 | 0.68 [0.48-0.93] | 0.016 | 0.68 [0.49-0.92] | 0.013 | 0.601 |
| DBP | 75[66-86.25] | 74[61-83] | 0.411 | 0.91 [0.67-1.23] | 0.553 | 0.9 [0.66-1.21] | 0.474 | 0.536 |
| BMI | 26.98[23.88-32] | 26.61[21.92-29.75] | 0.036 | 0.65 [0.45-0.9] | 0.009 | 0.67 [0.48-0.92] | 0.012 | 0.592 |
| HTN | 0=55;1=93 | 0=21;1=40 | 0.754 | 1.13 [0.61-2.13] | 0.708 | | | |
| Diabetes | 0=85;1=63 | 0=36;1=25 | 0.878 | 0.94 [0.51-1.71] | 0.833 | | | |
| CAD | 0=93;1=55 | 0=28;1=33 | 0.031 | 1.99 [1.09-3.67] | 0.025 | | | |
| LVEF | 52[36-62] | 51[30-67] | 0.844 | 0.94 [0.7-1.27] | 0.685 | 0.9 [0.67-1.22] | 0.491 | 0.509 |
| eGFR | 54.69[40.99-79.85] | 48.91[35.7-60.53] | 0.008 | 0.59 [0.4-0.83] | 0.002 | 0.64 [0.46-0.87] | 0.005 | 0.617 |
| Creatinine | 1.2[0.9-1.6] | 1.4[1.1-1.5] | 0.065 | 1.35 [1-1.82] | 0.047 | 1.41 [1.04-1.93] | 0.027 | 0.581 |
| BUN | 23[17-32] | 31[24-41] | <0.001 | 1.64 [1.22-2.27] | <0.001 | 1.77 [1.29-2.48] | <0.001 | 0.669 |
| HGB_g_dl | 12.7[11-14.3] | 11.3[10.1-12.5] | 0.001 | 0.63 [0.46-0.87] | 0.004 | 0.68 [0.49-0.91] | 0.01 | 0.641 |
| cTnT1 | 0[0-0.03] | 0.03[0-0.06] | 0.002 | 0.92 [0.55-1.24] | 0.611 | 1.01 [0.72-1.34] | 0.932 | 0.628 |
| NTproBNP_pg_ml | 3122.5[1401-7947.25] | 9020[3366-12991] | <0.001 | 1.61 [1.15-2.43] | 0.004 | 2.03 [1.46-2.9] | <0.001 | 0.685 |
| CRP_mg_ml | 11.9[3.77-36.12] | 36.5[9.5-92.2] | <0.001 | 1.61 [1.21-2.2] | 0.001 | 1.85 [1.34-2.61] | <0.001 | 0.666 |
| ST2_ng_ml | 37.02[23.43-64.69] | 67.39[41.62-97.23] | <0.001 | 1.77 [1.31-2.48] | <0.001 | 1.9 [1.37-2.69] | <0.001 | 0.692 |

Recall in the entire PRIDE data set, missing LVEF was not random. In this subpopulation only 6 subjects have missing LVEF data (4 cases and 2 controls)->OR=5.07 (p=0.06)

BUN looks strongest in a univariate sense

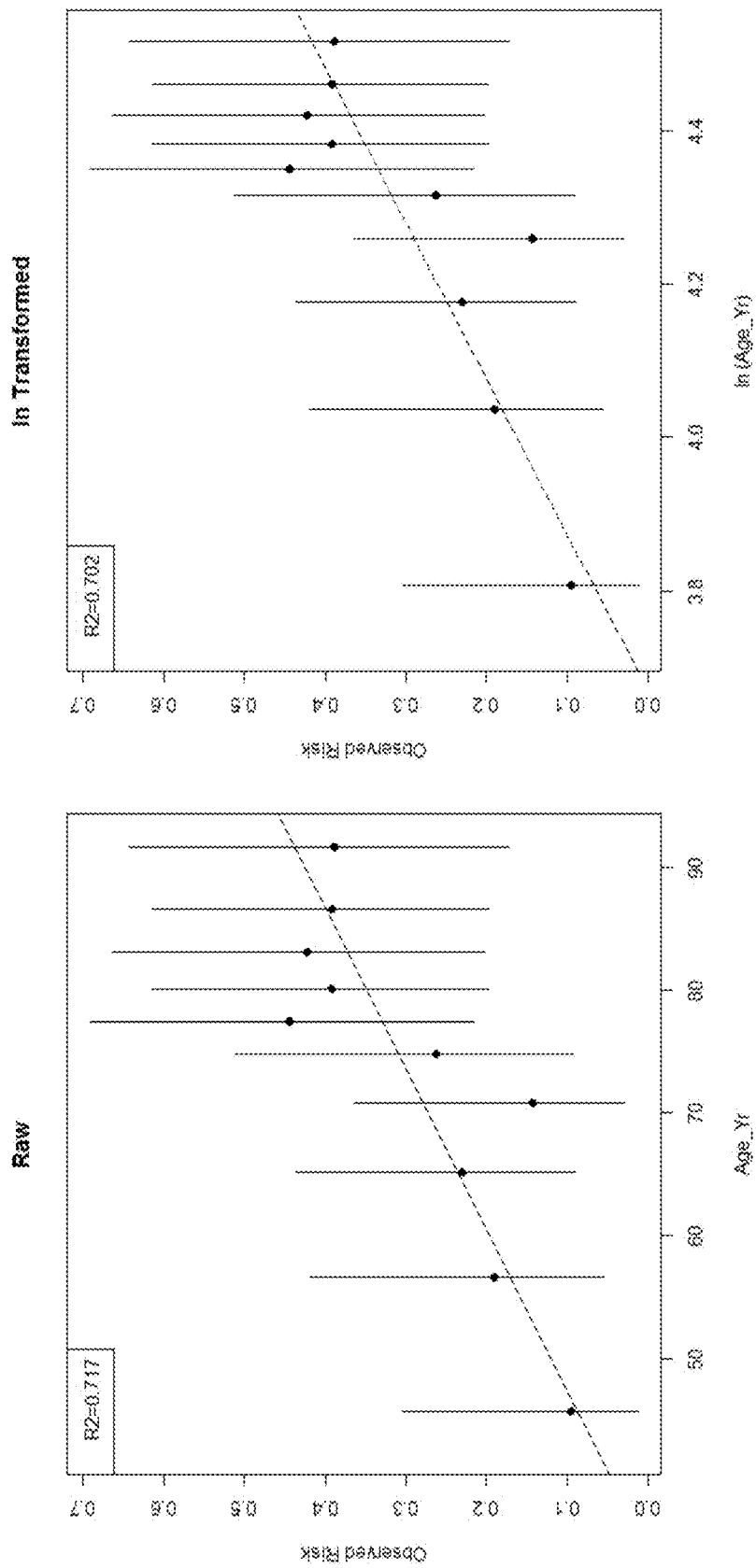
Fig. 37 Linearity Evaluation: Age

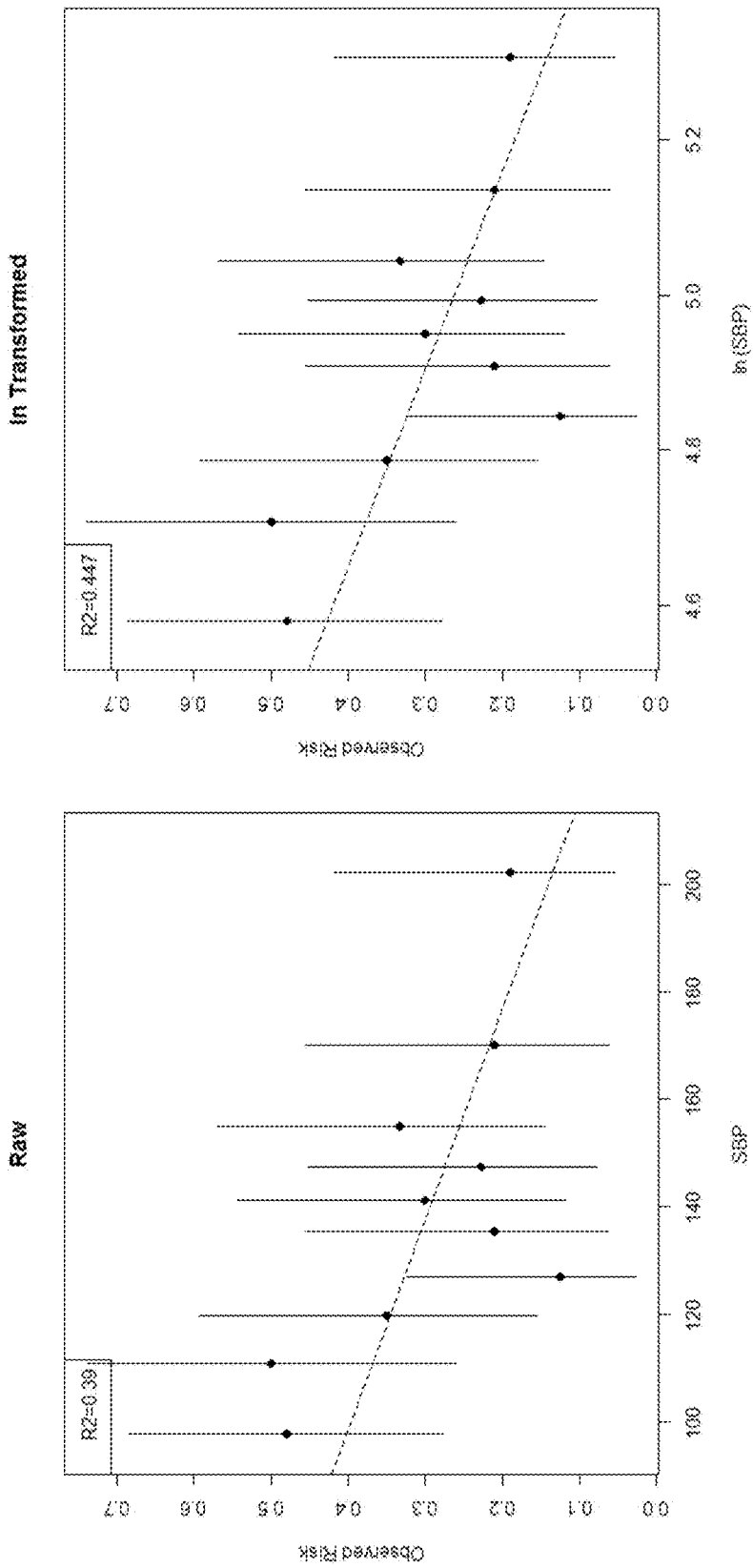
Fig. 38 Linearity Evaluation: SBP

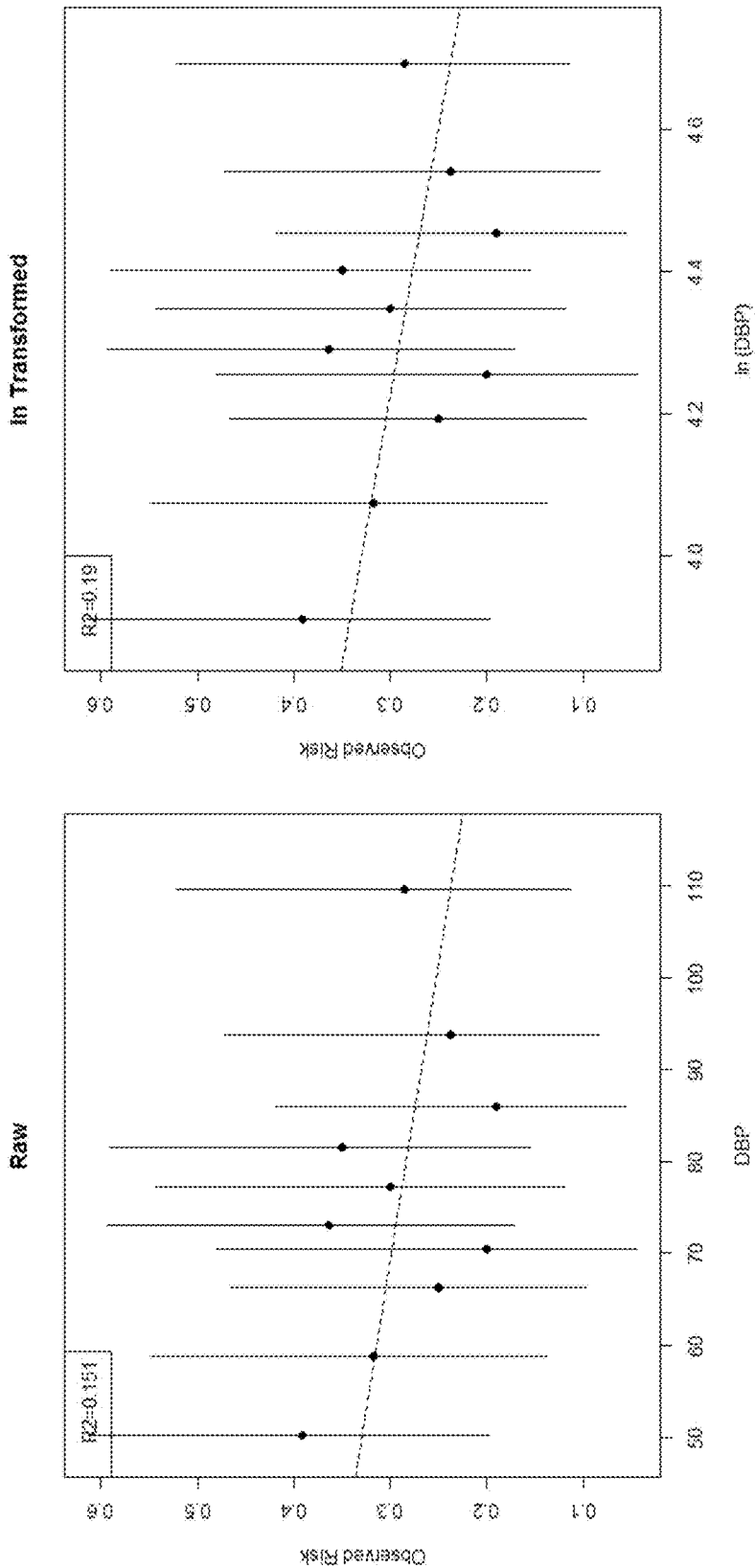
Fig. 39 Linearity Evaluation: DBP

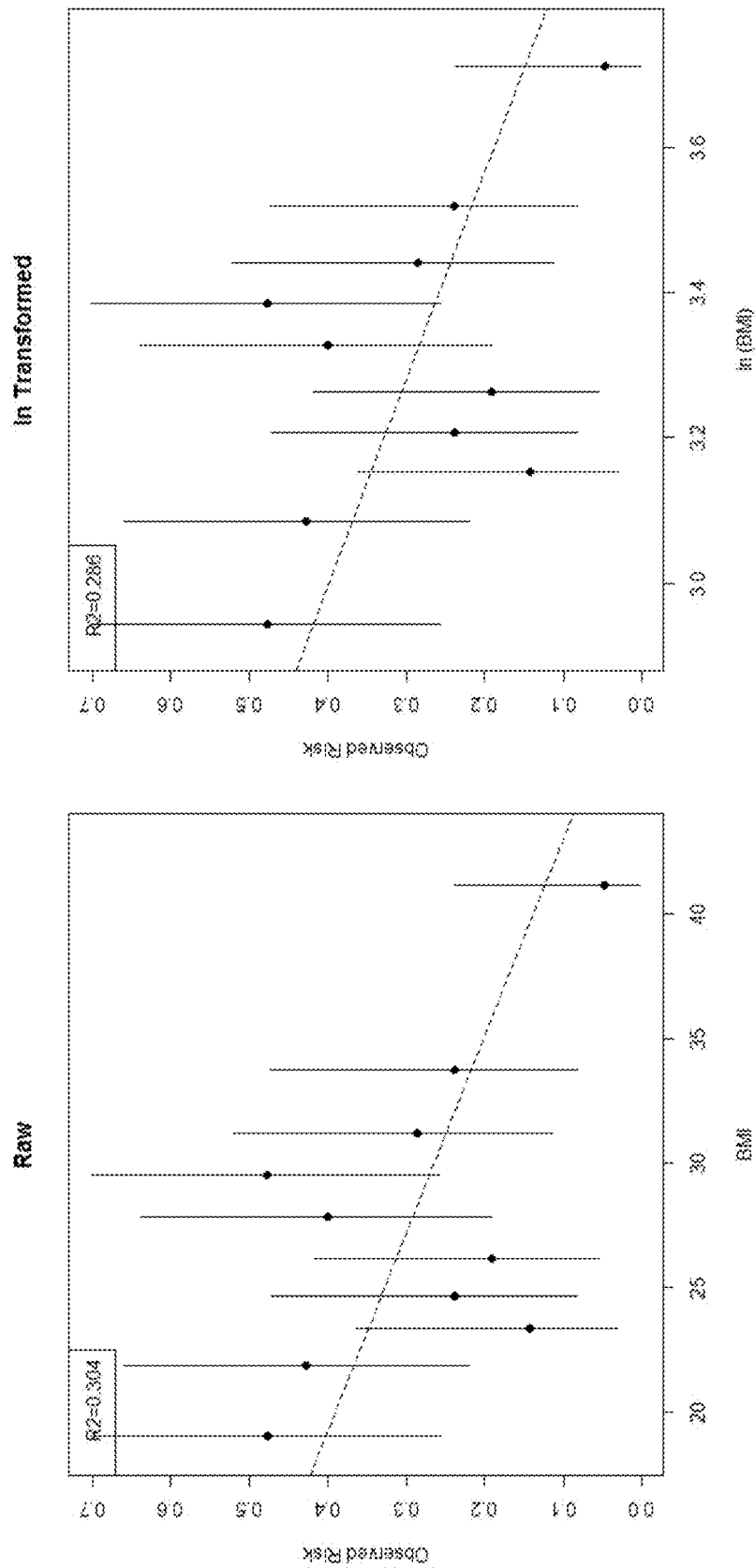
Fig. 40 Linearity Evaluation: BMI

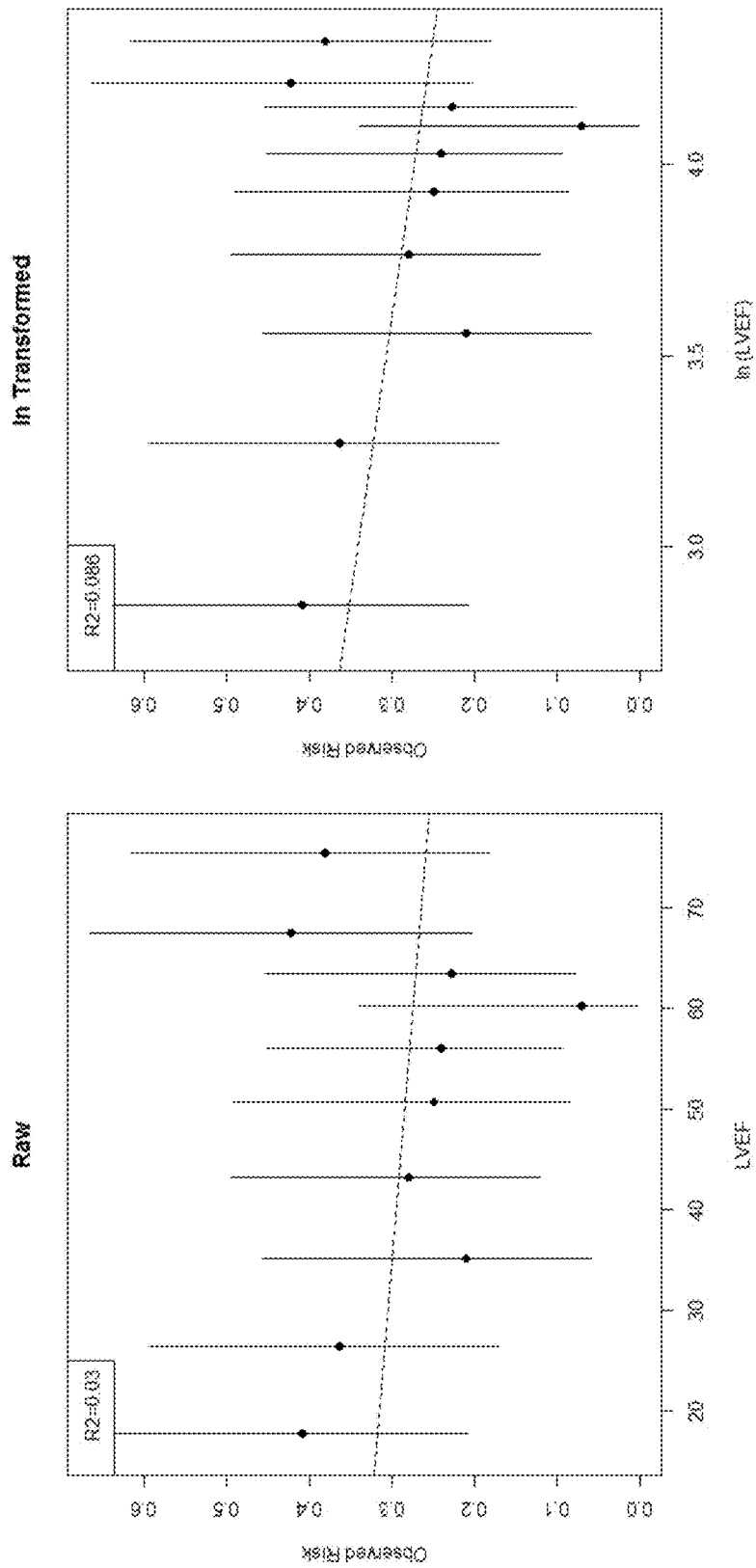
Fig. 41 Linearity Evaluation: LVEF

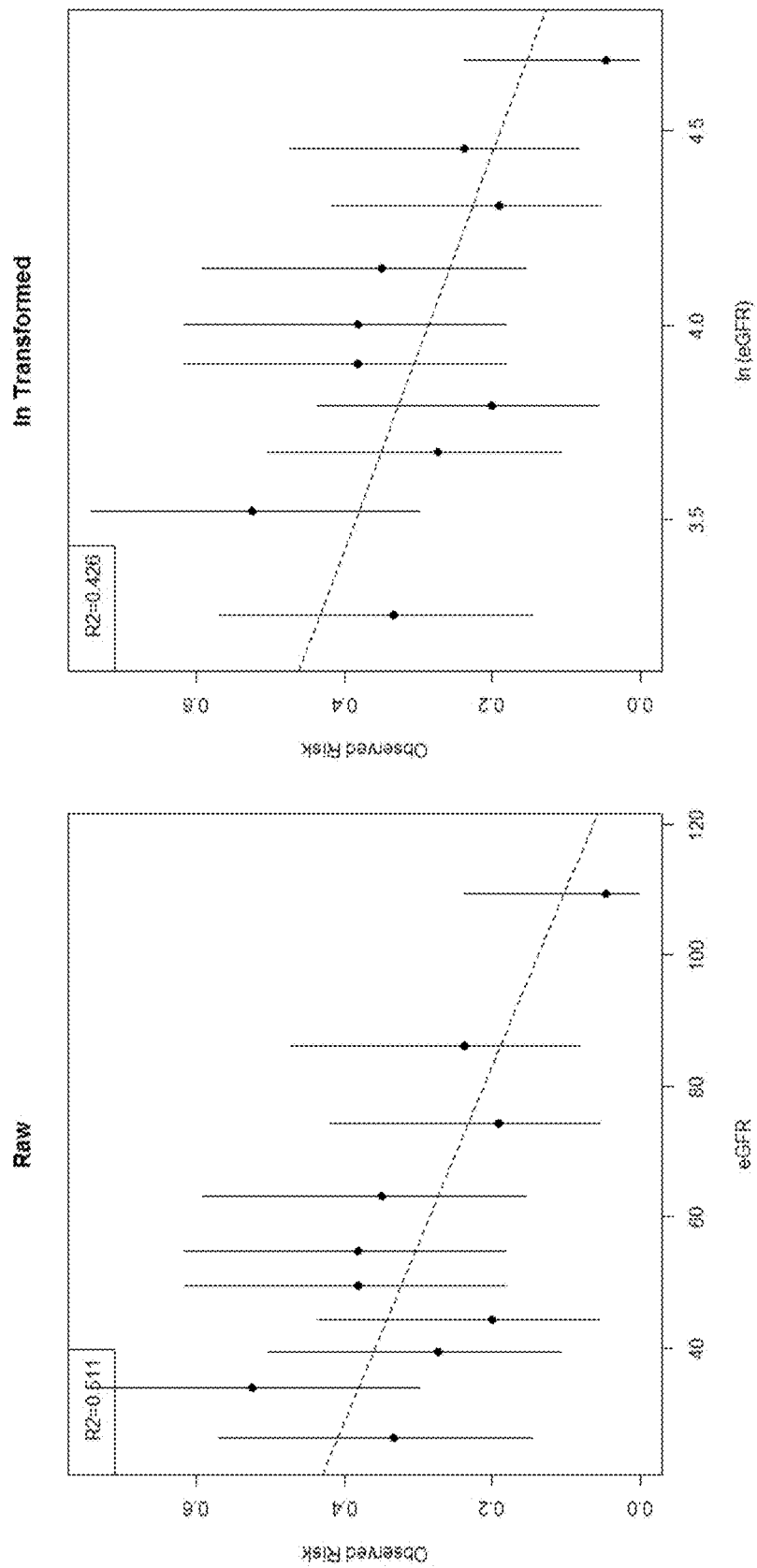
Fig. 42 Linearity Check: eGFR

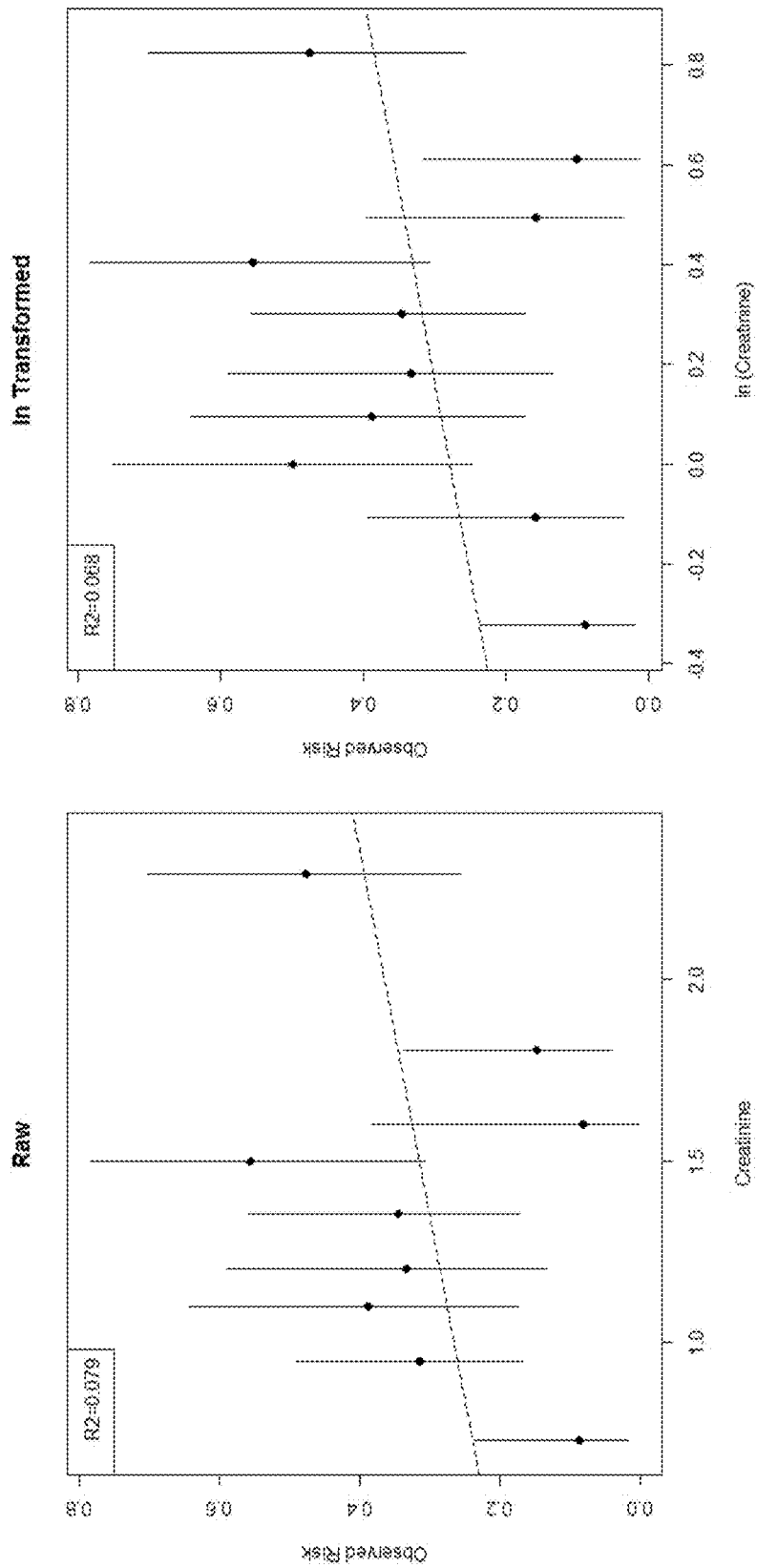
Fig. 43 Linearity Check: Creatinine

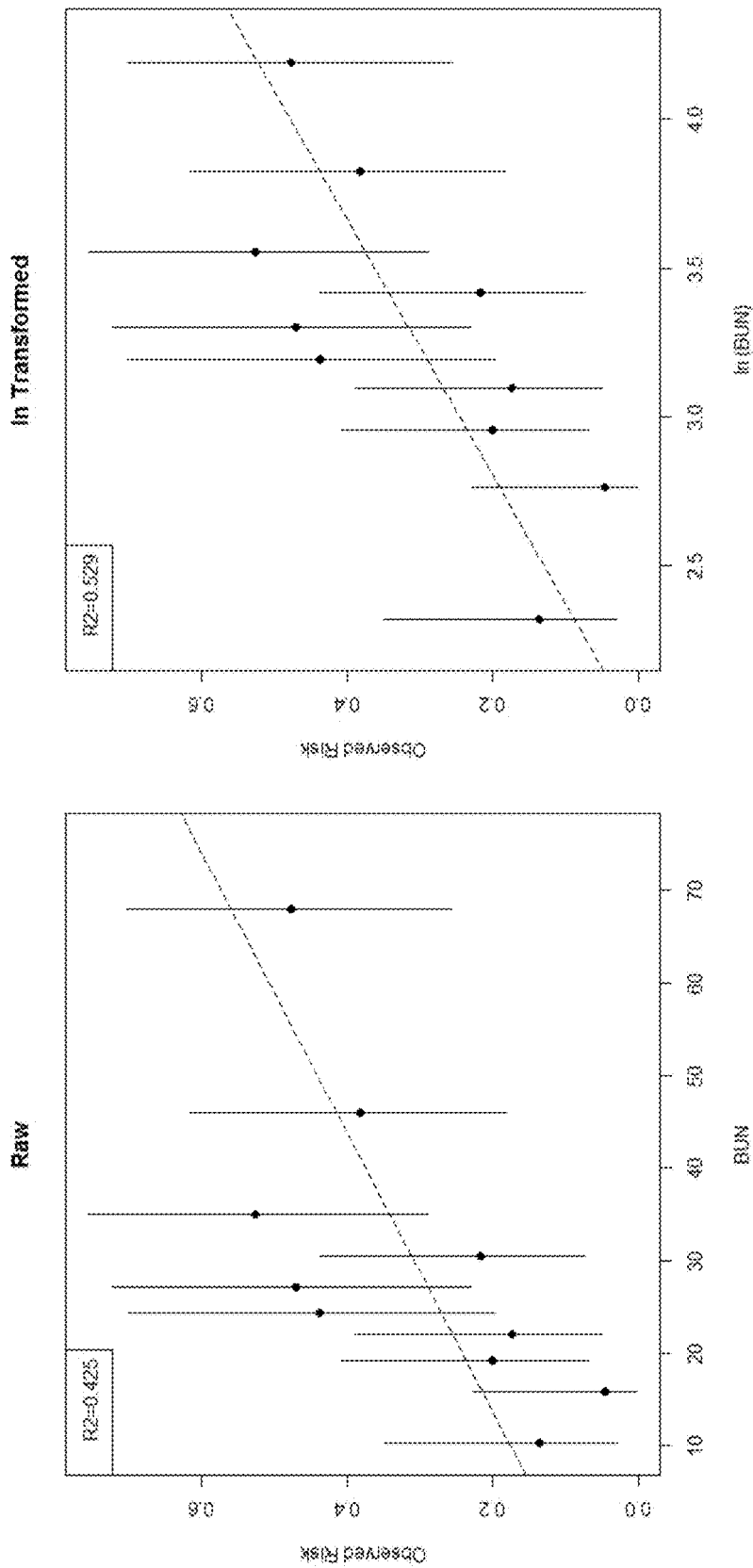
Fig. 44 Linearity Check: BUN

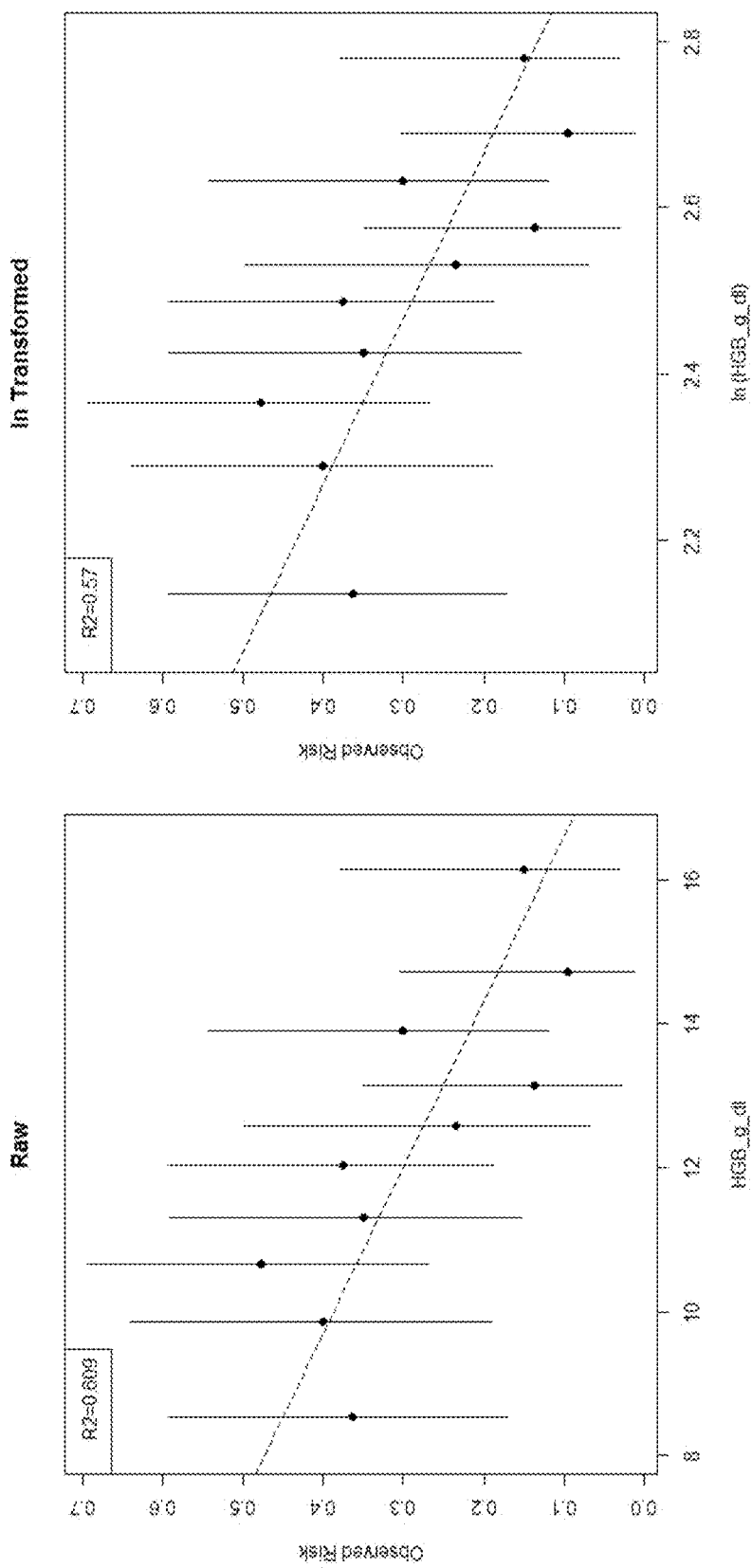
Fig. 45 Linearity Check: Hemoglobin

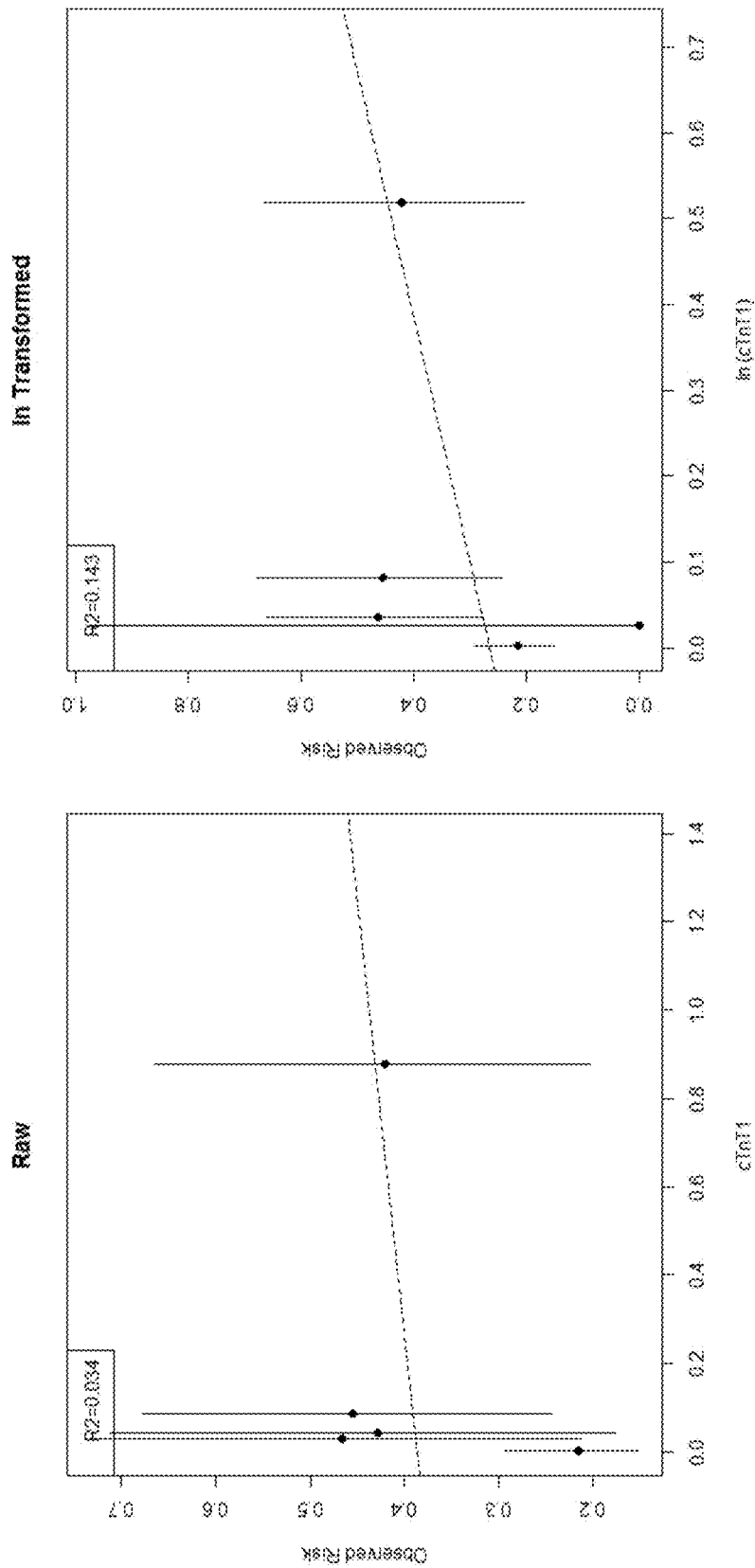
Fig. 46 Linearity Check: Troponin

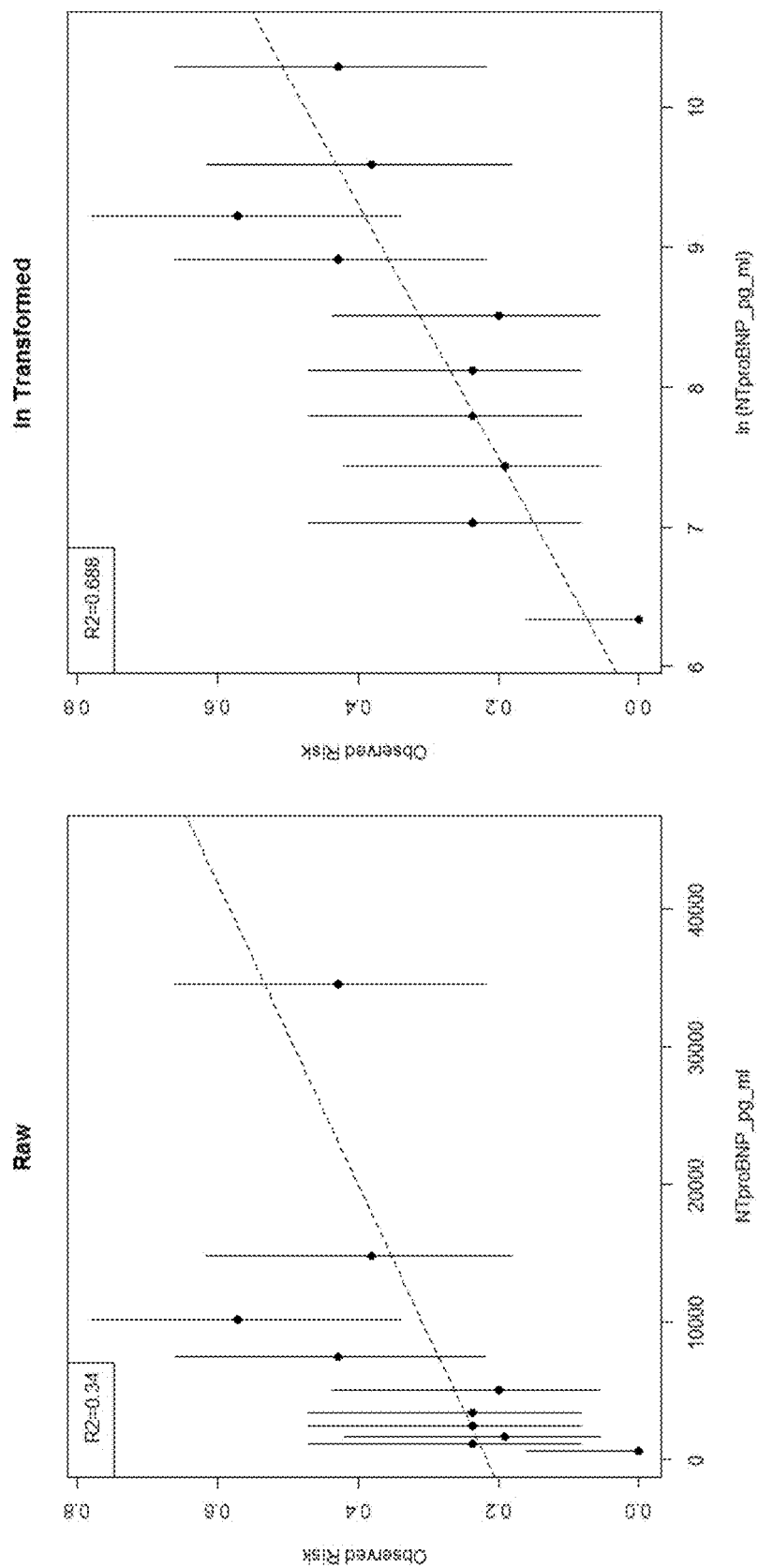
Fig. 47 Linearity Check: NT-proBNP

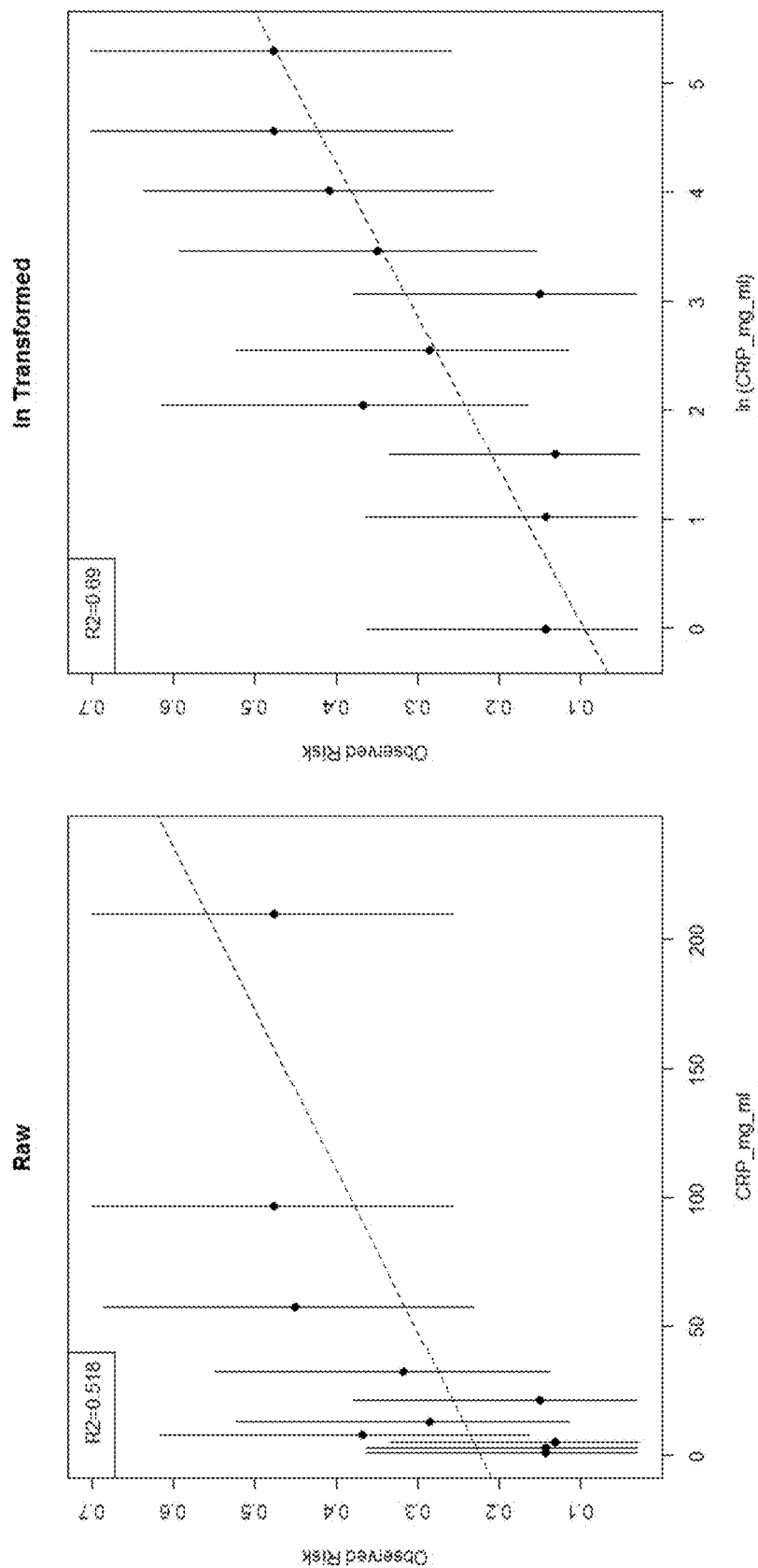
Fig. 48 Linearity Check: CRP

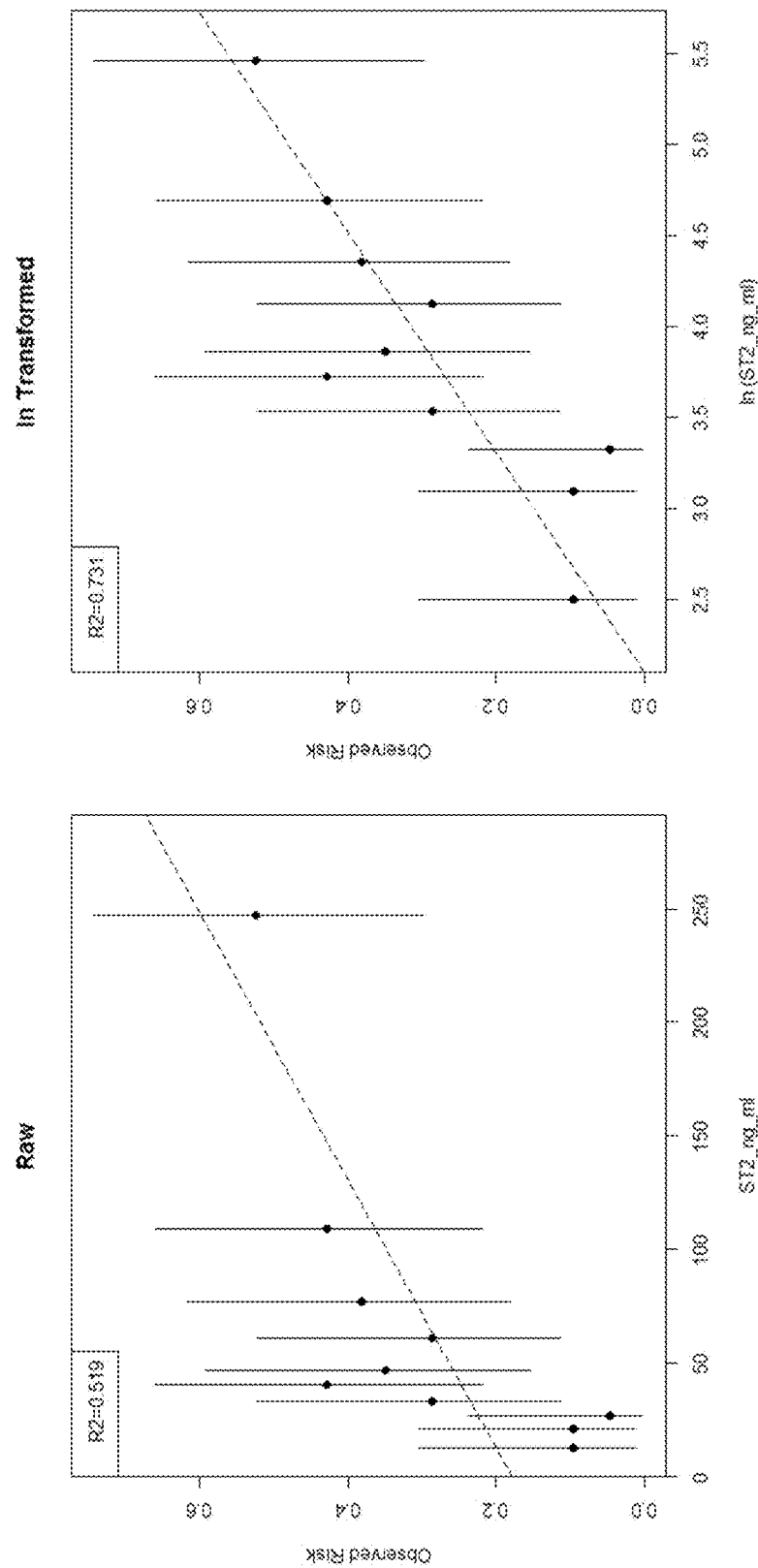
Fig. 49 Linearity Check: ST2

Fig. 50 Summary

| | AIC | | | | |
|---|---|---|---|---|---|
| | Raw | Log | Other | Comment | Graph |
| Age | 245.31 | 245.14 | | | Raw |
| SBP | 250.6 | 250.2 | 245.85 | >120 | log |
| DBP | 256.04 | 255.88 | | | log |
| BMI | 249.49 | 250.1 | | | Raw |
| LVEF | 256.23 | 255.92 | | | ? |
| eGFR | 246.93 | 248.39 | | | Raw |
| Creatinine | 252.44 | 251.53 | | | Raw |
| BUN | 245.5 | 243.6 | | | log |
| Hemoglobin | 248.07 | 249.81 | | | Raw |
| Troponin | 256.14 | 256.39 | 247.08 | >0 | ? |
| NT-proBNP | 247.98 | 237.46 | | | log |
| CRP | 245.74 | 241.77 | | | log |
| ST2 | 241.74 | 240.61 | 238.15 | >=35 | log |

AIC (Smaller is better) generally agrees with graphical approach. Bins will be considered for ST2, SBP, and Troponin

- Parameter Space
  – Age
  – Log(SBP)
  – SBP>120
  – Log(DBP)
  – BMI
  – Log(LVEF)
  – Log(BUN)
  – Hemoglobin
  – Troponin
  – Troponin>0
  – Log(NT-proBNP)
  – Log(CRP)
  – Log(ST2)
  – ST2>=35
  – Other factors (Sex, Race, Diabetes, HTN,CAD,IS_Black)

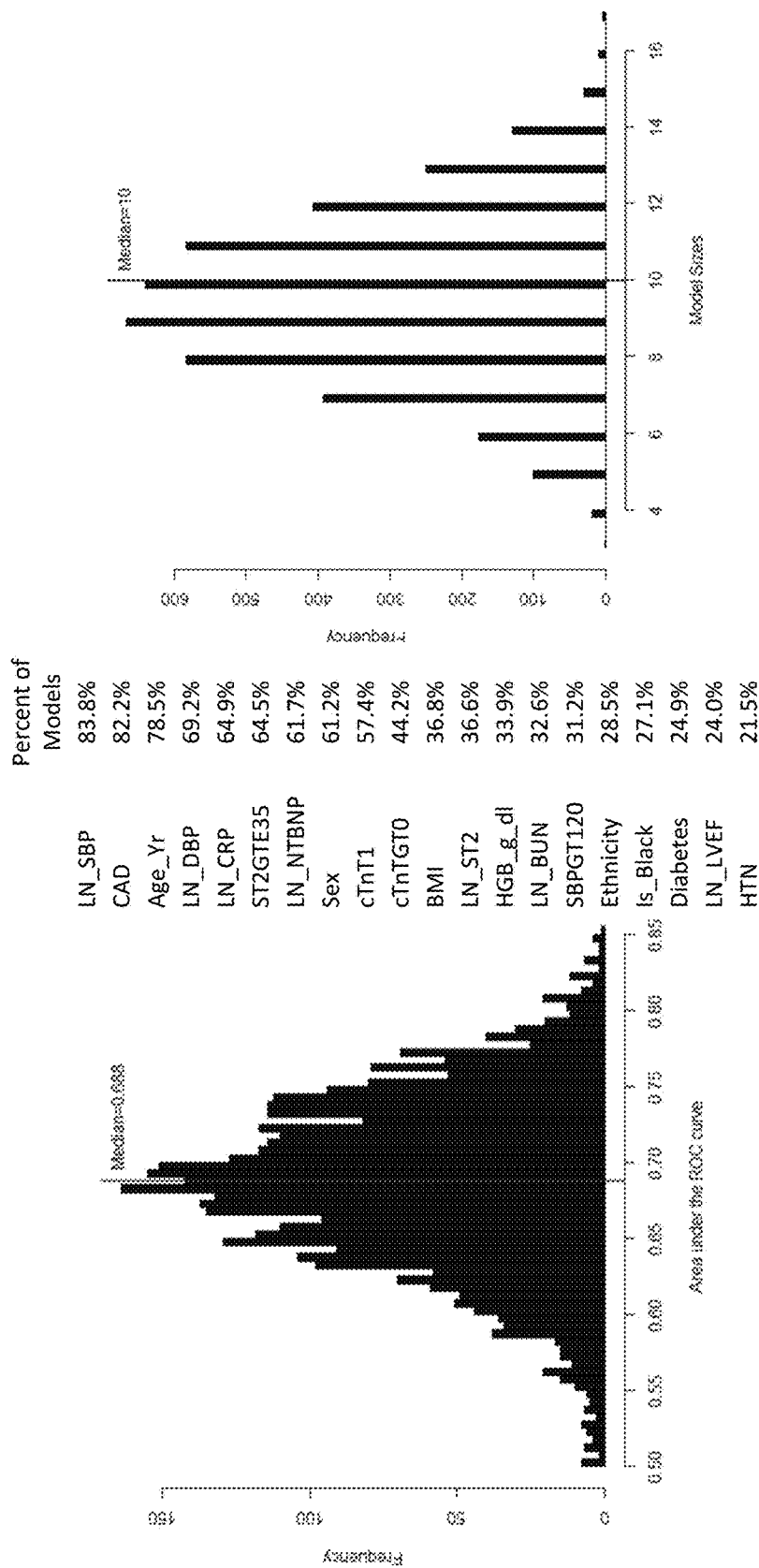
Fig. 51 Marker Selection (AIC)

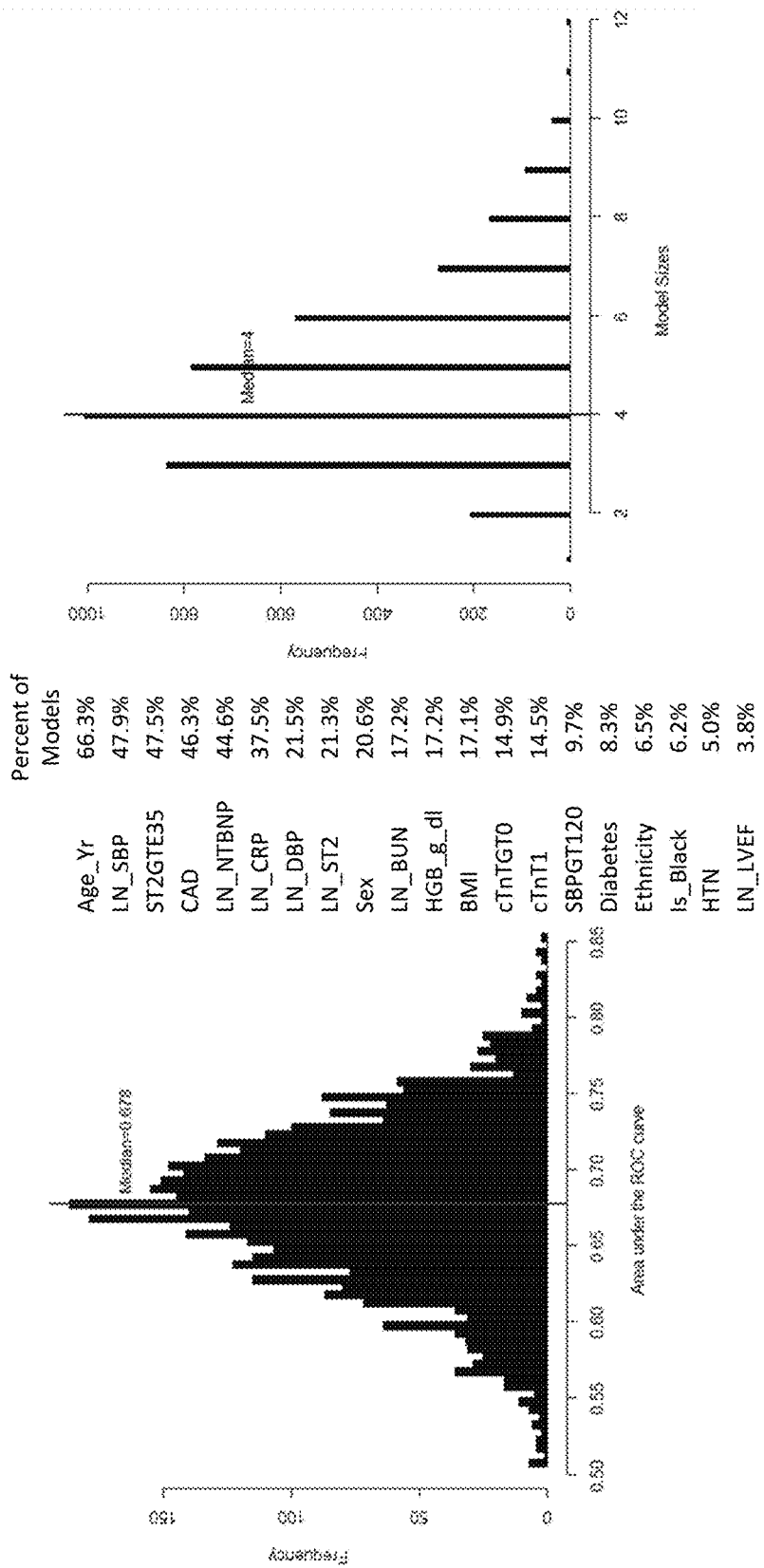
Fig. 52 BIC Based Marker Selection

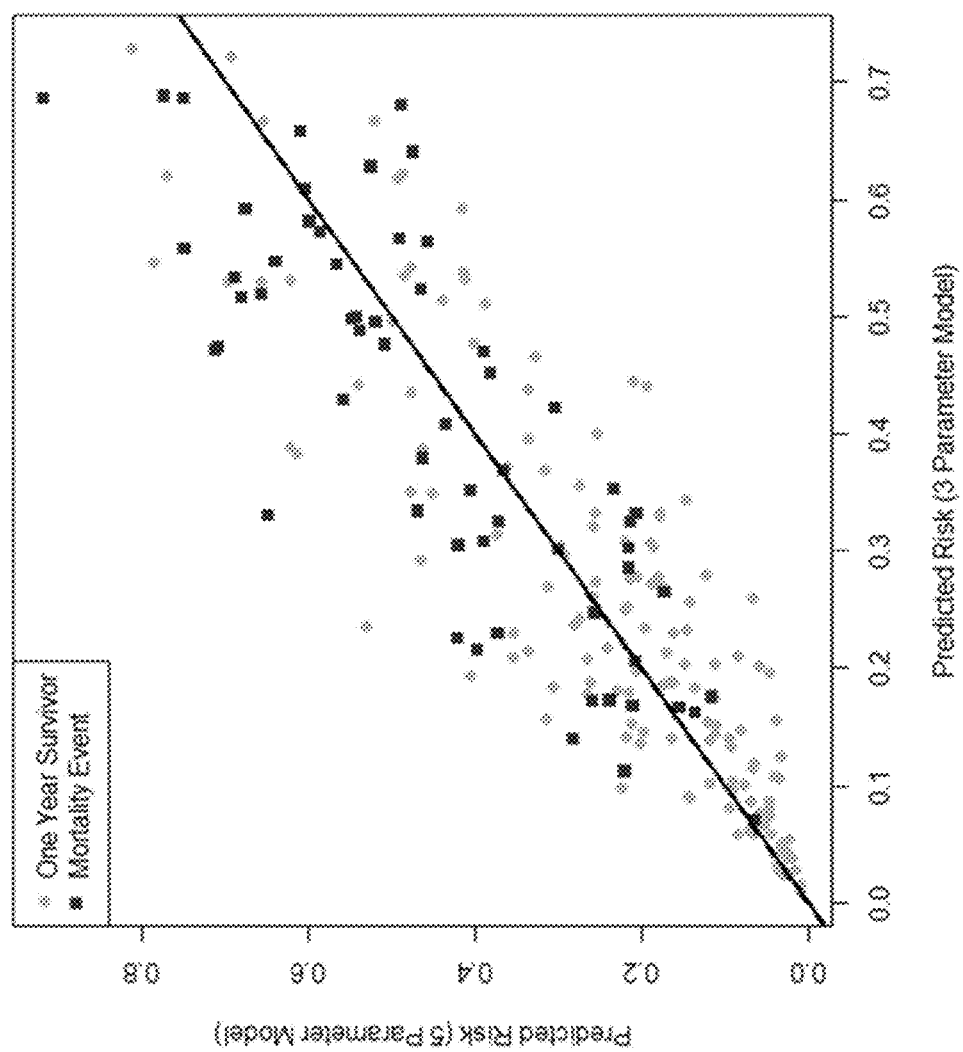
Fig. 53 Comparison of the Two Models

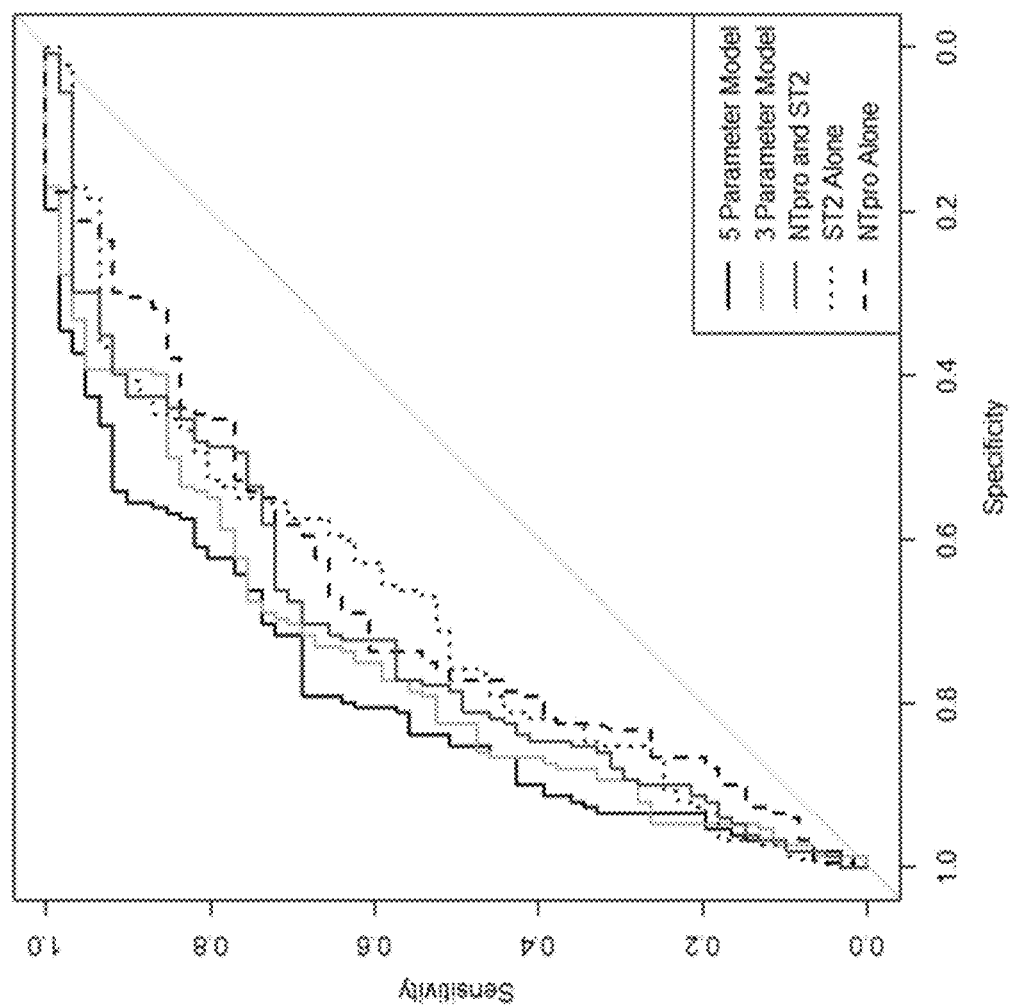
Fig. 54 ROC Curves

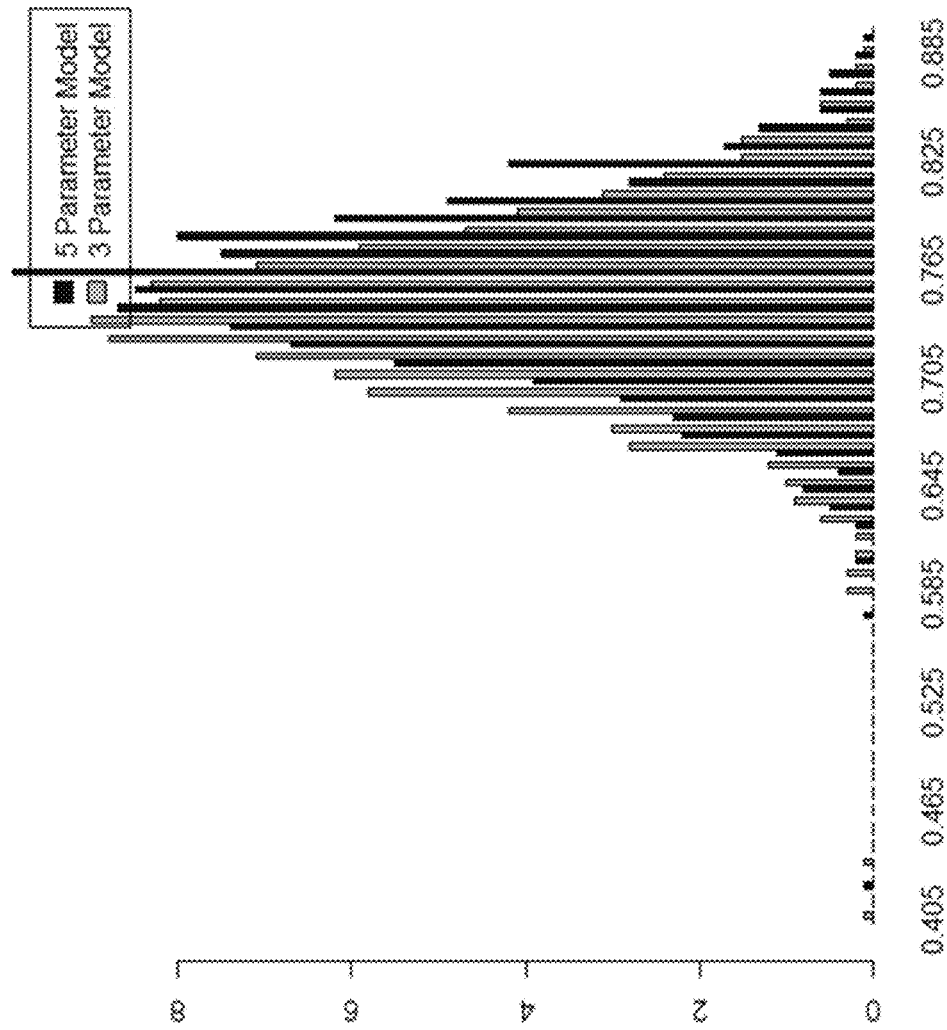
Fig. 55 Bootstrap AUC "Out of Bag" estimates

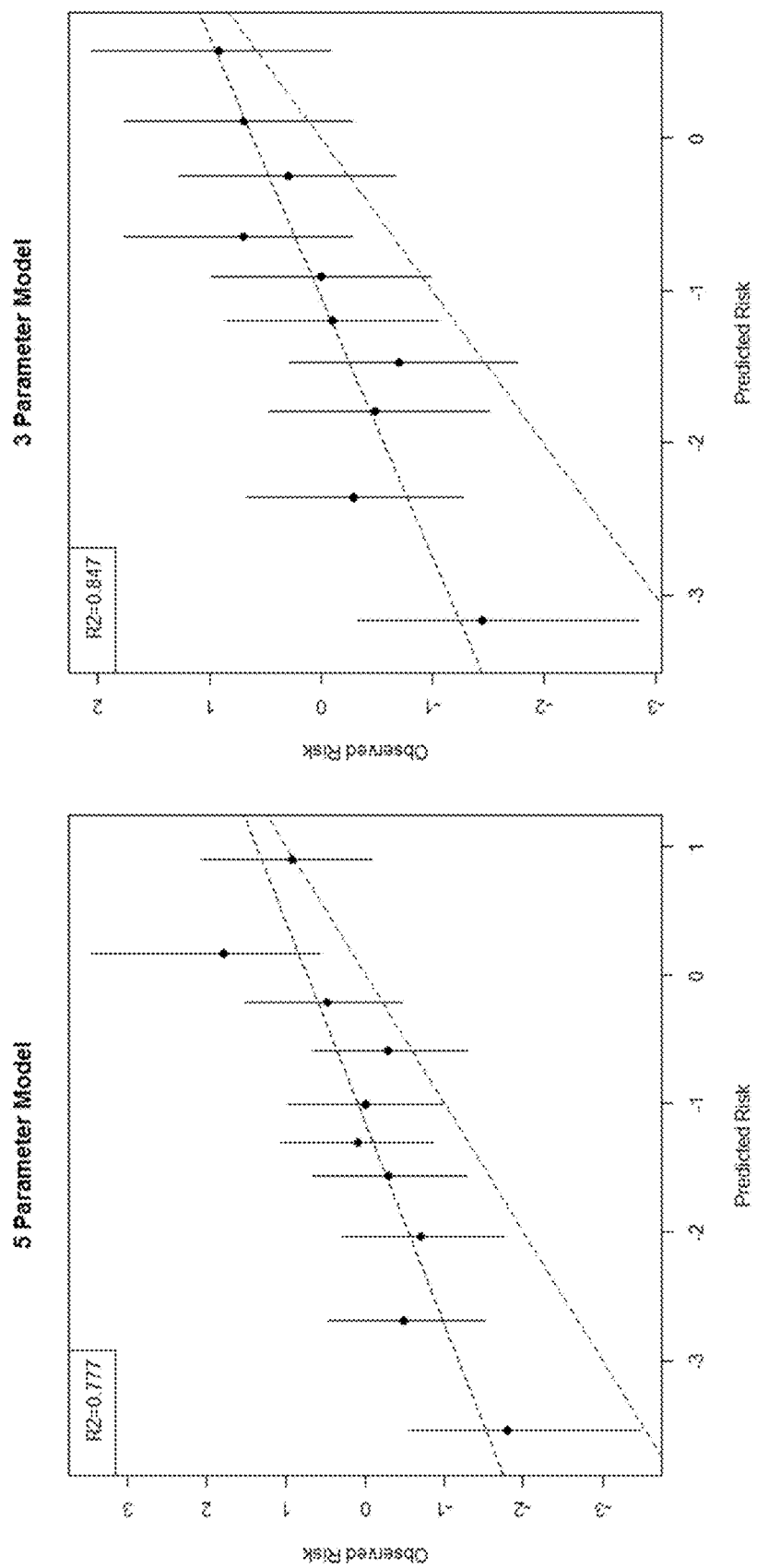
Fig. 56 Model Calibration

Fig. 57 Model Parameters

5 Parameter Model

```
Coefficients:
             Estimate Std. Error z value Pr(>|z|)
(Intercept)    1.6996     4.3544    0.39   0.6963
Age_Yr         0.0403     0.0154    2.62   0.0087 **
LN_SBP        -2.1065     0.8663   -2.43   0.0150 *
CAD            0.7824     0.3607    2.17   0.0301 *
ST2GTE35       1.3846     0.4384    3.16   0.0016 **
LN_NTBNP       0.4023     0.1668    2.41   0.0159 *
---
Signif. codes:  0 '***' 0.001 '**' 0.01 '*' 0.05 '.' 0.1 ' ' 1
```

3 Parameter Model

```
Coefficients:
             Estimate Std. Error z value Pr(>|z|)
(Intercept)   -8.3383     1.6970   -4.91  8.9e-07 ***
Age_Yr         0.0426     0.0144    2.96   0.0030 **
ST2GTE35       1.2656     0.4164    3.04   0.0024 **
LN_NTBNP       0.3998     0.1586    2.52   0.0117 *
---
Signif. codes:  0 '***' 0.001 '**' 0.01 '*' 0.05 '.' 0.1 ' ' 1
```

MULTIMARKER RISK STRATIFICATION

CLAIM OF PRIORITY

This application is a continuation of U.S. patent application Ser. No. 13/972,596, filed on Aug. 21, 2013 and claims priority to U.S. Provisional Patent Application Ser. No. 61/691,706, filed on Aug. 21, 2012. The entire contents of the foregoing are incorporated by reference herein.

TECHNICAL FIELD

The invention relates to methods for predicting risk of mortality, in subjects with cardiovascular disease, e.g., heart failure, based on multiple markers including a combination of biomarkers (e.g., ST2) and other clinical parameters (e.g., age).

BACKGROUND

Clinical evaluation for determination of risk of mortality due to heart failure may not always be straightforward. The decision whether to treat a subject aggressively or conservatively, or to admit the subject as an inpatient or to send them home, may sometimes be made solely on a physician's clinical assessment or "gut feeling" as to the individual's actual condition. A formula for determining a subject's likelihood of mortality would significantly enhance the physician's ability to make informed treatment decisions, improve patient care and reduce overall healthcare costs. A multi-marker approach for risk stratification has been generally proposed for patients with acute coronary syndromes, see, e.g., Sabatine et al., Circulation 105(15):1760-3 (2002)), and methods for predicting risk of a major adverse cardiac event are describe in U.S. Pat. No. 8,090,562.

SUMMARY

The present invention is based, at least in part, on the discovery that multiple markers, including serum levels of the biomarker ST2 (also known as Interleukin 1 Receptor Like 1 (IL1RL-1)), in combination with clinical parameters such as age and levels of at least one other biomarker, e.g., troponin or a natriuretic peptide (NP) such as the inactive N-terminal fragment of brain-type natriuretic peptide (NT-pro-BNP), can be used predict the likelihood of mortality due to CVD within a specific time period, e.g., 30 days, 3 or 6 months, or a year or more (e.g., 2, 5 or 10 years).

Provided herein are methods of evaluating the risk of mortality for a subject (e.g., a subject having or diagnosed with heart failure) within a specific time period (e.g., within 3 months, 6 months, or a year or more (e.g., 2, 5, or 10 years)that include determining a multimarker mortality risk score for a subject based upon the age of the subject; the level of ST2 in the subject, in combination with one or more of a natural logarithm of a level of a brain natriuretic peptide (BNP) in the subject; a level of troponin in the subject; a New York Heart Association (NYHA) score; a history of cardiovascular disease (CAD); a natural logarithm of a systolic blood pressure; a measure of renal function or a natural logarithm of a level of hemoglobin (Hgb), and age; and comparing the multimarker mortality risk score to a reference multimarker mortality risk score; wherein the presence of a multimarker mortality risk score that is at or above the reference multimarker mortality risk score indicates that the subject has an increased risk of mortality within the specific time period, and the presence of a multimarker mortality risk score that is below the reference multimarker mortality risk score indicates that the subject has a decreased risk of mortality within the specific time period (e.g., within one year).

In some embodiments, the risk score is determined using one of the following algorithms:
 (1) AGE+ST2+ln_SBP+CAD+ln_NTpro-BNP
 (2) AGE+ST2+ln_NTpro-BNP
 (3) AGE+ST2+Troponin+NYHA
 (4) AGE+ST2+[Troponin OR NYHA]
 (5) AGE+ST2+[Troponin AND/OR NYHA]+ln_Hgb
 (6) AGE+ST2+[Troponin AND/OR NYHA]+ln_Hgb
 (7) AGE+ST2+[Troponin AND/OR NYHA]+ln_Hgb+ ln_SBP
 (8) AGE+ST2+[Troponin AND/OR NYHA]+ln_Hgb+ ln_SBP+ln_NTpro-BNP.

In some embodiments, the level of ST2 is determined and compared to a threshold and the presence of a level at or above the threshold is scored as "1" and the presence of a level below the threshold is scored as "0". In some embodiments, the threshold level of ST2 is 35 or 50 ng/mL. In some embodiments, algorithm (1) or (2) is used and the threshold level of ST2 is 35 ng/mL. In some embodiments, algorithm (3) or (4) is used and the threshold level of ST2 is 50 ng/mL. In some embodiments, the subject has been diagnosed with a cardiovascular disease (e.g., heart failure). In some embodiments, the reference multimarker mortality risk score represents a score corresponding to a low risk of death within a specific time period (e.g., within 3 months, 6 months, 1, 2, 5 or 10 years). In some embodiments, the sample contains serum, blood, plasma, urine, or body tissue.

In some embodiments, the subject has a BMI of 25-29, a BMI of ≥30, or renal insufficiency. Some embodiments further include discharging the subject or treating the subject on an inpatient basis based on the presence of an increased risk of mortality determined using any of the methods described herein. For example, a subject identified as having an increased risk of mortality within the specific time period (e.g., within 3 months, 6 months, 1, 2, 5 or 10 years) is treated on an inpatient basis (e.g., newly admitted to a hospital or continued hospitalization) or a subject identified as having a decreased risk of mortality within the specific time period (e.g., within 3 months, 6 months, 1, 2, 5 or 10 years) is discharged from a hospital or continued to be treated on an outpatient basis. Some embodiments further include selecting and/or performing increased cardiac monitoring (e.g., any of the examples of increased cardiac monitoring described herein or known in the art) on a subject identified as having an increased risk of mortality within the specific time period (e.g., using any of the methods described herein), or selecting and/or performing low frequency monitoring (e.g., cardiac monitoring) on a subject (e.g., greater than 6 months between examinations, greater than 9 months between examinations, or one year or greater between examinations) identified as having a reduced risk of mortality within the specific time period (e.g., using any of the methods described herein). As described herein, increased cardiac monitoring can be, e.g., the monitoring of cardiac function in a subject (e.g., electrocardiogram (e.g., ambulatory electrocardiography), chest X-ray, echocardiography, stress testing, computer tomography, magnetic resonance imaging, positron emission tomography, and cardiac catheterization) or the monitoring of levels of soluble ST2 in the subject over time. Increased cardiac monitoring can also include increased frequency of clinical visits (e.g., about once every month, once every two months, once every three months, once every four months, once every five months, or once every six months). Also provided are methods of selecting a treatment for a subject receiving a treatment for a cardiovascular disorder that include determining the subject's risk of mortality over a specific time period (e.g., within any of the time periods described herein, e.g., within 3 months, 6 months, 1, 2, 5 or 10 years) using any of the methods described herein, and selecting continuation of the treatment for a subject determined to have a reduced risk of mortality over the specific time period (e.g., using any of the methods described herein) or selecting a new (alternate) cardiovascular treatment for a subject determined to have an increased risk of mortality over the specific time period (e.g., using any of the methods described herein). As described herein, a new treatment can mean administration of a new combination therapeutic agents, administration of a new therapeutic agent, a different dosage of the previously administered therapeutic agent, a different frequency of administration of the previously administered therapeutic agent, or a different route of administration of the previously administered therapeutic agent. Some embodiments further include administering the selected treatment to a subject.

Also provided are methods of selecting a subject for a clinical study that include determining a subject's risk of mortality within a specific time period (e.g., any of the specific time periods described herein, e.g., within 3 months, 6 months, 1, 2, 5 or 10 years) (e.g., using any of the methods described herein) and selecting a subject determined to have an increased risk of mortality within the specific time period for participation in a clinical study.

Also provided herein are methods of determining whether a subject's risk of mortality (e.g., caused by a cardiovascular disorder) is increasing or decreasing over time. These methods include determining a first multimarker mortality risk score in a subject at a first time point (e.g., using any of the methods described herein), determining a second multimarker risk score in a subject at a second time point (e.g., using any of the methods described herein), comparing the second multimarker risk score to the first multimarker risk score, and identifying a subject having an elevated second multimarker risk score as compared to the first multimarker risk score as having an increasing risk of mortality over time or identifying a subject having a decreased second multimarker risk score as compared to the first multimarker risk score as having a decreasing risk of mortality over time.

Also provided are methods of determining the efficacy of a treatment for a cardiovascular disorder (e.g., heart failure) in a subject that include, determining a first multimarker risk score in a subject at a first time point (e.g., using any of the methods described herein), determining a second multimarker risk score in a subject at a second time point (e.g., using any of the methods described herein), where two or more doses of a treatment for a cardiovascular disorder (e.g., heart failure) are administered to the subject between the first and the second time points, comparing the second multimarker risk score to the first multimarker risk score, and identifying the treatment as effective in a subject having a decreased second multimarker risk score as compared to the first multimarker risk score, or identifying the treatment as not being effective in a subject having an elevated second multimarker risk score as compared to the first multimarker risk score. Some embodiments further include selecting the treatment identified as being effective in the subject, and/or continuing to administer the selected treatment to the subject.

Also provided are methods of selecting a treatment for a subject that include determining a first multimarker risk score for a subject at a first time point (e.g., using any of the methods described herein), determining a second multimarker risk score for a subject at a second time point (e.g., using any of the methods described herein), comparing the second multimarker risk score with the first multimarker risk score, and selecting inpatient treatment (e.g., initial hospital admission or continued inpatient treatment) for a subject having an elevated second multimarker risk score as compared to first multimarker risk score or selecting outpatient treatment (e.g., hospital discharge or continued outpatient treatment) for a subject having a decreased second multimarker risk score as compared to the first multimarker risk score. Some methods further include admitting the subject to the hospital, continuing inpatient treatment, discharging the subject, or continuing outpatient treatment based on the comparison of the second and first multimarker risk scores (e.g., as selected above).

Also provided are methods of selecting a treatment for a subject that include determining a first multimarker risk score for a subject at a first time point (e.g., using any of the methods described herein), determining a second multimarker risk score for a subject at a second time point (e.g., using any of the methods described herein), comparing the second multimarker risk score to the first multimarker risk score, and selecting increased cardiac monitoring for a subject having an elevated second multimarker risk score as compared to the first multimarker risk score or selecting low frequency monitoring (e.g., cardiac monitoring) (e.g., greater than 6 months between examinations, greater than 9 months between examinations, or one year or greater between examinations) for a subject having a decreased second multimarker risk score as compared to the first multimarker risk score. As described herein, increased cardiac monitoring can be, e.g., the monitoring of cardiac function in a subject (e.g., electrocardiogram (e.g., ambulatory electrocardiography), chest X-ray, echocardiography, stress testing, computer tomography, magnetic resonance imaging, positron emission tomography, and cardiac catheterization) or the monitoring of the levels of soluble ST2 in the subject over time. Increased cardiac monitoring can also include increased frequency of clinical visits (e.g., about once every month, once every two months, once every three months, once every four months, once every five months, or once every six months). Some methods further include administering the selected treatment to the subject.

Also provided are methods of selecting a treatment for a subject that include determining a first multimarker risk score in a subject at a first time point (e.g., using any of the methods described herein), determining a second multimarker risk score in the subject at a second time point (e.g., using any of the methods described herein), where a subject has been administered at least two doses of treatment (e.g., a treatment of a cardiovascular disease) between the first time point and the second time point, comparing the first multimarker risk score to the second multimarker risk score, and selecting a new treatment for a subject having an elevated second multimarker risk score as compared to the first multimarker risk score or selecting the same treatment for a subject having a decreased second multimarker risk score compared to the first multimarker risk score. Some embodiments further include administering the selected treatment to the subject. As described herein, a new treatment can mean administration of a new combination therapeutic agents, administration of a new therapeutic agent, a different dosage of the previously administered therapeutic agent, a different frequency of administration of the previously administered therapeutic agent, or a different route of administration of the previously administered therapeutic agent.

Also provided are methods of selecting a subject for participation in a clinical study of a treatment for cardiovascular disease that include determining a first multimarker risk score in a subject at a first time point (e.g., using any of the methods described herein), determining a second multimarker risk score in the subject at a second time point (e.g., using any of the methods described herein), and selecting a subject having an elevated second multimarker risk score as compared to first multimarker risk score for participation in a clinical study of a cardiovascular disease.

As used herein, a "sample" includes any bodily fluid or tissue, e.g., one or more of blood, serum, plasma, urine, and body tissue. In certain embodiments, a sample is a serum, plasma, or blood sample.

An antibody that "binds specifically to" an antigen, binds preferentially to the antigen in a sample containing other proteins.

The methods and kits described herein have a number of advantages. For example, the methods can be used to determine whether a patient should be admitted or held as an inpatient for further assessment, regardless of whether a definitive diagnosis has been made. For example, the methods can be used for risk stratification of a given subject, e.g., to make decisions regarding the level of aggressiveness of treatment that is appropriate for the subject, based on their multimarker risk score as determined by a method described herein. Better treatment decisions can lead to reduced morbidity and mortality, and better allocation of scarce health care resources. The methods described herein can be used to make general assessments as to whether a patient should be further tested to determine a specific diagnosis. The methods described herein can also be used for patient population risk stratification, e.g., to provide information about clinical performance or expected response to a therapeutic intervention. The methods described herein can be used regardless of the underlying cause or ultimate diagnosis, and therefore are not limited to specific indications.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting.

All publications, patent applications, patents, sequences, database entries, and other references mentioned herein are incorporated by reference in their entirety. In addition, the present application incorporates by reference the entire contents of U.S. patent application Ser. No. 11/789,169, and international patent application nos. PCT/US2007/067626, PCT/US2007/067914, and PCT/US2007/068024.

In case of conflict, the present specification, including definitions, will control.

Other features and advantages of the invention will be apparent from the following detailed description and Figures, and from the claims.

DESCRIPTION OF DRAWINGS

FIG. 1 shows the summary statistics for individual variables for 1 year-mortality.

FIG. 2 shows the summary statistics for individual variables for 5-year mortality.

FIGS. 3-24 show linearity checks and cut-point evaluations performed for each variable.

FIGS. 25 and 26 provide a summary of the results for each variable.

FIGS. 27-34 show the results of several heuristic approaches used to identify the best models for predicting risk of death, including backward, forward, and stepwise selection. Selection in each instance was made based on AIC (Akaike's Information Criteria) or BIC (Bayesian Information Criteria).

FIG. 35 shows the co-linearity analysis of several variables with risk of death.

FIG. 36 is a summary of the univariate performance of each variable.

FIGS. 37-49 show the results of linearity checks performed for each variable.

FIG. 50 provides a summary of the results for each variable.

FIG. 51 shows AIC-based marker selection.

FIG. 52 shows BIC-based marker selection.

FIGS. 53 and 54 show a comparison of two models ([Age+Ln_SBP+CAD+ST2>=35+LN_NTBNP] and [Age+ST2>=35+LN_NTBNP].

FIG. 55 shows bootstrap AUC estimates for the 5-parameter and the 3-parameter model.

FIG. 56 is a graph showing the model calibration for the 5-parameter and the 3-parameter model.

FIG. 57 is list of exemplary model parameters.

DETAILED DESCRIPTION

Clinical evaluation of patients, particularly patients with non-specific symptoms such as dyspnea or chest pain, is often challenging. The results described herein provide evidence that multimarker risk scores based on multiple markers including the subject's age and levels of ST2, plus additional clinical parameters including one or more of: systolic blood pressure, the presence of coronary artery disease, New York Heart Association (NYHA) score, measures of renal function, levels of troponin and/or levels of NT-proBNP are useful in the prognostic evaluation of patients, regardless of the underlying cause of their disease. The multimarker risk score is a powerful indicator of severe disease and imminent death, as demonstrated herein in several different heart failure populations.

Predicting Death

As demonstrated herein, an algorithm that takes into account multiple markers including elevated concentrations of soluble ST2 and the subject's age can be used to accurately predict a subject's risk of death within a specific time period (e.g., within 3 months, within six months, within 1, 2, 5 or 10 years).

General Methodology—Determining a Subject's Multimarker Risk Score

In general, the methods described herein include determining the values for each of the markers in the risk algorithm, including evaluating the levels (e.g., levels in blood, serum, plasma, urine, or body tissue) of soluble ST2 in a subject, e.g., a mammal, e.g., a human; determining the subject's age, e.g., by querying the subject or the subject's family friends, or medical records; and one or more of the following: determining the subject's history of coronary artery disease, e.g., by querying the subject or the subject's family friends, or medical records, or using routine diagnostic methods; determining the subject's systolic blood pressure (SBP); and/or determining one or more of a level of Troponin; NTpro-BNP; NYHA score; and renal function.

These markers, in combination, provide information regarding the subject's likelihood of mortality, e.g., within a specific time period, e.g., within 3 months, 6 months, 1, 2, 5 or 10 years.

Evaluating circulating levels of a marker such as soluble ST2, NTpro-BNP, or troponin in a subject typically includes obtaining a biological sample, e.g., serum, plasma or blood, from the subject. Levels of a marker in the sample can be determined by measuring levels of polypeptide in the sample, using methods known in the art and/or described herein, e.g., immunoassays such as enzyme-linked immunosorbent assays (ELISA). For example, in some embodiments a monoclonal antibody is contacted with the sample; binding of the antibody is then detected and optionally quantified, and levels of the protein are determined based on levels of antibody binding. Alternatively, levels of mRNA can be measured, again using methods known in the art and/or described herein, e.g., by quantitative PCR or Northern blotting analysis.

In some embodiments, the marker levels or values can then be used in an algorithm to determine a multimarker risk score, e.g., an algorithm determined based on statistical analysis of a subject population. Exemplary algorithms include the following:

(1) AGE+ln_SBP+CAD+ST2+ln_NTpro-BNP
(2) AGE+ST2+ln_NTpro-BNP

In these embodiments, the level of soluble ST2 is determined and compared to a threshold, e.g., 35 or 50 ng/mL, and the presence of a level at or above the threshold is scored as "1" and the presence of a level below the threshold is scored as "0". In some embodiments, in algorithms (1) and (2) the threshold level of soluble ST2 is 35 ng/mL.

(3) AGE+ST2+Troponin+NYHA
(4) AGE+ST2+[Troponin OR NYHA]

In some embodiments, the level of soluble ST2 is determined and compared to a threshold, e.g., 35 or 50 ng/mL, and the presence of a level at or above the threshold is scored as "1" and the presence of a level below the threshold is scored as "0". In some embodiments, in algorithms (3) or (4) the threshold level of ST2 is 50 ng/mL.

In some embodiments, the level of hemoglobin (Hgb) is also determined, e.g., in an algorithm comprising:

(5) AGE+ST2+[Troponin AND/OR NYHA]+ln_Hgb

In some embodiments, the NYHA score is determined, and the presence of an NYHA score at or above a threshold is scored as "1" and the presence of a level below the threshold is scored as "0". In some embodiments, in algorithms (3) or (4) or (5) the threshold score is 3.

In some embodiments, the level of troponin is determined and compared to a threshold, e.g., a level that represents a threshold below which healthy individuals fall, and above which individuals are identified as having a cardiovascular condition, e.g., 35 or 50 pg/mL, and the presence of a level at or above the threshold is scored as "1" and the presence of a level below the threshold is scored as "0". In some embodiments, in algorithms (3) or (4) or (5) the threshold level of troponin is 16 pg/mL.

In some embodiments, the multimarker risk score is calculated using a computing device, e.g., a personal computer.

Once a multimarker risk score has been determined, the multimarker risk score can be compared to a reference score. In some embodiments, the reference score will represent a threshold level, above which the subject has an increased risk of death, and/or has a severe disease. The reference score chosen may depend on the methodology used to measure one or more of the markers, e.g., the levels of soluble ST2. For example, in some embodiments, where circulating levels of soluble ST2 are determined using an immunoassay, e.g., as described herein, and a score above that reference level indicates that the subject has an increased risk of death.

A reference score can also be a multimarker risk score calculated for a healthy subject (e.g., a subject not diagnosed with a cardiovascular disorder (e.g., not diagnosed with heart failure) or not presenting with two or more symptoms of a cardiovascular disorder). A reference score can also be a multimarker risk score calculated for a subject not diagnosed with a cardiovascular disorder (e.g., not diagnosed with heart failure), not presenting with two or more symptoms of a cardiovascular disorder, and not identified as having an increased risk of developing a cardiovascular disorder (e.g., no family history of a cardiovascular disease).

In some embodiments, more than one multimarker risk score is determined using a method described herein, and a change in the score indicates whether the subject has an increased or decreased risk of death. A score that increases means that the subject has an increasing risk of imminent death, e.g., an increasingly poor prognosis, and that a treatment is not working or should be changed or initiated. A score that decreases over time indicates that the subject has a decreasing risk of imminent death, e.g., an increasingly positive prognosis, and can be indicative of the efficacy of a treatment, for example, and the treatment should be continued, or, if the score becomes low enough, possibly discontinued. As one example, increasing scores may indicate a need for more aggressive treatment or hospitalization (e.g., initial admission or hospitalization in a more acute setting, e.g., in an intensive care unit, or the use of telemetry or other methods for monitoring the subject's cardiac status), while decreasing scores may indicate the possibility of less aggressive treatment, a short hospitalization, or discharge. This information allows a treating physician to make more accurate treatment decisions; for example, the subject may be admitted to the hospital as an inpatient, e.g., in an acute or critical care department.

Additional testing can be performed, e.g., to determine the subject's actual condition. More aggressive treatment may be administered either before or after additional testing. For example, in the case of a suspected myocardial infarction (MI), the subject may be sent for more extensive imaging studies and/or cardiac catheterization.

In some embodiments, the methods include the use of additional diagnostic methods to identify underlying pathology. Any diagnostic methods known in the art can be used, and one of skill in the art will be able to select diagnostic methods that are appropriate for the subject's symptoms. In some embodiments, the methods described herein include other diagnostic methods in addition to or as an alternative to the measurement of other biomarkers, e.g., physical measurements of lung function or cardiac function as are known in the art.

In some examples, a subject who has been identified as having an elevated risk of mortality (or one or more of the subject's immediate family members) is informed of the symptoms of a cardiovascular disorder (e.g., symptoms of heart failure or MI) and/or are instructed to monitor the subject for the development or occurrence of one or more symptoms of cardiovascular disease (e.g., heart failure or MI). In some examples, one or more lineal family members of a subject identified as having an elevated risk of mortality are also tested for the presence of a cardiovascular disorder (e.g., heart failure) or methods are performed on such family members to determine their risk of cardiovascular disease or their risk of mortality (e.g., using any of the methods described herein).

ST2

The ST2 gene is a member of the interleukin-1 receptor family, whose protein product exists both as a trans-membrane form, as well as a soluble receptor that is detectable in serum (Kieser et al., FEBS Lett. 372(2-3):189-93 (1995); Kumar et al., J. Biol. Chem. 270(46):27905-13 (1995); Yanagisawa et al., FEBS Lett. 302(1):51-3 (1992); Kuroiwa et al., Hybridoma 19(2):151-9 (2000)). ST2 was described to be markedly up-regulated in an experimental model of heart failure (Weinberg et al., Circulation 106(23):2961-6 (2002)), and preliminary results suggest that ST2 concentrations may be elevated in those with chronic severe HF (Weinberg et al., Circulation 107(5):721-6 (2003)) as well as in those with acute myocardial infarction (MI) (Shimpo et al., Circulation 109(18):2186-90 (2004)).

The trans-membrane form of ST2 is thought to play a role in modulating responses of T helper type 2 cells (Lohning et al., Proc. Natl. Acad. Sci. U.S.A. 95(12):6930-5 (1998); Schmitz et al., Immunity 23(5):479-90 (2005)), and may play a role in development of tolerance in states of severe or chronic inflammation (Brint et al., Nat. Immunol. 5(4):373-9 (2004)), while the soluble form of ST2 is up-regulated in growth stimulated fibroblasts (Yanagisawa et al., 1992, supra). Experimental data suggest that the ST2 gene is markedly up-regulated in states of myocyte stretch (Weinberg et al., 2002, supra) in a manner analogous to the induction of the BNP gene (Bruneau et al., Cardiovasc. Res. 28(10):1519-25 (1994)).

Tominaga, FEBS Lett. 258:301-304 (1989), isolated murine genes that were specifically expressed by growth stimulation in BALB/c-3T3 cells; they termed one of these genes ST2. The ST2 gene encodes two protein products: ST2, which is a soluble secreted form; and ST2 L, a transmembrane receptor form that is very similar to the interleukin-1 receptors. The HUGO Nomenclature Committee designated the human homolog, the cloning of which was described in Tominaga et al., Biochim. Biophys. Acta. 1171:215-218 (1992), as Interleukin 1 Receptor-Like 1 (IL1RL1). The two terms are used interchangeably herein.

The mRNA sequence of the shorter, soluble isoform of human ST2 can be found at GenBank Acc. No. NM 003856.2, and the polypeptide sequence is at GenBank Acc. No. NP_003847.2; the mRNA sequence for the longer form of human ST2 is at GenBank Acc. No. NM_016232.4; the polypeptide sequence is at GenBank Acc. No. NP_057316.3. Additional information is available in the public databases at GeneID: 9173, MIM ID #601203, and UniGene No. Hs.66. In general, in the methods described herein, the soluble form of ST2 polypeptide is measured.

Methods for detecting and measuring ST2 are known in the art, e.g., as described in U.S. Pat. Pub. Nos. 2003/0124624, 2004/0048286 and 2005/0130136, the entire contents of which are incorporated herein by reference. Kits for measuring ST2 polypeptide are also commercially available, e.g., the ST2 ELISA Kit manufactured by Medical & Biological Laboratories Co., Ltd. (MBL International Corp., Woburn, Mass.), no. 7638. In addition, devices for measuring ST2 and other biomarkers are described in U.S. Pat. Pub. No. 2005/0250156.

Other Biomarkers and Clinical Variables

The methods described herein can also include measuring levels of other biomarkers or clinical variables in addition to ST2, including troponin and NT-proBNP. Other markers or clinical variables can also be determined, e.g., age, blood pressure, gender, diabetes status, smoking status, CRP, IL-6, D-dimers, BUN, liver function enzymes, albumin, measures of renal function, e.g., creatinine, creatinine clearance rate, or glomerular filtration rate, and/or bacterial endotoxin. Methods for measuring these biomarkers are known in the art, see, e.g., U.S. Pat. Pub. Nos. 2004/0048286 and 2005/0130136 to Lee et al.; Dhalla et al., Mol. Cell. Biochem. 87:85-92 (1989); Moe et al., Am. Heart. J. 139:587-95 (2000); Januzzi et al., Eur. Heart J. 27(3):330-7 (2006); Maisel et al., J. Am. Coll. Cardiol. 44(6):1328-33 (2004); and Maisel et al., N. Engl. J. Med. 347(3):161-7 (2002), the entire contents of which are incorporated herein by reference. Liver function enzymes include alanine transaminase (ALT); aspartate transaminase (AST); alkaline phosphatase (ALP); and total bilirubin (TBIL).

In these embodiments, a multimarker risk score and levels of one or more additional biomarkers are determined, and the information from the score and a comparison of the biomarkers with their respective reference levels provides additional information regarding the subject's risk of death, which may provide more accurate and specific information regarding the subject's risk. The levels can then be compared to a reference level, e.g., a threshold at or above which the subject has an increased risk of death.

Selecting a Treatment—Aggressive vs. Conservative

Once it has been determined that a subject has a multimarker risk score above a predetermined reference score, the information can be used in a variety of ways. For example, if the subject has an elevated score, e.g., as compared to a reference level, a decision to treat aggressively can be made, and the subject can be, e.g., admitted to a hospital for treatment as an inpatient, e.g., in an acute or critical care department. Portable test kits could allow emergency medical personnel to evaluate a subject in the field, to determine whether they should be transported to the ED. Triage decisions, e.g., in an ED or other clinical setting, can also be made based on information provided by a method described herein. Those patients with high scores can be prioritized over those with lower scores. Additional methods for selecting a treatment for a subject based on the determination of a subject's risk or mortality (based on a single multimarker risk score or a first and second multimarker risk score determined for the subject) (e.g., using any of the methods described herein) are known in the art and described herein, e.g., in the Summary section above. Some examples of any of the methods of selecting a treatment described herein further include modifying the subject's clinical file (e.g., a computer-readable medium) to indicate that the subject should be administered the selected treatment, admitted to the hospital, discharged from the hospital, continue to be hospitalized, continue to be treated on an outpatient basis, receive cardiac monitoring (e.g., any of the cardiac monitoring methods described herein), or receive low frequency monitoring (e.g., any of the low frequency monitoring methods described herein) (as determined using any of the methods described herein). Additional methods include administering or performing the selected treatment on a subject.

The methods described herein also provide information regarding whether a subject is improving, e.g., responding to a treatment, e.g., whether a hospitalized subject has improved sufficiently to be discharged and followed on an outpatient basis. In general, these methods will include determining a multimarker risk score for the subject multiple times. A decrease in multimarker risk score over time indicates that the subject is likely to be improving. The most recent multimarker risk score can also be compared to a reference score, as described herein, to determine whether the subject has improved sufficiently to be discharged.

The subject may also be considered for inclusion in a clinical trial, e.g., of a treatment that carries a relatively high risk. The subject can be treated with a regimen that carries a relatively higher risk than would be considered appropriate for someone who had a lower risk of imminent death, e.g., death within 30 days or within 1 year of presentation.

Beyond the clinical setting, information regarding a subject's multimarker risk score can be used in other ways, e.g., for payment decisions by third party payors, or for setting medical or life insurance premiums by insurance providers. For example, a high multimarker risk score, e.g., a score at or above a predetermined threshold score, may be used to decide to increase insurance premiums for the subject.

Patient Populations

The methods described herein are useful in the clinical context of patients with a cardiovascular disorder (e.g., heart failure). As one example, a multimarker risk score can be determined at any time, and if the multimarker risk score is elevated, the health care provider can act appropriately. In some embodiments, the methods described herein are used in subjects who have heart failure (HF), e.g., acute decompensated, e.g., heart failure (ADHF) or chronic heart failure (CHF); methods of diagnosing HF and ADHF are known in the art.

Computer-Implemented Methods

Any of the methods described herein can be implemented in a system. For example, a system can include a processor, memory, and a storage device. The memory can include an operating system (OS), such as Linux, UNIX, or Windows® XP, a TCP/IP stack for communicating with a network (not shown), and a process for calculating one or more multimarker risk score(s) in accordance with the methods described in this document and also, optionally, comparing a second determined multiple marker risk score from a subject at a first time point with a first multiple marker risk score determined at a first time point or comparing a determined multiple marker risk score with a reference value (e.g. a multiple marker risk score of a healthy subject). In some implementations, the system also includes a link to an input/output (I/O) device for display of a graphical user interface (GUI) to a user. In some implementations, the system is in communication with a user interface which allows a person to enter clinical information about the patient.

In some implementations, the calculating of the one or more multimarker risk score functionality can be implemented within a network environment. For example, a networking environment can provide users (e.g., individuals such as clinicians) access to information collected, produced, and/or stored. Various techniques and methodologies can be implemented for exchanging information between the users and processor. For example, one or more networks (e.g., the Internet) may be employed for interchanging information with user devices. Various types of computing devices and display devices may be employed for information exchange. For example, hand-held computing devices (e.g., a cellular telephone, tablet computing device, etc.) may exchange information through one or more networks (e.g., the Internet) with the processor. Other types of computing devices such as a laptop computer and other computer systems may also be used to exchange information with the process for calculating the one or more multiple marker risk score(s). A display device such as a liquid crystal display (LCD) television or other display device may also present information from processor. One or more types of information protocols (e.g., file transfer protocols, etc.) may be implemented for exchanging information. The user devices may also present one or more types of interfaces (e.g., graphical user interfaces) to exchange information between the user and the processor. For example, a network browser may be executed by a user device to establish a connection with a website (or webpage) of the processor and provide a vehicle for exchanging information. The processor can include software and hardware configured to calculate one or more multimarker risk score(s) in a subject (e.g., using any of the methods described in this document).

Operations can further include providing an output as a result of the subject's risk of mortality or change in risk of mortality. The output can be provided, for example, by displaying a representation of the output on a display device, or storing data representing the output on a computer-readable non-transitory storage device. The output can identify one or more treatments (e.g., any of the treatments described herein) that are selected for the subject, identify a treatment as being effective or not effective in the subject, select a subject for participation in a clinical study, or identify a subject as having an increased, decreased, increasing, or decreasing risk of mortality within a specific time period (e.g., according to any of the methods described herein).

In some examples, a computer device or mobile computer device can be used to implement the techniques described herein. For example, a portion or all of the operations of a comfort modeler may be executed by a computer device (located, for example, within the processor) and/or by the mobile computer device (that may be operated by an end user). Computing device is intended to represent various forms of digital computers, including, e.g., laptops, desktops, workstations, personal digital assistants, servers, blade servers, mainframes, and other appropriate computers. Computing device is intended to represent various forms of mobile devices, including, e.g., personal digital assistants, cellular telephones, smartphones, and other similar computing devices. The components shown here, their connections and relationships, and their functions, are meant to be examples, and are not meant to limit implementations of the methods described and/or claimed in this document.

A computing device can include a processor, a memory, a storage device, a high-speed interface connecting to memory and high-speed expansion ports, and a low speed interface connecting to a low speed bus and a storage device. Each of these components can be interconnected using various busses, and can be mounted on a common motherboard or in other manners as appropriate. The processor can process instructions for execution within the computing device, including instructions stored in memory or on storage device to display graphical data for a GUI on an external input/output device, including, e.g., a display coupled to a high speed interface. In other implementations, multiple processors and/or multiple busses can be used, as appropriate, along with multiple memories and types of memory. Also, multiple computing devices can be connected, with each device providing portions of the necessary operations (e.g., as a server bank, a group of blade servers, or a multiprocessor system).

A memory that stores data can be within the computing device. In one implementation, the memory is a volatile memory unit or units. In another implementation, memory is a non-volatile memory unit or units. The memory can also can be another form of non-transitory computer-readable medium, including, e.g., a magnetic or optical disk.

The storage device can be capable of providing mass storage for the computing device. In one implementation, the storage device can be or contain a non-transitory computer-readable medium, including, e.g., a floppy disk device, a hard disk device, an optical disk device, or a tape device, a flash memory or other similar solid state memory device, or an array of devices, including devices in a storage area network or other configurations. A computer program product can be tangibly embodied in a data carrier. The computer program product also can contain instructions that, when executed, perform one or more methods, including, e.g., those described herein. The data carrier can be a computer- or machine-readable medium, including, e.g., memory, storage device, memory on a processor, and the like.

A high-speed controller can be used to manage bandwidth-intensive operations for the computing device, while the low speed controller can manage lower bandwidth-intensive operations. Such allocation of functions is an example only. In one implementation, a high-speed controller can be coupled to a memory, a display (e.g., through a graphics processor or accelerator), and to a high-speed expansion ports, which can accept various expansion cards (not shown). In the implementation, the low-speed controller can be coupled to a storage device and a low-speed expansion port. The low-speed expansion port, which can include various communication ports (e.g., USB, Bluetooth®, Ethernet, wireless Ethernet), can be coupled to one or more input/output devices, including, e.g., a keyboard, a pointing device, a scanner, or a networking device including, e.g., a switch or router, e.g., through a network adapter.

As is known in the art, a computing device can be implemented in a number of different forms. For example, it can be implemented as standard server, or multiple times in a group of such servers. It also can be implemented as part of a personal computer including, e.g., laptop computer. In some examples, components from the computing device can be combined with other components in a mobile device (not shown), including, e.g., device. Each of such devices can contain one or more of computing device(s), and an entire system can be made up of multiple computing devices that communicate with each other.

A computing device can include a processor, a memory, an input/output device including, e.g., a display, a communication interface, and a transceiver, among other components. The device also can be provided with a storage device, including, e.g., a microdrive or other device, to provide additional storage. Each of these components can be interconnected using various busses, and several of the components can be mounted on a common motherboard or in other manners as appropriate.

The processor can execute instructions within the computing device, including instructions stored in the memory. The processor can be implemented as a chipset of chips that include separate and multiple analog and digital processors. The processor can provide, for example, for coordination of the other components of the device, including, e.g., control of user interfaces, applications run by the device, and wireless communication by the device.

The processor can communicate with a user through a control interface and a display interface coupled to the display. The display can be, for example, a TFT LCD (Thin-Film-Transistor Liquid Crystal Display) or an OLED (Organic Light Emitting Diode) display, or other appropriate display technology. The display interface can include appropriate circuitry for driving display to present graphical and other data to a user. The control interface can also receive commands from a user and convert them for submission to processor. In addition, an external interface can communicate with processor, so as to enable near area communication of device with other devices. The external interface can provide, for example, for wired communication in some implementations, or for wireless communication in other implementations, and multiple interfaces also can be used.

The memory can store data within the computing device. The memory can be implemented as one or more of a computer-readable medium or media, a volatile memory unit or units, or a non-volatile memory unit or units. An expansion memory can also be provided and connected to the device through an expansion interface, which can include, for example, a SIMM (Single In Line Memory Module) card interface. Such expansion memory can provide extra storage space for the device, or also can store applications or other data for the device. Specifically, the expansion memory can include instructions to carry out or supplement the processes described above, and can also include secure data. Thus, for example, the expansion memory can be provided as a security module for the device, and can be programmed with instructions that permit secure use of the device. In addition, secure applications can be provided through the SIMM cards, along with additional data, including, e.g., placing identifying data on the SIMM card in a non-hackable manner.

The memory can include, for example, flash memory and/or NVRAM memory, as discussed below. In one implementation, a computer program product is tangibly embodied in a data carrier. The computer program product contains instructions that, when executed, perform one or more methods, including, e.g., any of the methods described herein. The data carrier is a computer- or machine-readable medium, including, e.g., memory, expansion memory, and/or memory on a processor that can be received, for example, over a transceiver or an external interface.

The device can communicate wirelessly through a communication interface, which can have multimarker risk score calculating circuitry where necessary, or where desired. The communication interface can provide for communications under various modes or protocols, including, e.g., GSM voice calls, SMS, EMS, or MMS messaging, CDMA, TDMA, PDC, WCDMA, CDMA2000, or GPRS, among others. Such communication can occur, for example, through a radio-frequency transceiver. In addition, short-range communication can occur, including, e.g., using a Bluetooth®, WiFi, or other such transceiver (not shown). In addition, a GPS (Global Positioning System) receiver module can provide additional navigation- and location-related wireless data to the device, which can be used as appropriate by applications running on the device.

The device can also communicate audibly using an audio codec, which can receive spoken data from a user and convert it to usable digital data. The audio code can likewise generate audible sound for a user, including, e.g., through a speaker, e.g., in a handset of device. Such sound can include sound from voice telephone calls, can include recorded sound (e.g., voice messages, music files, and the like) and also can include sound generated by applications operating on the device.

As is known in the art, the computing device can be implemented in a number of different forms. For example, it can be implemented as cellular telephone. It also can be implemented as part of smartphone, personal digital assistant, or other similar mobile device.

Various implementations of any of the systems and methods described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a display device (e.g., a CRT (cathode ray tube) or LCD (liquid crystal display) monitor) for displaying data to the user and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input. Any of the systems and methods described herein can be implemented in a computing system that includes a back end component (e.g., as a data server), or that includes a middleware component (e.g., an application server), or that includes a front end component (e.g., a client computer having a user interface or a Web browser through which a user can interact with an implementation of any of the systems and methods described herein), or a combination of such back end, middleware, or front end components. The components of the system can be interconnected by a form or medium of digital data communication (e.g., a communication network). Examples of communication networks include: a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

EXAMPLES

The invention is further described in the following examples, which do not limit the scope of the invention described in the claims.

Example 1

Predictive Model Based on Barcelona Study

The objective of this example was to construct a model of heart failure from data in the Barcelona Cohort, to predict 1 Year Mortality and Study (5 Year) Mortality.

Summary of study. The Barcelona Study was a prospective, blinded study of 891 ambulatory patients referred to the Heart Failure unit integrated into a tertiary-care hospital. Most patients were referred from cardiology (70.5%) and internal medicine (15.1%); 5% come from the emergency room or short-stay unit. Admissions from primary care clinics were few.

Enrollment criteria. Patients were enrolled who had either been referred to the Heart Failure unit for Heart Failure, independent of etiology, or who had severely depressed ventricular function following acute myocardial infarction (AMI).

Patient assessment. All subjects underwent a clinical assessment that included relevant history, detailed physical examination, echocardiogram, and blood work-up. A diagnosis of heart failure was confirmed by physician clinical assessment.

Biochemical sampling information. Venous blood samples were obtained at study enrollment, processed, and stored at $-80°$ C. until time of the Presage ST2 Assay measurement.

This study conformed to the principles of the Declaration of Helsinki and was approved of by the local ethical committees. All participants provided written, informed consent.

Clinical Program Study Cohort. All of the 891 participants of the Barcelona study were included in the Presage ST2 Assay Clinical Program Study Cohort. Across these patients, 78 patients (8.8%) reached the end point of all-cause mortality within one year.

The models were created based on the following quantitative variables: Age; ST2; left ventricular ejection fraction (LVEF); body mass index (BMI); NT-proBNP; Troponin (cTnT1); Creatinine; Estimated Glomerular Filtration Rate (eGFR); systolic blood pressure (SBP); diastolic blood pressure (DBP); and Hemoglobin (Hgb), and the following discrete variables: New York Heart Association (NYHA) score; Ethnicity; Sex; history of Coronary Artery Disease (CAD); Diabetes; and hypertension (HTN).

The following statistical measures were made: Median's [IQR]; Differences between Events and Censored; Standardized HR—raw and In transformed; AUC; Normality Test (Shapiro Wilks Test). Discrete variables were evaluated with counts and HR. The results are shown in FIGS. 1 and 2. Linearity Checks and Cut-point Evaluations were also performed, see FIGS. 3-24, with a summary in FIG. 25. Based on this analysis, a set of variables was defined that included the variables shown in FIG. 26.

The model was constructed by analysis of all combinations of the variables shown in FIG. 26, and all models of size 1-5 were selected. Fit parameters (e.g. AIC and BIC) were estimated, as was discrimination (AUC). An estimate of over-fit was made using bootstrap analysis. A 3 or 5 parameter model was selected to reduce the likelihood of overfit unless there is a systematic bias in the data set.

Several heuristic approaches were used to identify the best models, including backward, forward and stepwise selection, and selection was made based on AIC (Akaike's Information Criteria) or BIC (Bayesian Information Criteria).

The results are shown in FIGS. 27-34. For the 1-year outcome models, the best small models consist of Age, ST2, Troponin and NYHA>=3 with a bootstrapped performance of ~0.79; 3 parameter models contain ST2, Age+1 other marker with a bootstrapped performance of ~0.78. Marker selection based on AIC resulted in models that were over-fit. Marker selection based on BIC consisted of Troponin, Age, ST2>=50, NYHA>=3, Troponin>=16, and Hgb, with a bootstrapped performance of ~0.80. For the study outcomes, the best small models consist of Age, ST2>=50, Troponin and NYHA >=3+1 marker with a bootstrapped performance of 0.81-0.82; 3 parameter models contain Age (10), ST2 (8), Troponin (7), or NHYA (5) with a bootstrapped performance of 0.79-0.80. Marker selection based on AIC again resulted in models that were over-fit, and marker selection based on BIC consisted of Troponin, ST2, Age, and NYHA>=3 with a bootstrapped performance of 0.79-0.80.

Example 2

Predictive Model Based on PRIDE Study

The objective of the study described in this example was to develop an algorithm capable of predicting 1 year mortality in subjects that are ADHF positive. There were 148 Controls and 61 Cases; the data set is sufficient to support a model of 3-6 parameters.

Summary of Parent Study. The PRoBNP Investigation of Dyspnea in the Emergency Department study (PRIDE) was a prospective, blinded study of 599 dyspneic subjects presenting to the Emergency Department (ED) of the Massachusetts General Hospital, in Boston, Mass. PRIDE was performed for the purpose of validating use of NT-proBNP testing (using the predicate device Elecsys ProBNP, Roche Diagnostics, Indianapolis, Ind.). The complete selection criteria and design of the PRIDE study have been described previously in peer-reviewed publications (Januzzi et al. 2005, Januzzi et al. 2006).

Enrollment criteria. Original PRIDE enrollment criteria included all patients at least 21 years of age presenting to the ED with complaints of dyspnea.

Original exclusion criteria were dyspnea following blunt or penetrating trauma to the chest, renal failure (serum creatinine >2.5 mg/dl), ST elevation myocardial infarction, or electrocardiographic changes diagnostic of acute coronary ischemia, such as ST segment depression or transient ST segment elevation in the presence of symptoms suggestive of coronary artery disease.

Other exclusions included treatment with an acute dose (non-maintenance therapy) of a loop diuretic more than two hours prior to enrollment, and patient unwillingness or inability to provide written informed consent (or site otherwise unable to obtain informed consent from available next of kin).

Patient Assessment. Diagnosis was recorded by the ED physician as well as by the attending physician following admission, both blinded to the biomarker concentrations. In the event of a disagreement between the two primary physicians, two of the three cardiologists involved in the study adjudicated patient diagnosis as either congestive heart failure or dyspnea due to non-cardiac cause.

Using these criteria, 599 patients were enrolled at the single site. Of the 599 patients, 209 (34.8%) had an adjudicated diagnosis of congestive heart failure. All patients were monitored for one year for all cause mortality.

Biochemical sampling information. Blood samples (EDTA plasma) were collected at presentation and stored at −80° C. for analysis until the time of the Presage ST2 Assay measurement.

All participants provided written, informed consent, and the PRIDE protocol was approved by the participating Institutional Review Board.

Presage ST2 Assay Clinical Program Cohort. The Clinical Program includes only the 209 patients diagnosed with acute heart failure, using the all cause mortality endpoint. Across these patients, 61 patients (29.1%) reached the end point of all cause mortality within one year.

The potential parameters included measurements of ST2, NT-proBNP, Troponin, Age, Renal Function (Creatinine or eGFR), Hemoglobin, and Blood Pressure (e.g., systolic or diastolic BP). Additional parameters included Gender, Ethnicity, BMI, Hypertension, Diabetes, CAD, and C-reactive protein (CRP).

The modeling approach was based on logistic regression, which is a linear model with an output of the log odds of having an event, and is directly related to probability of an event (i.e. risk). The following assumptions were made: a linear relationship between risk (y) and X; the markers included in the model are mutually exclusive (independent or not co-linear; a correlation coefficient around 0.7 or higher is usually considered as evidence of colinearity); the markers should be collectively exhaustive (though this assumption is typically relaxed as it is difficult to know what markers might be missing).

Covariance among the markers was evaluated, as was linearity of the response to risk. Transforms or non-linear terms were considered, and the markers were combined and selected under a bootstrap analysis to estimate true performance. The model performance was also evaluated under a bootstrap analysis.

The results of the colinearity analysis are shown in FIG. 35; no significant colinearity was found, except among the markers of renal function. Univariate performance of the various markers is shown in FIG. 36. Results of the linearity check are shown in FIGS. 37-49. A summary of the results and variables is shown in FIG. 50.

The model was then created. Missing values were imputed to strengthen the data set, and markers were selected within a bootstrap loop, using forward selection, backward selection, stepwise forward, and stepwise backward selection. Performance and marker selection were tracked.

The final model size as determined by AIC and BIC was too large, as shown on FIGS. 51 and 52, so combinatorics were used to improve the model. All of the models (a total of 60,459) of size 1-6 were evaluated and the best was selected based on AIC/BIC. The ten best AIC Models all contained Age, LN_SBP, CAD, and ST2>=35; 9 contain LN_NTBNP. Nine of the models had size=6 (1 of size=5). The ten best BIC Models all contained Age; 7 contain LN_NTBNP, and 8 contain ST2>=35. The BIC models were much smaller (k=2(3), k=3(6), k=4(1).

Two models were selected as the best. The first [Age+LN SBP+CAD+ST2>=35+LN_NTBNP] had a fitted AUC=0.791, and the second [Age+ST2>=35+LN_NTBNP] had a fitted AUC=0.755 (pr(ROC1=ROC2)=0.0714). The second model was more discriminating than NTPro Alone (AUC=0.68; p=0.181), ST2 alone (AUC=0.692; p=0.233), and a model of ST2 and BNP (AUC=0.721; p=0.2735). Comparisons of the two models are shown in FIGS. 53-54.

As shown in FIG. 55, when compared with the "out of bag" estimates, the five parameter Model had a Median AUC=0.758 (IQR: 0.726-0.788). The three Parameter Model had a Median AUC=0.738 (IQR:0.707-0.769). The 5 parameter model had a higher AUC on 77.5% of the replicates. Model calibration, shown in FIG. 56, was close to expected (red), as is usually the case when a training population is used.

Assuming a median split in the 5 parameter model, the model had a Sensitivity=0.79, Specificity=0.62, PPV=0.46, NPV=0.88, and Odds Ratio=6.0. Exemplary Model Parameters are shown in FIG. 57.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for evaluating the risk of mortality due to heart failure for a subject within one year and treating the subject, the method comprising:
    (a) performing an immunoassay to determine a level of soluble ST2 in a sample obtained from the subject;
    (b) determining a multimarker mortality risk score for a subject having heart failure using an algorithm selected from the group consisting of:
    (1) age of the subject (AGE)+the level of soluble ST2 in the subject (ST2)+a natural logarithm of a systolic blood pressure (ln_SBP)+a history of cardiovascular disease (CAD)+a natural logarithm of a level of N-terminal pro-brain natriuretic peptide (ln_NTpro-BNP);
    (2) AGE+ST2+ln_NTpro-BNP;
    (3) AGE+ST2+a level of troponin in the subject (Troponin)+a New York Heart Association score (NYHA);
    (4) AGE+ST2+[Troponin OR NYHA];
    (5) AGE+ST2+[Troponin AND/OR NYHA]+a natural logarithm of a level of hemoglobin (ln_Hgb);
    (6) AGE+ST2+[Troponin AND/OR NYHA]+ln_Hgb;
    (7) AGE+ST2+[Troponin AND/OR NYHA]+ln_Hgb+ln_SBP; and
    (8) AGE+ST2+[Troponin AND/OR NYHA]+ln_Hgb+ln_SBP+ln_NTpro-BNP;
    (c) comparing the multimarker mortality risk score to a reference multimarker mortality risk score;
    (d) identifying a subject having an elevated multimarker mortality risk score as compared to the reference multimarker mortality risk score as having an increased risk of mortality due to heart failure within one year; and
    (e) administering inpatient treatment to the identified subject or performing increased cardiac monitoring on the identified subject.

2. The method of claim 1, wherein the level of soluble ST2 is compared to a threshold and the presence of a level at or above the threshold is scored as "1" and the presence of a level below the threshold is scored as "0".

3. The method of claim 2, wherein the threshold is 35 or 50 ng/mL.

4. The method of claim 3, wherein algorithm (1) or (2) is used and the threshold level of ST2 is 35 ng/mL.

5. The method of claim 3, wherein algorithm (3) or (4) is used and the threshold level of ST2 is 50 ng/mL.

6. The method of claim 1, wherein the subject has been diagnosed with heart failure.

7. The method of claim 1, wherein the reference multimarker mortality risk score represents a score corresponding to a low risk of death within one year or within five years.

8. The method of claim 1, wherein the sample comprises serum, blood, or plasma.

9. The method of claim 1, wherein the subject has a BMI of 25-29, a BMI of ≥30, or renal insufficiency.

10. The method of claim 1, wherein the multimarker mortality risk score is determined for the subject using algorithm (1).

11. The method of claim 1, wherein the multimarker mortality risk score is determined for the subject using algorithm (2).

12. The method of claim 1, wherein the multimarker mortality risk score is determined for the subject using algorithm (3).

13. The method of claim 1, wherein the multimarker mortality risk score is determined for the subject using algorithm (4).

14. The method of claim 1, wherein the multimarker mortality risk score is determined for the subject using algorithm (5).

15. The method of claim 1, wherein the multimarker mortality risk score is determined for the subject using algorithm (6).

16. The method of claim 1, wherein the multimarker mortality risk score is determined for the subject using algorithm (7).

17. The method of claim 1, wherein the multimarker mortality risk score is determined for the subject using algorithm (8).

18. The method of claim 1, wherein step (e) comprises administering inpatient treatment to the identified subject.

19. The method of claim 1, wherein step (e) comprises performing increased cardiac monitoring on the identified subject.

* * * * *